United States Patent
McAllister et al.

(10) Patent No.: US 10,183,991 B2
(45) Date of Patent: *Jan. 22, 2019

(54) ANTIBODIES THAT RECOGNIZE A DENN/MADD-DOMAIN-CONTAINING 1A VARIANT 2 (DENND1A VARIANT 2)

(71) Applicants: VIRGINIA COMMONWEALTH UNIVERSITY, Richmond, VA (US); THE PENN STATE RESEARCH FOUNDATION, University Park, PA (US)

(72) Inventors: Janette M. McAllister, Hummelstown, PA (US); Jerome F. Strauss, Richmond, VA (US); Neil D. Christensen, Harrisburg, PA (US)

(73) Assignees: Virginia Commonwealth University, Richmond, VA (US); The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/590,377

(22) Filed: May 9, 2017

(65) Prior Publication Data

US 2017/0253648 A1 Sep. 7, 2017

Related U.S. Application Data

(62) Division of application No. 15/036,119, filed as application No. PCT/US2014/066257 on Nov. 19, 2014, now Pat. No. 9,676,844.

(60) Provisional application No. 62/042,852, filed on Aug. 28, 2014, provisional application No. 61/906,078, filed on Nov. 19, 2013.

(51) Int. Cl.
| | |
|---|---|
| *C07K 16/18* | (2006.01) |
| *A61K 39/395* | (2006.01) |
| *C12N 15/113* | (2010.01) |
| *G01N 33/68* | (2006.01) |

(52) U.S. Cl.
CPC .......... *C07K 16/18* (2013.01); *A61K 39/3955* (2013.01); *C12N 15/113* (2013.01); *G01N 33/6893* (2013.01); *C07K 2317/21* (2013.01); *C07K 2317/24* (2013.01); *C07K 2317/34* (2013.01); *C07K 2317/622* (2013.01); *C07K 2317/76* (2013.01); *G01N 2333/4706* (2013.01); *G01N 2800/36* (2013.01)

(58) Field of Classification Search
CPC ............... C07K 16/18; C07K 2317/24; G01N 33/6893; G01N 2800/36; G01N 2333/4706; C12N 15/113; A61K 39/3955
See application file for complete search history.

(56) References Cited

U.S. PATENT DOCUMENTS

| | | |
|---|---|---|
| 2009/0176235 A1 | 7/2009 | Cargill et al. |
| 2009/0220961 A1 | 9/2009 | Liu et al. |
| 2009/0221437 A1 | 9/2009 | Harkin et al. |
| 2011/0003704 A1 | 1/2011 | Skog et al. |

FOREIGN PATENT DOCUMENTS

| | | |
|---|---|---|
| WO | 0198353 A2 | 12/2001 |
| WO | 2011-150545 A1 | 12/2011 |
| WO | 2013-146765 A1 | 11/2013 |

OTHER PUBLICATIONS

Strauss et al.; "Persistence Pays Off for PCOS Gene Prostectors"; The Journal of Clinical Endocrinology and Metabolism, Jul. 2012, vol. 97, No. 7, pp. 2286-2288.
Eriksen et al.; Genetic Alterations within the DENND1A Gene in Patients with Polycystic Ovary Syndrome (PCOS); PLoS ONE, Sep. 27, 2013, vol. 8, No. 9, pp. 1-7.
Welt et al.; "Variants in DENND1A are Associated with Polycystic Ovary Syndrome in Women of European Ancestry"; The Journal of Clinical Endocrinology and Metabolism, Jul. 2012, vol. 97, No. 7, pp. 1342-1347.
Paul; Fundimental Immunology, 3rd. edition, Chapt. 9, pp. 292-295, (1993).
Rudikoff et al.; "Single amino acid substitution altering antigen-binding specificity"; Proceeding of the National Academy of Sciences, vol. 79, Mar. 1982, pp. 1979-1983.
Coleman; "Effects of amino acid sequence changes on antibody-antigen interactions"; 55th Forum in Immunology, Research in Immunology,1994, pp. 33-36.
Stratagene Catalog, 1988, p. 39.
Goodarzi et al. "Replication of association of DENND1A and THADA variants with polycystic ovary syndrome in European cohorts," Journal of Medical Genetics, Dec. 17, 2011, pp. 90-95, vol. 49.

*Primary Examiner* — Robert S Landsman
(74) *Attorney, Agent, or Firm* — W&C IP

(57) ABSTRACT

Pharmaceutical compositions and methods for the treatment of DENND1A.V2 related disorders, such as PCOS, are provided. In particular, humanized and mouse monoclonal antibodies specific for DENND1A.V2 and methods for using the same are provided.

6 Claims, 16 Drawing Sheets
Specification includes a Sequence Listing.

scFV DNA
*VH*-linker-*VL*,
5'-GAGGTGCAGCTGTTGGAGTCTGGGGGAGGCTTGGTACAGCCTGGGGGGTCCCTGAGACTCTCCTGTGCAGCCTC
TGGATTCACCTTTAGCAGCTATGCCATGAGCTGGGTCCGCCAGGCTCCAGGGAAGGGGCTGGAGTGGGTCTCAATTA
TTGGTACTGATGGTGATGATACAAATTACGCAGACTCCGTGAAGGGCCGGTTCACCATCTCCAGAGACAATTCCAAG
AACACGCTGTATCTGCAAATGAACAGCCTGAGAGCCGAGGACACGGCCGTATATTACTGTGCGAAAGCTGAAGCTAG
TTTTGACTACTGGGGCCAGGGAACCCTGGTCACCGTCTCGAGCggtggaggcggttcaggcggaggtggcagcggcg
gtggcgggtcgacg*GACATCCAGATGACCCAGTCTCCATCCTCCCTGTCTGCATCTGTAGGAGACAGAGTCACCATC
ACTTGCCGGGCAAGTCAGAGCATTAGCAGCTATTTAAATTGGTATCAGCAGAAACCAGGGAAAGCCCCTAAGCTCCT
GATCTATGGTGCATCCGATTTGCAAAGTGGGGTCCCATCAAGGTTCAGTGGCAGTGGATCTGGGACAGATTTCACTC
TCACCATCAGCAGTCTGCAACCTGAAGATTTTGCAACTTACTACTGTCAACAGTATGATTCTGCTCCTAGTACGTTC
GGCCAAGGGACCAAGGTGGAAATCAAACGG*-3' (SEQ ID NO:52)

Figure 9A scFv Protein
VH-linker-VL, CDRs framed in boxes
EVQLLESGGGLVQPGGSLRLSCAASGFTFS SYAMS WVRQAPGKGLEWVS IIGTDGDDTNYADSVKGRFT ISRDNSKN
TLYLQMNSLRAEDTAVYYCAK AEASFDY WGQGTLVTVSSggggsggggsggggs*DIQMTQSPSSLSASVGDRVTIT
CRASQSISSYLN WYQQKPGKAPKLLIY GASDLQS GVPSRFSGSGSGTDFTLTISSLQPEDFATYYC QQYDSAPSTF
GQGTKVEIKR* (SEQ ID NO:53)

Figure 9B

DNA Sequence of the Heavy Chain of Human Recombinant DENND1.V2 IgG1
5'_atggatagccgtctgaacctggtcttcctggtcctgattctgaaaggggt*g*GAGGTGCAGCTGTTGGAGTCTGG
GGGAGGCTTGGTACAGCCTGGGGGGTCCCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCAATTATTGGTACTGATGGTGATGATACAAAT
TACGCAGACTCCGTGAAGGGCCGGTTCACCATCTCCAGAGACAATTCCAAGAACACGCTGTATCTGCAAATGAACAG
CCTGAGAGCCGAGGACACGGCCGTATATTACTGTGCGAAAGCTGAAGCTAGTTTTGACTACTGGGGCCAGGGAACCC
TGGTCACCGTCTCGAGCgctagcaccaagggcccatcggtcttccccctggcaccctcctccaagagcacctctggg
ggcacagcggccctgggctgcctggtcaaggactacttccccgaaccggtgacggtgtcgtggaactcaggcgccct
gaccagcggcgtgcacaccttcccggctgtcctacagtcctcaggactctactccctcagcagcgtggtgaccgtgc
cctccagcagcttgggcacccagacctacatctgcaacgtgaatcacaagcccagcaacaccaaggtggacaagaaa
gttgagcccaaatcttgtgacaaaactcacacatgcccaccgtgcccagcacctgaactcctggggggaccgtcagt
cttcctcttccccccaaaacccaaggacaccctcatgatctcccggacccctgaggtcacatgcgtggtggtggacg
tgagccacgaagaccctgaggtcaagttcaactggtacgtggacggcgtggaggtgcataatgccaagacaaagccg
cgggaggagcagtacaacagcacgtaccgtgtggtcagcgtcctcaccgtcctgcaccaggactggctgaatggcaa
ggagtacaagtgcaaggtctccaacaaagcctcccagccccatcgagaaaaccatctccaaagccaaagggcagc
cccgagaaccacaggtgtacaccctgcctccatctcgggatgagctgaccaagaaccaggtcagcctgacctgcctg
gtcaaggcttctatcccagcgacatcgccgtggagtgggagagcaatgggcagccggagaacaactacaagaccac
gcctcccgtgctggactccgacggctccttcttcctctatagcaagctcaccgtggacaagagcaggtggcagcagg
ggaacgtcttctcatgctccgtgatgcatgaggctctgcacaaccactacacgcagaagagcctctccctgtctccg
ggtaaa_3'(SEQ ID NO:56)

Figure 10A

DNA Sequence of the Light Chain of Human Recombinant DENND1.V2 IgG1
5'_atgggttggtcctgtattatcctgttcctggtcgctactgctactggggtgcatagtGACATCCAGATGACCCA
GTCTCCATCCTCCCTGTCTGCATCTGTAGGAGACAGAGTCACCATCACTTGCCGGGCAAGTCAGAGCATTAGCAGCT
ATTTAAATTGGTATCAGCAGAAACCAGGGAAAGCCCCTAAGCTCCTGATCTATGGTGCATCCGATTTGCAAAGTGGG
GTCCCATCAAGGTTCAGTGGCAGTGGATCTGGGACAGATTTCACTCTCACCATCAGCAGTCTGCAACCTGAAGATTT
TGCAACTTACTACTGTCAACAGTATGATTCTGCTCCTAGTACGTTCGGCCAAGGGACCAAGGTGGAAATCAAACGTa
cggtggctgcaccatctgtcttcatcttcccgccatctgatgagcagttgaaatctggaactgcctctgttgtgtgc
ctgctgaataacttctatcccagagaggccaaagtacagtggaaggtggataacgccctccaatcgggtaactccca
ggagagtgtcacagagcaagacagcaaggacagcacctacagcctcagcagcaccctgacgctgagcaaagcagact
acgagaaacacaaagtctacgcctgcgaagtcacccatcagggcctgagctcgcccgtcacaaagagcttcaacagg
ggagagtgt_3'(SEQ ID NO:57)

Figure 10B

Protein Sequence of the Heavy Chain of Human Recombinant DENND1.V2 IgG1
VH- [CDRs underlined and bracketed]
MDSRLNLVFLVLILKGVQCEVQLLESGGGLVQPGGSLRLSCAASGFTFS[SYAMS]WVRQAPGKGLEWVS[IIGTDG
DDTNYADSVKGRFT]ISRDNSKNTLYLQMNSLRAEDTAVYYCAK[AEASFDY]WGQGTLVTVSSASTKGPSVFPLAP
SSKSTSGGTAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMHEALHNHYTQ
KSLSLSPGK (SEQ ID NO:58)

Figure 10C

Protein Sequence of the Light Chain of Recombinant DENND1.V2 IgG1
VL- [CDRs are underlined and bracketed]
MRPSIQFLGLLLFWLHGAQCDIQMTQSPSSLSASVGDRVTITC[RASQSISSYLN]WYQQKPGKAPKLLIY[GASDL
QS]GVPSRFSGSGSGTDFTLTISSLQPEDFATYYC[QQYDSAPSTF]GQGTKVEIKRTVAAPSVFIFPPSDEQLKSG
TASVVCLLNNFYPREAKVQWKVDNALQSGNSQESVTEQDSKDSTYSLSSTLTLSKADYEKHKVYACEVTHQGLSSPV
TKSFNRGEC (SEQ ID NO:59)

Figure 10D

Project ID: Phage Display Screening
DENND1A.V2 IgG1

Product Type: IgG1

| Label ID | Volume | Concentration | Total Amount |
|---|---|---|---|
| 79 | 1.0 mL | 0.126 mg/mL | 1.0 mg |

Method of Production: A plasmid vector was transfected into 293E cells. The suspension culture was collected 96 hours after transfection. The product was purified by HiTrap rProteinA FF and filtered by 0.2 μm.
Concentration Measurement: BCA method
Calculated Concentration 126 μg/mL
Total Amount: 1008 μg   Formulation Buffer: 0.1M glycine-HCl, 0.05M Tris, pH7.4

Figure 11A

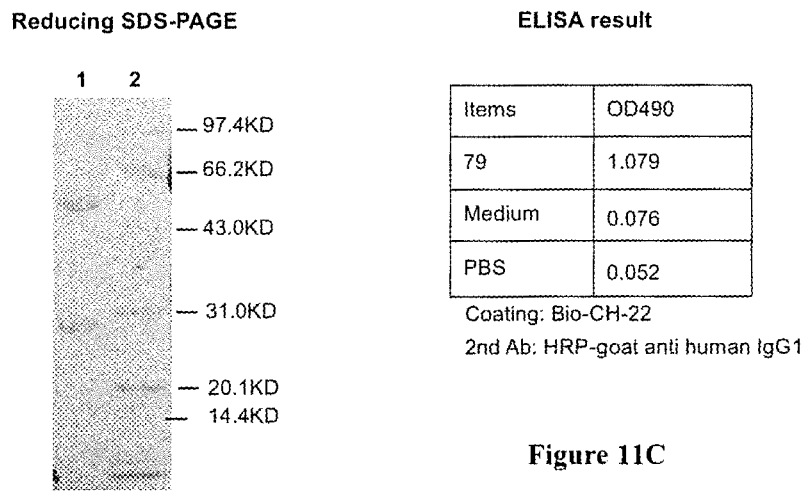

Reducing SDS-PAGE

1   2

— 97.4KD
— 66.2KD
— 43.0KD
— 31.0KD
— 20.1KD
— 14.4KD

Lane1: DENND1A.V2 IgG1
Lane2: Marker

Figure 11B

ELISA result

| Items | OD490 |
|---|---|
| 79 | 1.079 |
| Medium | 0.076 |
| PBS | 0.052 |

Coating: Bio-CH-22
2nd Ab: HRP-goat anti human IgG1

Figure 11C

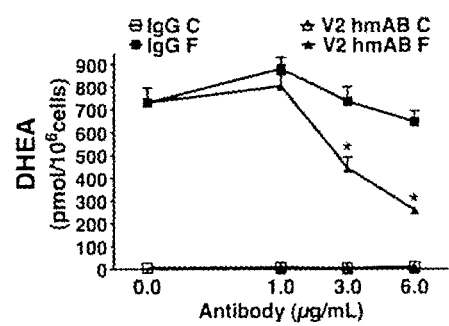
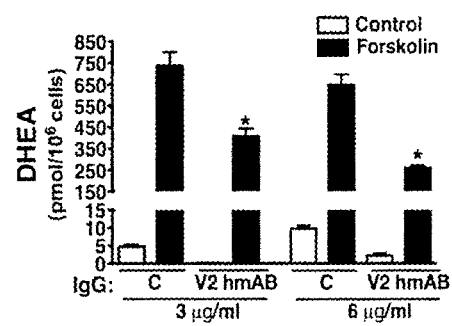
Figure 12A                    Figure 12B

P1B2 mouse mAB DNA Heavy Chain sequence
CAGCAGTCTGGGGCAGACCTTGTGAGGTCAGGGGCCTCAGTCAAGTTGTCCTGCACAGCTTCTGGCTTCAACAT
TAAAGACTTCTATATGCACTGGGTGAAGCAGAGGCCTGAACAGGGCCTGGAGTGGATTGGATGGATTGATCCTG
AGAATGGTGATACTGATTATGCCCCGAAGTTCCAGGGCAGGGCCACTATGACTGCAGACACATCCTCCAACACA
GCCTACCTGCAGCTCAACAGCCTCACATCTGAGGACACTGCCGTCTATTACTGTAATGCCCATACCTTCCTGCA
TGGTAACTCCGAACCTATGGACTACTGGGGTCAAGGAACCTCAGTCACCGTCTCC (SEQ ID NO:60)

Figure 16A

P1B2 mouse mAB DNA Light Chain sequence
*ATTGTGATGACCCAGTCTCCAAAATTCATGTCCACATCAGTAGGAGACAGGGTCAGCATCACCTGCAAGGCCAG
TCAGGATGTGATTGCTGCTGTTGCCTGGTATCAACAGAAACCAGGACAATCTCCTGAACTACTGATTTACTCGG
CATCCTACCGCTACACTGGAGTCCCTGATCGCTTCACTGGCAGTGGATCTGGGACGGATTTCACTTTCACCATC
AGCAGTGTGCAGGCTGAAGACCTGGCAGTTTATTACTGTCAGCAACATTATAGTACTCCGTGGACGTTCGGTGG
AGGCACCAAGCTGGACATCAAACGGGCT* (SEQ ID NO:61)

Figure 16B

P1B2 mouse mAB Heavy Chain Protein Sequence
VH- [CDRs are underlined and bracketed]
*QQSGADLVRSGASVKLSCTAS[GFNIKDFYMH]WVKQRPEQGLEWIG[WIDPENGDTD]YAPKFQGRATMTADT
SSNTAYLQLNSLTSEDTAVYYCNA[HTFLHGNSEPMDY]WGQGTSVTVS* (SEQ ID NO:62)

Figure 16C

P1B2 mouse mAB Light Chain Protein Sequence
*VL- [CDRs are underlined and bracketed]*
*IVMTQSPKFMSTSVGDRVSITC[KASQDVIAAVA]WYQQKPGQSPELLIY[SASYRYT]GVPDRFTGSGSGTDF
TFTISSVQAEDLAVYYC[QQHYSTPWT]FGGGTKLDIKRA* (SEQ ID NO:63)

Figure 16D

P1C5 mouse mAB DNA Heavy Chain sequence
CAAGTNCAGCTGCAGCAGTCTGGGGCAGAGCTTGTGAGGTCAGGGGCCTCAGTCAAGTTGTCCTGCACAGCTTC
TGGCTTCAACATTAAAGACTACTATATGCACTGGGTGAAGCAGAGGCCTGAACAGGGCCTGGAGTGGATTGGAT
GGATTGATCCTGAGAATGGTGATACTGAATATGCCCCGAAGTTCCAGGGCAAGGCCACTCTGACTGCAGACACA
TCCTCCAACACAGCCTACCTGCAACTCAGCAGCCTGACATCTGAGGACACTGCCGTCTATTACTGTAATGCCCA
CTACGGTACTAGCCAGGGGCTATGGACTACTGGGGTCAAGGAACCTCAGTCACCGTCTCC (SEQ ID NO:64)

Figure 16E

P1C5 mAB Heavy Chain Protein Sequence
VH- [CDRs are underlined and bracketed]
QVQLQQSGAELVRSGASVKLSCTAS[GFNIKDYYMH]WVKQRPEQGLE[WIGWIDPENGDTE]YAPKFQG
KATLTADTSSNTAYLQLSSLTSEDTAVYYC[NAHYGTSQGAMDY]WGQGTSVTVS (SEQ ID NO:65)

Figure 16F

ANTIBODIES THAT RECOGNIZE A DENN/MADD-DOMAIN-CONTAINING 1A VARIANT 2 (DENND1A VARIANT 2)

CROSS REFERENCE TO RELATED APPLICATIONS

This application is a continuation of U.S. application Ser. No. 15/036,119 filed May 12, 2016, now U.S. Pat. No. 9,676,844, which is a National Stage Application based on the International Application No. PCT/US2014/066257 filed Nov. 19, 2014 which claims priority to U.S. Provisional application No. 61/906,078, filed on Nov. 19, 2013 and U.S. Provisional Application No. 62/042,852, filed on Aug. 28, 2014, the disclosures of each of which are incorporated herein by reference.

STATEMENT AS TO RIGHTS TO INVENTIONS MADE UNDER FEDERALLY SPONSORED RESEARCH AND DEVELOPMENT

This invention was made with government support under Grant Nos. HD033852, HD034449 and HD058300, awarded by the National Institutes of Health. The government has certain rights in the invention.

FIELD OF THE INVENTION

The present invention relates generally to disorders that correlate with expression of DENND1A.V2 (DENN/MADD domain containing 1A variant 2) mRNA and/or protein, including without limitation polycystic ovary syndrome (PCOS), and more specifically to compositions and methods for prophylaxis and/or therapy of these disorders.

BACKGROUND OF THE INVENTION

Polycystic ovary syndrome (PCOS) is one of the most common endocrinopathies that affects 5-7% of reproductive age women world-wide [1]. It is associated with hyperandrogenemia/hyperandrogenism, anovulation, infertility, and a characteristic ovarian morphology consisting of multiple small subcortical follicular "cysts" embedded in bilaterally enlarged ovaries [2-5]. The presence of an elevated level of circulating testosterone results primarily from increased production of androgens by the ovaries, and is a classical endocrine phenotype of women with PCOS. Although there has been debate about the diagnostic criteria for PCOS, hyperandrogenemia/hyperandrogenism and anovulation, not explained by other causes, is a hallmark of the disorder, and is included as a key element in all "consensus" diagnosis schemes [6-10]. There is consensus that the ovarian theca cells are the primary source of excess androgen biosynthesis in women with PCOS [11-13]. Studies on freshly isolated theca tissue, or cultures of theca cells derived from normal and PCOS women have demonstrated that PCOS theca secretes greater amounts of androgen than theca tissue or cells from regularly ovulating women [12, 14-19]. Increased thecal androgen biosynthesis in PCOS theca cells results from increased expression of the key enzymes involved in androgen biosynthesis, cytochrome P450 17 alpha hydroxylase (encoded by the CYP17A1 gene) and cytochrome P450 cholesterol side chain cleavage (encoded by the CYP11A1 gene) [15-17, 20].

SUMMARY OF THE INVENTION

The development of conditions to propagate theca cells isolated from individual, size-matched follicles from ovaries of normal cycling and PCOS women, provided the first evidence that successively passaged PCOS theca cells retain the ability to produce augmented levels of androgens and progesterone compared normal theca cells [15, 16, 21]. This increase in androgen and progesterone biosynthesis in PCOS theca cells has been attributed, in part, to increased CYP17A1 and CYP11A1 gene transcription and RNA stability [17, 20, 22]. Molecular characterization of normal and PCOS theca cells from multiple individuals by microarray analysis and quantitative PCR also established that normal and PCOS cells have distinctive molecular signatures [16, 23, 24]. These findings are consistent with the notion of an intrinsic abnormality in PCOS theca that promotes hypersecretion of androgens in response to tropic stimulation. The theca cell culture system provides a unique platform for identifying the biochemical and molecular mechanisms underlying genetic abnormalities in PCOS women.

In the present disclosure, data is presented which demonstrates that an alternatively spliced, truncated form of DENND1A, DENND1A.V2 [25, 26], is differentially expressed in normal and PCOS theca cells. The data demonstrates that DENND1A.V2 contributes to the pathophysiological state of increased CYP17A1 and CYP11A1 gene expression and augmented androgen and progestin biosynthesis by PCOS theca cells [17, 20, 22]. Moreover, data presented herein demonstrates that targeting DENND1A.V2 using either shRNA or antibody-based approaches can suppress CYP17A1 and CYP11A1 gene expression and the increased androgen production exhibited by PCOS theca cells. Thus, inhibiting the increased androgen expression that is a hallmark of PCOS will have a prophylactic and/or therapeutic effect in PCOS patients, as well as in individuals who have other disorders that are positively associated with DENND1A.V2 expression.

One aspect of the invention comprises administering to a subject in need thereof a composition comprising an effective amount of a DENND1A.V2 targeting agent such that a prophylactic and/or therapeutic benefit is attained. Exemplary targeting agents include, but are not limited to, antibodies or antigen binding fragments and RNAi, shRNA or other nucleotide containing compositions. In some embodiments, the subject is in need of treatment for any disorder that is positively correlated with DENND1A.V2 expression. In some embodiments the disorder is correlated with DENND1A.V2 that is increased relative to a reference. In additional embodiments, the individual is at risk for, suspected of having, or has been diagnosed with PCOS.

Other aspects of the invention relate to pharmaceutical compositions comprising an antibody or an antigen binding fragment thereof that specifically recognizes DENND1A.V2 protein and does not specifically recognize DENND1A.V1 (DENN/MADD domain containing 1A variant 1) protein. Examples of antigen binding fragments include, but are not limited to, Fab fragments, Fab' fragments, F(ab'), fragments, Fd fragments, Fv fragments, scFv fragments, and combinations thereof. In preferred embodiments, the antibody or antigen binding fragment specifically recognizes at least one epitope present in the distinct DENND1A.V2 C-terminal amino acid sequence: NTIATPATLHILQKSITHFAAKFPTRGWTSSSH (SEQ ID NO:5).

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

As shown in FIG. 1C, DENND1A.V1 was increased by forskolin treatment in normal theca cells (*, $P<0.01$). Forskolin-stimulated DENND1A.V1 was decreased in PCOS theca cells as compared normal cells (**, $P<0.01$) (FIG. 1C). The ratio of DENND1A.V2/V1 was increased (*, $P<0.01$) in PCOS theca cells under control and forskolin-stimulated conditions (FIG. 1D). In FIG. 1E, Western analyses was performed to evaluate the efficacy of a rabbit polyclonal antibody, generated against the 21 amino acid peptide (QKSITHFAAKFPTRGWTSSSH)(SEQ NO:6) that is specific to DENND1A.V2, using whole cell extracts from normal and PCOS theca cells treated as described above. As shown in FIG. 1E, representative Western Blot analysis demonstrated an increase in 62 kD DENND1A.V2 in PCOS theca cells treated under both basal and forskolin-stimulated conditions. Total mTOR was used for protein normalization. As shown in FIG. 1F, cumulative analysis of whole cell lysates harvested from theca cells isolated from 4 independent normal and 4 independent PCOS women, demonstrated that DENND1A.V2 protein is significantly increased in PCOS theca cells as compared to normal theca cells under both control and forskolin-stimulated conditions (*$P<0.01$). Forskolin treatment did not appear to affect DENND1A.V2 protein accumulation in normal or PCOS theca cells.

In FIG. 2A, DENND1A.V2 protein was localized in the theca interna of the ovarian follicles, and was increased in PCOS theca (bottom) as compared to normal theca (top). In FIG. 2B, DENND1A.V2 staining in PCOS theca and granulosa cells is presented in the left panel (40×). Staining, primarily in the PCOS theca cell nuclei, cytoplasm, and cell membrane, is shown in the right panel (100× under oil).

As shown in FIG. 6C, DENND1A.V2 adenovirus infection increases both basal (*, $P<0.05$) and forskolin-stimulated (**, $P<0.05$) −770CYP17A1 promoter activity, as compared to Null control adenovirus. In FIG. 6D, a CYP11A1 promoter construct (−160/−90 CYP11A1/LUC) which confers increased CYP11A1 expression in PCOS theca cells to examine the effects of DENND1A.V2 on CYP11A1 transcription in theca cells. Normal theca cells were transfected with the −160/−90 CYP11A1/LUC plasmid with an DENND1A.V2/pCMV-XL4 or control pCMV-XL4 plasmid. As shown in FIG. 6D, DENND1A.V2 significantly increased forskolin-stimulated (*, $P<0.001$) −160/−90 CYP11A1/LUC promoter activity as compared to empty plasmid. These combined data demonstrate that DENND1A.V2 induces increased transcriptional activation of CYP17A1 and CYP11A1 gene expression.

As shown in FIG. 7C, co-transfection of −235/+44 of the CYP17A1 promoter fused to the luciferase gene in a pGL3 plasmid (−235 CYP17A1/LUC) with DENND1A.V2 shRNA1 and shRNA2 plasmids resulted in a significant inhibition of forskolin-dependent CYP17A1 reporter activity in PCOS theca cells, compared to Scrambled shRNA (P<0.05). Infection with silencing shRNA DENND1A.V2 lentivirus particles significantly inhibited forskolin-stimulated 17OHP4 (FIG. 7D; *, P<0.001), DHEA (FIG. 7E; *, P<0.001), and progesterone biosynthesis (FIG. 7F; *, P<0.001), as compared to control non-silencing lentivirus. Thus, knock-down of DENND1A.V2 in PCOS theca cells converts the PCOS theca cells to a normal phenotype.

In FIG. 8A, rabbit polyclonal DENND1A.V2 IgG significantly inhibited forskolin-stimulated DHEA biosynthesis, with an approximate $ID_{50}$ of 0.25 μg/mL, compared to non-specific IgG. Experiments were performed to examine the effects of 0.5 μg/mL of polyclonal DENND1A.V2 specific IgG or 0.5 μg/mL non specific IgG on CYP17 (FIG. 8B) and CYP11A1 mRNA (FIG. 8C) accumulation in the absence (C) or presence of 20 μM forskolin (F), demonstrated that DENND1A.V2 specific IgG significantly inhibits CYP17A mRNA accumulation under control (*, P<0.01) and CYP17 mRNA and CYP11A1 mRNA under forskolin-stimulated (**, P<0.01) conditions in PCOS theca cells, while having no effect in normal theca cells. Parallel experiments to examine the effects of 0.5 μg/mL of DENND1A.V2 IgG or 0.5 μg/mL or control IgG on basal and forskolin-stimulated DHEA (FIG. 8D), 17OHP4 (FIG. 8E), and P4 (FIG. 8F) biosynthesis similarly demonstrated that polyclonal DENND1A.V2 specific IgG significantly inhibited forskolin-stimulated DHEA (FIG. 8D, *, P<0.001) and 17OHP4 (FIG. 8E, *, P<0.001), in PCOS theca cells, as compared to control IgG, without affecting normal theca cells.

FIG. 9A-B. Phage Display Screening of a Human Phage Library with DENND1A.V2 Peptide Identified Two Clones with Identical ScFv Sequences (SEQ ID NOs: 52-53). To obtain a humanized monoclonal antibody, a freshly made human phage library was used to perform phage display screening with the biotinylated C-terminal DENND1A.V2 21 amino acid peptide (i.e., QKSITHFAAKFPTRG-WTSSSH) (SEQ ID NO:6). Two ScFv clones, clones 16 and 79 were identified following ELISA screening (Tables 2-5). Sequence analysis of these clones demonstrated that the nucleotide (FIG. 9A) (SEQ ID NO:52) and amino acid (FIG. 9B) (SEQ ID NO:53) sequence of clones 16 and 79 were identical. As shown in FIG. 9B, the VH sequence comprises amino acid residues 1-116. The linker comprises residues 117-132 and the VL sequence comprises residues 133-240. For both FIGS. 9A and 9B, the variable region of the heavy chain (VH) is in capitals; the linker is in lower case; the variable region of the light chain (VL) is in underlined, italicized capitals. The complementary determining regions (CDRs) are in boxes (FIG. 9B).

FIG. 10A-D. Sequences of the Heavy and Light Chains of Humanized Monoclonal (Recombinant) Antibodies to DENND1A.V2 Peptide (SEQ ID NOs: 56-59). The VL and HL sequences of the scFv identified following phage display were cloned into the expression plasmids pIgG1-L and pIgG1-L. The sequence of the of the full length heavy chain of IgG1 (FIG. 10A; SEQ ID NO:56) and light chain of IgG1 (FIG. 10B; SEQ ID NO:57) of humanized monoclonal, or recombinant DENND1.V2 IgG1 were determined. The secretory signal peptide (SP) sequence for both the light and heavy chains is italicized in both FIGS. 10A-10B. For the heavy chain in FIG. 10A, the variable region of the heavy chain (VH) is upper case (i.e., capitals), and the remainder of the constant region of the heavy chain of human IgG1 is in lower case. For the light chain in FIG. 10B, the variable region of the light chain (VL) is italicized, underlined upper case, and the remainder of the constant region of the light chain of human IgG1 is in lower case. The protein sequence of the heavy and light chains are presented in FIGS. 10C-D. For both the heavy and light chains, the secretory signal peptide (SP) sequence is in italicized capitals, and the CDR are underlined and bracketed. For the heavy chain in FIG. 10C (SEQ ID NO:58), the variable region of the heavy chain (VH) is in capitals, the remainder of the constant region of the heavy chain of human IgG1 is in capitals. For the light chain in FIG. 10D (SEQ ID NO:59), the variable region of the heavy chain (VL) is in italicized capitals, and the remainder of the constant region of the light chain of human IgG1 is in capitals.

FIG. 11A-C. Human Recombinant DENND1A.V2 specific IgG1 expression and purification. To further assess the humanized monoclonal antibody that was obtained following phage screening, plasmid vectors encoding the heavy and light chains of the recombinant human DENND1A.V2 specific IgG1 were transfected and expressed in 293E cells. The suspension culture was collected 96 hours after transfection. The product was purified by HiTrap rProteinA FF and filtered by 0.2 μm. As shown in FIG. 11A, the humanized monoclonal antibody, or recombinant DENND1A.V2 specific IgG1 had a calculated concentration of 126 μg/ml. Reducing SDS-PAGE analysis demonstrated that the heavy and light chains of the recombinant DENND1A.V2 IgG1 are of the appropriate size (FIG. 11B). ELISA results demonstrating specific binding of the human recombinant DENND1A.V2 IgG1 to the 21 amino acid biotinylated DENND1A.V2 sequence (Bio-CH-22) are shown in FIG. 11C.

FIG. 12A-B. Recombinant human DENND1A.V2 specific IgG1 functionally inhibits DHEA biosynthesis in PCOS theca cells in a dose dependent manner. To examine whether recombinant human IgG1 specific to DENND1A.V2 functionally inhibits androgen biosynthesis, PCOS theca cells were treated with increasing concentrations (0.01-6 μg/mL) of the human recombinant monoclonal IgG1 specific for DENND1A.V2 (V2 hmAB) or a non-specific IgG1, treated in the absence (C) and presence of 20 μM forskolin (F) for 72 h. As shown in FIG. 12A, V2 hmAB significantly decreased (*, P<0.01) forskolin-stimulated DHEA biosynthesis with an approximate $ID_{50}$ of 1.8 μg/mL, compared to control IgG1. In FIG. 12B, both basal and forskolin (*, P<0.1) stimulated DHEA biosynthesis were inhibited following treatment with V2 hmAB as compared to control IgG1.

As shown in FIG. 13A, a maximal dose of V2 hmAB significantly (*, P<0.01) inhibited forskolin-stimulated DHEA biosynthesis in PCOS theca cells, while having minimal effect on normal theca cells. A comparison of the effects rabbit DENND1A.V2 polyclonal antibody (V2 polyclonal) versus human recombinant DENND1A.V2 IgG1 (V2 hmAB Recominant) demonstrates that both of these antibodies similarly reduce DHEA biosynthesis as compared to control IgG (FIG. 13B).

As shown in FIG. 15, DENND1A.V2 specific P1B2 and P1C5 mouse IgG1 inhibited forskolin-stimulated DHEA accumulation in PCOS theca cells (*, P<0.05), compared to negative control mouse IgG1.

FIG. 16A-F. Sequences of the DENND1A.V2 specific mouse monoclonal antibodies P1B2 and P1C5 (SEQ ID NOs:60-65). The mouse monoclonal DENND1A.V2 specific IgG1, P1B2 heavy chain (FIG. 16A) (SEQ ID NO:60), P1B2 light chain (FIG. 16B) (SEQ ID NO:61), and the heavy chain of P1C5 (FIG. 16E)(SEQ ID NO:64) nucleotide sequences were determined. The DNA sequence of the heavy chain of P1B2 is in capitals, and light chain of P1B2 is in underlined and italicized capitals. For the protein sequences of the heavy chain of P1B2 (FIG. 16C) (SEQ ID NO:62) and the heavy chain of P1C5 (FIG. 16F) (SEQ ID NO:65) are in capitals, and light chain of P1B2 is italicized (FIG. 16D) (SEQ ID NO:63) The CDR residues are underlined and bracketed. The uncertain amino acid sequences are indicated in italics.

DETAILED DESCRIPTION

Figure 1A:
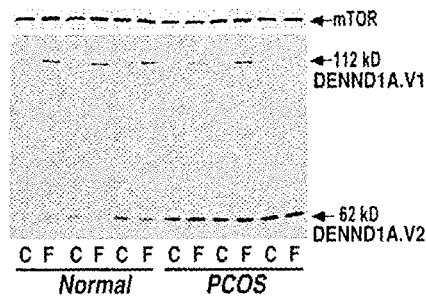
FIG. 1A-F. DENND1A.V2 protein is increased in PCOS theca cells. Representative Western analysis of ~62 kD DENND1A.V2 and ~112 kD DENND1A.V1 in whole cell extracts from normal and PCOS theca cells treated in the absence (−) and presence (+) of 20 µM forskolin. Total mTOR was used for protein normalization (FIG. 1A). Quantitative data from Western analyses from theca cells isolated from 5 normal cycling and 5 PCOS subjects, presented as the mean±SEM, demonstrated that DENND1A.V2 protein was increased in both basal and forskolin-stimulated (*, $P<0.01$) PCOS theca cells as compared to normal theca cells (FIG. 1B).

Embodiments of the invention relate to a pharmaceutical composition comprising an antibody or an antigen binding fragment thereof, wherein the antibody or the antigen binding fragment thereof specifically recognizes DENND1A.V2 protein and does not specifically recognize DENND1A.V1 protein. Additional embodiments of the invention relate to a method for prophylaxis and/or therapy of a disorder that is positively correlated with expression of DENND1A.V2 mRNA and/or protein comprising administering to a subject in need thereof a therapeutically effective amount of a pharmaceutical composition comprising an antibody or an antigen binding fragment thereof, wherein the antibody or the antigen binding fragment thereof specifically recognizes DENND1A.V2 protein and does not specifically recognize DENND1A.V1 protein.

The DENND1A.V2 cDNA sequence is:

```
                                                   (SEQ ID NO: 1)
0001  cgcgcgccgg gcacgcgcgc cggcgaccat ggcgttcgcc gggctggagc gagtacatta 0061  accccctggag gcggcggcgg cggcgaggga gcgagcctcg agcgggcggg ccccagcctg 0121  agggaaggga ggaaggggcg gggagagcgc cagagggagg ccggtcggcc gcgggcgggc 0181  gggcagcgca gcgccgagcg gggcccgcgg gcccatgagg aggcctgggg accatgggct 0241  ccaggatcaa gcagaatcca gagaccacat ttgaagtata tgttgaagtg gcctatccca 0301  ggacaggtgg cactctttca gatcctgagg tgcagaggca attcccggag gactacagtg 0361  accaggaagt tctacagact ttgaccaagt tttgtttccc cttctatgtg gacagcctca 0421  cagttagcca agttggccag aacttcacat tcgtgctcac tgacattgac agcaaacaga 0481  gattcgggtt ctgccgctta tcttcaggag cgaagagctg cttctgtatc ttaagctatc 0541  tcccctggtt cgaggtattt tataagctgc ttaacatcct ggcagattac acgacaaaaa 0601  gacaggaaaa tcagtggaat gagcttcttg aaactctgca caaacttccc atccctgacc 0661  caggagtgtc tgtccatctc agcgtgcatt cttattttac tgtgcctgat accagagaac 0721  ttcccagcac acctgagaat agaaatctga cagaatattt tgtggctgtg gatgttaaca 0781  acatgttgca tctgtacgcc agtatgctgt acgaacgccg gatactccatc atttgcagca
```

```
0841 aactcagcac tctgactgcc tgcatccacg ggtctgcggc
     gatgctctac cccatgtact
0901 ggcagcacgt gtacatcccc gtgctgccgc cgcatctgct
     ggactactgc tgtgctccca
0961 tgccctacct cataggaatc catttaagtt taatggagaa
     agtcagaaac atggccctgg
1021 atgatgtcgt gatcctgaat gtggacacca cacccctgga
     aaccccttc gatgacctcc
1081 agagcctccc aaacgacgtg atctcttccc tgaagaacag
     gctgaaaaag gtctccacaa
1141 ccactgggga tggtgtggcc agagcgttcc tcaaggccca
     ggctgatttc ttcggtagct
1201 accgaaacgc tctgaaaatc gagccggagg agccgatcac
     tttctgtgag aagccttcg
1261 tgtcccacta ccgctccgga gccatgaggc agttcctgca
     gaacgccaca cagctgcagc
1321 tcttcaagca gtttattgat ggtcgattag atcttctcaa
     ttccggcgaa ggtttcagtg
1381 atgttttga agaggaaatc aacatgggcg agtacgctgg
     cagtgacaaa ctgtaccatc
1441 agtggctctc cactgtccgg aaaggaagtg gagcaattct
     gaatactgta aagaccaaag
1501 caaatccggc catgaagact gtctacaagt tcgcaaaaga
     tcatgcaaaa atgggaataa
1561 aagaggtgaa aaaccgcttg aagcaaaagg acattgccga
     gaatggctgc gcccccaccc
1621 cagaagagca gctgccaaag actgcaccgt ccccactggt
     ggaggccaag acccccaagc
1681 tccgagaaga ccggcggcca atcacagtcc actttggaca
     ggtgcgccca cctcgtccac
1741 atgttgttaa agaccaaag agcaacatcg cagtggaagg
     ccggaggacg tctgtgccga
1801 gccctgagca aaacaccatt gcaacaccag ctacactcca
     catcctacag aaaagcatta
1861 cccattttgc ggccaagttc ccgacgagag gctggacctc
     ttcatcacat tgacttacgc
1921 cgttgctttt ccagactggg cagaggggct gacttcgcag
     tgtgtgccaa agagccggtg
1981 tctgataatc ccatttttct gcttatcacc tgaactgtgt
     cagtatcact tttagttttg
2041 ttggttggtt ggtttgttgt ttgtttaata tgccctgttt
     tctacttctg ttggaaaata
2101 tttgggggttg aaataaacca gtgggagcat ggaaaaaaaa
     aaaaaaaaaa aaaaaaaaa
2161 aaaaaa
```

The DENND1A.V2 amino acid sequence is:

(SEQ ID NO: 2)
MGSRIKQNPETTFEVYVEVAYPRTGGTLSDPEVQRQFPEDYSDQEVLQTL
TKFCFPFYVDSLTVSQVGQNFTFVLTDIDSKQRFGFCRLSSGAKSCFCIL
SYLPWFEVFYKLLNILADYTTKRQENQWNELLETLHKLPIPDPGVSVHLS
VHSYFTVPDTRELPSIPENRNLTEYFVAVDVNNMLHLYASMLYERRILII
CSKLSTLTACIHGSAAMLYPMYWQHVYIPVLPPHLLDYCCAPMPYLIGIH
LSLMEKVRNMALDDVVILNVDTNTLETPFDDLQSLPNDVISSLKNRLKKV
STTTGDGVARAFLKAQAAFFGSYRNALKIEPEEPITFCEEAFVSHYRSGA
MRQFLQNATQLQLFKQFIDGRLDLLNSGEGFSDVFEEEINMGEYAGSDKL
YHQWLSTVRKGSGAILNTVKTKANPAMKTVYKFAKDHAKMGIKEVKNRLK
QKDIAENGCAPTPEEQLPKTAPSPLVEAKDPKLREDRRPITVHFGQVRPP
RPHVVKRPKSNIAVEGRRTSVPSPEQNTIATPATLHILQKSITHFAAKFP
TRGWTSSSH

The DENND1A.V1 cDNA sequence is:

```
                                        (SEQ ID NO: 3)
0001 cgcgcgccgg gcacgcgcgc cggcgaccat ggcgttcgcc
     gggctggagc gagtacatta
0061 acccctggag gcggcggcgg cggcgaggga gcgagcctcg
     agcgggcggg ccccagcctg
0121 agggaaggga ggaaggggcg gggagagcgc cagagggagg
     ccggtcggcc gcgggcgggc
0181 gggcagcgca gcgccgagcg gggcccgcgg gcccatgagg
     aggcctgggg accatgggct
0241 ccaggatcaa gcagaatcca gagaccacat ttgaagtata
     tgttgaagtg gcctatccca
0301 ggacaggtgg cactctttca gatcctgagg tgcagaggca
     attcccggag gactacagtg
0361 accaggaagt tctacagact ttgaccaagt tttgtttccc
     cttctatgtg gacagcctca
0421 cagttagcca agttggccag aacttccat tcgtgctcac
     tgacattgac agcaaacaga
0481 gattcgggtt ctgccgctta tcttcaggag cgaagagctg
     cttctgtatc ttaagctatc
```

-continued

```
0541 tcccctggtt cgaggtattt tataagctgc ttaacatcct
     ggcagattac acgacaaaaa
0601 gacaggaaaa tcagtggaat gagcttcttg aaactctgca
     caaacttccc atccctgacc
0661 caggagtgtc tgtccatctc agcgtgcatt cttattttac
     tgtgcctgat accagagaac
0721 ttcccagcat acctgagaat agaaatctga cagaatattt
     tgtggctgtg gatgttaaca
0781 acatgttgca tctgtacgcc agtatgctgt acgaacgccg
     gatactcatc atttgcagca
0841 aactcagcac tctgactgcc tgcatccacg ggtctgcggc
     gatgctctac cccatgtact
0901 ggcagcacgt gtacatcccc gtgctgccgc cgcatctgct
     ggactactgc tgtgctccca
0961 tgccctacct cataggaatc catttaagtt taatggagaa
     agtcagaaac atggccctgg
1021 atgatgtcgt gatcctgaat gtggacacca acaccctgga
     aacccccttc gatgacctcc
1081 agagcctccc aaacgacgtg atctcttccc tgaagaacag
     gctgaaaaag gtctccacaa
1141 ccactgggga tggtgtggcc agagcgttcc tcaaggccca
     ggctgctttc ttcggtagct
1201 accgaaacgc tctgaaaatc gagccggagg agccgatcac
     tttctgtgag gaagccttcg
1261 tgtcccacta ccgctccgga gccatgaggc agttcctgca
     gaacgccaca cagctgcagc
1321 tcttcaagca gtttattgat ggtcgattag atcttctcaa
     ttccggcgaa ggtttcagtg
1381 atgtttttga agaggaaatc aacatgggcg agtacgctgg
     cagtgacaaa ctgtaccatc
1441 agtggctctc cactgtccgg aaaggaagtg gagcaattct
     gaatactgta aagaccaaag
1501 caaatccggc catgaagact gtctacaagt tcgcaaaaga
     tcatgcaaaa atgggaataa
1561 aagaggtgaa aaaccgcttg aagcaaaagg acattgccga
     gaatggctgc gcccccaccc
1621 cagaagagca gctgccaaag actgcaccgt ccccactggt
     ggaggccaag gaccccaagc
1681 tccgagaaga ccggcggcca atcacagtcc actttggaca
     ggtgcgccca cctcgtccac
```

```
1741 atgttgttaa gagaccaaag agcaacatcg cagtggaagg
     ccggaggacg tctgtgccga
1801 gccctgagca gccgcagccg tatcggacac tcagggagtc
     agacagcgcg gaaggcgacg
1861 aggcagagag tccagagcag caagtgcgga agtccacagg
     ccctgtccca gctcccccctg
1921 accgggctgc cagcatcgac cttctggaag acgtcttcag
     caacctggac atggaggccg
1981 cactgcagcc actgggccag gccaagagct tagaggacct
     tcgtgccccc aaagacctga
2041 gggagcagcc agggaccttt gactatcaga ggctggatct
     gggcgggagt gagaggagcc
2101 gcggggtgac agtggccttg aagcttaccc acccgtacaa
     caagctctgg agcctgggcc
2161 aggacgacat ggccatcccc agcaagcccc cagctgcctc
     ccctgagaag ccctcggccc
2221 tgctcggaa ctccctggcc ctgcctcgaa ggccccagaa
     ccgggacagc atcctgaacc
2281 ccagtgacaa ggaggaggtg cccaccccta ctctgggcag
     catcaccatc ccccggcccc
2341 aaggcaggaa gaccccagag ctgggcatcg tgcctccacc
     gcccattccc cgcccggcca
2401 agctccaggc tgccggcgcc gcacttggtg acgtctcaga
     gcggctgcag acggatcggg
2461 acaggcgagc tgccctgagt ccagggctcc tgcctggtgt
     tgtccccaa ggccccactg
2521 aactgctcca gccgctcagc cctggccccg ggctgcaggg
     cacgagcagt gacgccctgc
2581 tcgccctcct ggacccgctc agcacagcct ggtcaggcag
     caccctcccg tcacgccccg
2641 ccaccccgaa tgtagccacc ccattcaccc cccaattcag
     cttcccccct gcagggacac
2701 ccaccccatt cccacagcca ccactcaacc cctttgtccc
     atccatgcca gcagccccac
2761 ccaccctgcc cctggtctcc acaccagccg ggcctttcgg
     ggcccctcca gcttccctgg
2821 ggccggcttt tgcgtccggc ctcctgctgt ccagtgctgg
     cttctgtgcc cctcacaggt
2881 ctcagcccaa cctctccgcc ctctccatgc ccaacctctt
     tggccagatg cccatgggca
```

```
2941 cccacacgag ccccctacag ccgctgggtc ccccagcagt
     tgccccgtcg aggatccgaa
3001 cgttgcccct ggcccgctca agtgccaggg ctgctgagac
     caagcagggg ctggccctga
3061 ggcctggaga ccccccgctt ctgcctccca ggcccctca
     aggcctggag ccaacactgc
3121 agccctctgc tcctcaacag gccagagacc cctttgagga
     tttgttacag aaaaccaagc
3181 aagacgtgag cccgagtccg gccctggccc cggccccaga
     ctcggtggag cagctcagga
3241 agcagtggga gaccttcgag tgagccgggc cctgagggtg
     ggggatgcac cgaggcccga
3301 gggtccgtcc actgctgcgg ttccgaggct cccccgccac
     tctctctctg cccaggttct
3361 gctggtggga agggatggga cccctctctg ctgccccctc
     ctcccctcca cactgcccat
3421 ctctgatgtc tggccctggg gaatggcacc agttccagcc
     tgggaatcaa cccagttcct
3481 gagtgcccat cccacccgc ggttgcctct cctcggcacc
     cttgattggg ttttgcacta
3541 aagaggtcag ctgggccaat gatattgctc cagaccgagt
     cctacccacc ttcccccgga
3601 agtgtcccaa gaggctccga aggcctcccc tccgagccca
     gctctcctgt ctcctccaca
3661 gccaggccct gcacgcccac tcctcggac acaggtgaca
     gggttaccct ccagtttgag
3721 ctcatctgca cgagacacag gtagcttggg gttgaagtta
     ggactcctcc tgggctggag
3781 gatttacctg gtggggcact tccagactgt ttctagcaat
     atacacacac gttctttcct
3841 gtgtcttcac cccaaaactt cagttgattc tgacctggga
     ggatctgggg accaggggt
3901 cttgggctgc cttgtgatac acagccccag ccaccctgca
     cggggctgc gagcaccagc
3961 aactttgatt tatagaagga aaatggaaac ccccatctga
     gtatttggg aggagccccc
4021 agccctcatc cagctctggc acgctgatac ctccaggtac
     tcccctcact gtcaaagctg
4081 gggctcagcc tcttgtcatc tggagctttg tgggcaaagc
     tgagaagctg caacccagat
4141 ttcaacccaa aaaggtcaag ctgaatgcct cagactgatg
     tggaaggcag ctggccttcc
4201 tgggttggaa cgaggcagtg ccctgagcc ccttctccag
     ggccaggtag aaaggacaaa
4261 cttggtctct gcctcgggga agcaggagga gggctagaag
     ccagtccctc cccacctgcc
4321 cagagctcca ggccagcaca gaaattcctg aggccaacgt
     caccaaagtt agattgaatg
4381 tttattatct ttcttttttcc ttttttacctt attgatttga
     tgaatcttga aatggattca
4441 tttccataaa ccaagttaaa gtatggcccg accatttaag
     aaaacaacca tctgagacac
4501 gcaggaaatt gtgagcattt cgacccgagc tctcatttcc
     tatttgtgaa gggtcagaca
4561 cagtctaccc aggggtgtct gggggacaag ggggtctctg
     gagatgtcac ccagggagcc
4621 ccctctatgt ctgagaggct gccactgctg cacatgctca
     gtgaggcttg gcggccatcc
4681 tggcacatgg ctcttcctgg gtcaaccgtg acctgtctgg
     ctcaggaatg ggctctggct
4741 gctggggag ccgtgtcact cctgggccat ggggcacct
     cctgggcact taggtgtttc
4801 agcatagatt ccagtttcgc accctgggca gaccccaggg
     ccccatccgg gatagggcag
4861 aggaggtgct ggcggcccca gggaaggagg gtgtgtaccc
     caaggccccc tggctgtgct
4921 gaggggctgg ggtgagcgct ccatgttcac atgagcactg
     ctgcctcttc acttgtggga
4981 cttttttgcaa acccaaggat gaactttgtg tgcattcaat
     aaaatcatct tggggaagag
5041 g
```

The DENND1A.V1 amino acid sequence is:

(SEQ ID NO: 4)
MGSRIKQNPETTFEVYVEVAYPRTGGTLSDPEVQRQFPEDYSDQEVLQTL
TKFCFPFYVDSLTVSQVGQNFTFVLTDIDSKQRFGFCRLSSGAKSCFCIL
SYLPWFEVFYKLLNILADYTTKRQENQWNELLETLHKEPIPDPGVSVHLS
VHSYFTVPDTRELPSIPENRNLTEYFVAVDVNNMLHLYASMLYERRILII
CSKLSTLTACIHGSAAMLYPMYWQHVYIPVLPPHLLDYCCAPMPYLIGIH
LSLMEKVRNMALDDVVILNVDTNTLETPFDDLQSLPNDVISSLKNRLKKV
STTTGDGVARAFLKAQAAFFGSYRNALKIEPEEPITFCEEAFVSHYRSGA

-continued

```
MRQFLQNATQLQLFKQFIDGRLDLLNSGEGFSDVFEEEINMGEYAGSDKL

YHQWLSTVRKGSGAILNTVKTKANPAMKTVYKFAKDHAKMGIKEVKNRLK

QKDIAENGCAPTPEEQLPKTAPSPLVEAKDPKLREDRRPITVHFGQVRPP

RPHVVKRPKSNIAVEGRRTSVPSPEQPQPYRTLRESDSAEGDEAESPEQQ

VRKSTGPVPAPPDRAASIDLLEDVFSNLDMEAALQPLGQAKSLEDLRAPK

DLREQPGTFDYQRLDLGGSERSRGVTVALKLTHPYNKLWSLGQDDMAIPS

KPPAASPEKPSALLGNSLALPRRPQNRDSILNPSDKEEVPTPTLGSITIP

RPQGRKTPELGIVPPPPIPRPAKLQAAGAALGDVSERLQTDRDRRAALSP

GLLPGVVPQGPTELLQPLSPGPGAAGTSSDALLALLDPLSTAWSGSTLPS

RPATPNVATPFTPQFSFPPAGTPTPFPQPPLNPFVPSMPAAPPTLPLVST

PAGPFGAPPASLGPAFASGLLLSSAGFCAPHRSQPNLSALSMPNLFGQMP

MGTHTSPLQPLGPPAVAPSRIRTLPLARSSARAAETKQGLALRPGDPPLL

PPRPPQGLEPTLQPSAPQQARDPFEDLLQKTKQDVSPSPALAPAPDSVEQ

LRKQWETFE
```

For each cDNA sequence presented herein, the invention includes the mRNA equivalent of the cDNA, meaning that the invention includes each cDNA sequence wherein each T is replaced by U.

In one aspect, the present disclosure comprises one or more isolated and/or recombinantly or otherwise synthesized (e.g. chemically synthesized) binding partners which specifically recognize the DENND1A.V2 protein, but do not specifically recognize DENND1A.V1 protein.

Such binding partners include antibodies and antigen binding fragments thereof that can specifically bind to the unique C-terminus of the DENND1A.V2 protein, such as Fab fragments, Fab' fragments, F(ab')₂ fragments, Fd fragments, Fv fragments, scFv fragments, aptamers, diabodies and combinations thereof. Single-chain Fv or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. The antibody and antigen binding fragments thereof are directed to one or more epitopes in the unique 33 amino acid C-terminus of the DENND1A.V2 protein. The 33 amino acid DENND1A.V2 sequence that is unique between DENND1A Variants 1 and 2 is:

```
                                        (SEQ ID NO: 5)
NTIATPATLHILQKSITHFAAKFPTRGWTSSSH.
```

This disclosure includes a demonstration of making antibodies directed to a segment of this unique DENND1A.V2 C-terminal amino acid sequence. In this regard, a DENND1A.V2 polyclonal antibody (rabbit) targeted to the following unique 21 amino acid sequence segment: QKSITHFAAKFPTRGWTSSSH (SEQ ID NO:6) was generated. This sequence was selected based on an analysis that predicted it to be optimally antigenic, and unlikely to result in production of antibodies that would have non-specific cross-reactivity with other proteins.

Figure 8A:
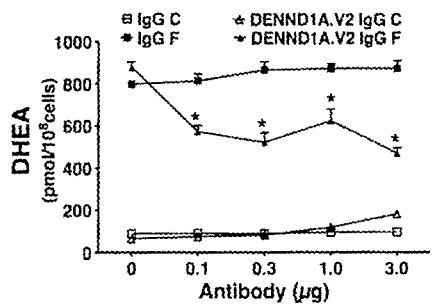
FIG. 8A-F. Rabbit polyclonal DENND1A.V2 specific IgG significantly reduces androgen biosynthesis and CYP17 and CYP11A1 mRNA PCOS theca cells. PCOS theca cells were treated with increasing concentrations (0.1-3.0 μg/mL) of an affinity purified rabbit polyclonal IgG that was generated against the unique C-terminal 21 amino acid sequence of DENND1A.V2 (i.e., QKSITHFAAKFPTRGWTSSSH) (SEQ ID NO:6), or non-specific IgG, in the absence (C) or presence of 20 μM forskolin (F).
Figure 8B:
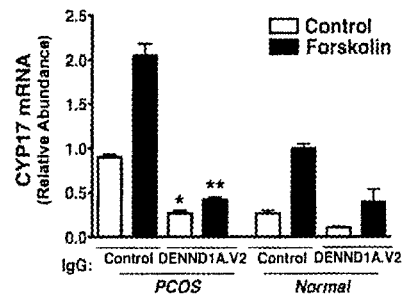

In this disclosure, it is demonstrated that antibody targeting of the 21 amino acid C-terminus of the DENND1A.V2 protein significantly reduces androgen biosynthesis and CYP17 and CYP11A1 mRNA PCOS theca cells (e.g., see FIG. 8A-B).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method.

Antibodies and methods for preparation of antibodies are well-known in the art. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

In one illustrative approach, a monoclonal antibody can be made by standard approaches using the polypeptide NTIATPATLHILQKSITHFAAKFPTRGWTSSSH (SEQ ID NO:5) that is located at the DENND1A.V2 C-terminus, or any immunogenic fragment of it. In an embodiment, a monoclonal antibody is made to a 21 amino acid sequence segment of SEQ ID NO: 5, consisting of the sequence QKSITHFAAKFPTRGWTSSSH (SEQ ID NO:6) or to one or more determinants within SEQ ID NO:6.

Antibodies of the present disclosure can recognize either a conformational epitope(s) and/or a linear epitope(s) present in the NTIATPATLHILQKSITHFAAKFPTRG WTSSSH (SEQ ID NO:5) sequence or QKSITHFAAKFP-TRGWTSSSH (SEQ ID NO:6).

In embodiments, the antibodies and antigen binding fragments specifically recognize at least one epitope present in at least about 4 contiguous amino acids of the 33 amino acid DENND1A.V2 C-terminal sequence, beginning and ending at any position within the 33 amino acid sequence. In embodiments, the epitope has at least about 4, 5, 6, or 7 contiguous amino acids present in the 33 amino acid DENND1A.V2 C-terminal sequence (SEQ ID NO: 5). The epitope can also be defined by longer sequences, for example up to about 12 amino acids (e.g. 8, 9, 10, 11, or 12 amino acids). Thus, the epitope can comprise or consist of up to any about 12 amino acid segment of the 33 amino acid DENND1A.V2 C-terminal sequence, or a longer segment. In embodiments, the antibody or antigen binding fragment is specific for an epitope that is partially or fully present in any of the following exemplary segments of the 33 amino acid DENND1A.V2 C-terminal sequence: NTIATPA (SEQ ID NO:7); TIATPAT (SEQ ID NO:8); IATPATL (SEQ ID NO:9); ATPATLH (SEQ ID NO:10); TPATLHI (SEQ ID NO:11); PATLHIL (SEQ ID NO:12); ATLHILQ (SEQ ID NO:13); TLHILQK (SEQ ID NO:14); LHILQKS (SEQ ID NO:15); HILQKSI (SEQ ID NO:16); ILQKSIT (SEQ ID NO:17); LQKSITH (SEQ ID NO:18); QKSITHF (SEQ ID NO:19); KSITHFA (SEQ ID NO:20); SITHFAA (SEQ ID NO:21); ITHFAAK (SEQ ID NO:22); THFAAKF (SEQ ID NO:23); HFAAKFP (SEQ ID NO:24); FAAKFPT (SEQ ID NO:25); AAKFPTR (SEQ ID NO:26); AKFPTRG (SEQ ID NO:27); KFPTRGW (SEQ ID NO:28); FPTRGWT (SEQ ID NO:29); PTRGWTS (SEQ ID NO:30); TRGWTSS (SEQ ID NO:31); RGWTSSS (SEQ ID NO:32); GWTSSSH (SEQ ID NO:33), and combinations thereof. In embodiments, the antibodies of this disclosure specifically recognize an epitope present in at least about 4 contiguous amino acids of the 21 amino acid sequence: QKSITHFAAKFPTRG-WTSSSH (SEQ ID NO:6) (e.g. segments comprising about 4, 5, 6, 7, 8, 9, 10, 11 or 12 consecutive amino acids, which are included in or include the group of 7 amino acid sequences disclosed above. For example, starting from SEQ ID NO:7, the following 4 contiguous amino acids may comprise an epitope that is recognized by the antibody: NTIA (SEQ ID NO:66), TIAT (SEQ ID NO:67), IATP (SEQ ID NO:68), and ATPA (SEQ ID NO:69). Additionally, these epitopes may be part of longer sequences. For example, starting from SEQ ID NO:66 the sequence XXNTIAX (SEQ ID NO:70) may comprise an epitope that is recognized by the antibody wherein X is any amino acid as described herein. In embodiments, the antibodies recognize an epitope with a sequence with at least about 65, 70, 75, 80, 85, 90, 95, 96, 97, 98 or 99% sequence identity to a sequence partially or fully present in SEQ ID NO:5. The disclosure includes structures (e.g. binding molecules such as antibodies or fragments thereof as described herein) that have at least one paratope that recognizes at least one of the foregoing amino acid segments, or at least two paratopes that recognize at least one of the foregoing segments.

An antibody or antigen-binding fragment of the invention specifically recognizes or binds a target epitope when it displays no more than 5% binding to other epitopes, and preferably displays no measurable binding to other epitopes, for example when measured by an enzyme-linked immunosorbent assay. An antibody or antigen-binding fragment does not specifically recognize or bind a target epitope if it displays more than 5% binding to other epitopes. Antibodies or antigen-binding fragments that bind non-specifically may still bind selectively, for example, an antibody may bind the target epitope as well as display non-specific binding to a few other epitopes.

Antibodies may be produced by various methods known in the art such as chemical peptide synthesis. In one approach, to make a monoclonal antibody, a DENND1A.V2 C-terminal polypeptide described herein is introduced into a laboratory animal, such as a mouse, over a series of administrations over a period of time spanning several weeks. Typically, splenocytes are isolated from the mouse spleen, and isolated B cells are obtained and fused with myeloma cells which have been immortalized using any suitable approach, such as electrofusion. The myeloma cells characteristically lack the hypoxanthine-guanine phosphoribosyl-transferase (HGPRT) gene and as a result are sensitive to HAT medium (hypoxanthine-aminopterin-thymidine medium). The fusions are generally exposed to the HAT medium for a period of time, such as from 10 to 14 days, during which a compound such as aminopterin is used to inhibit nucleotide synthesis, resulting in death of unfused cells and survival of B cell-myeloma hybrids (hybridomas) which have been immortalized and which produce antibodies. The cells are diluted to isolate single hybridomas in single wells of, for instance, a multi-well plate. The hybridomas are then screened to identify those that produce antibodies that specifically recognize the DENND1A.V2 C-terminus, and thus do not cross-react with DENND1A.V1 protein. Once suitable hybridomas are isolated the DNA encoding the secreted immunoglobulin (Ig) can be sequenced, and thus the amino acid sequence of the Ig can be determined. The complementarity determining regions (CDRs) of the Ig heavy and light chains can be determined and used to make synthetic versions of the antibodies made by the hybridomas, or to make antigen binding moieties as further described herein. Alternatively, the cell that produces the antibody can be cloned to produce identical daughter clones which will provide an ongoing source of monoclonal antibodies. When large amounts of antiserum is desired, larger animals, for example goat or sheep, may be used as the host species for antibody production.

Any antibody produced by a non-human mammal derived hybridoma can be modified to provide a chimeric, or partially or fully humanized form; and the present disclosure includes such modifications. In general, "humanized" forms of non-human (e.g., mice) antibodies are chimeric antibodies that contain a minimal sequence derived from the non-human antibody. Humanized antibodies are essentially human immunoglobulins (also called the "recipient" antibody) in which residues from a hypervariable region of the recipient are replaced by residues from a hypervariable region of a non-human species (also called a "donor" antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also can comprise at least a portion of an immunoglobulin constant region (Fc), typically that of a human immunoglobulin. For further details, see Jones et al., [27]; Riechmann et al., [28]; and Presta, [29].

Methods for humanizing non-human antibodies are well known in the art. Humanization of an antibody produced according to the present disclosure can be essentially performed following the method of Winter and co-workers by substituting mouse CDR sequences for the corresponding sequences of a human antibody, Jones et al [27]; Riechmann et al., [28]; and Verhoeyen et al., [30].

In another embodiment, the disclosure includes an antigen-binding or variable region fragment of an antibody described herein. Examples of suitable antibody fragments include Fab, Fab', F(ab')$_2$ and Fv fragments. Various techniques have been developed for the production of antibody fragments. Traditionally, these fragments were derived via proteolytic digestion of intact antibodies. However, these fragments can now be produced directly by recombinant host cells. For example, the antibody fragments can be isolated from antibody phage libraries as described below. Alternatively, Fab'-SH fragments can be directly recovered from bacterial expression systems and chemically coupled to form F(ab')$_2$ fragments.

In one embodiment, a library of proteins that have antigen binding regions can be screened to identify candidates that can be modified for therapeutic purposes according to this disclosure. For example, a phage display or other antibody library can be screened against a DENND1A.V2 C-terminal polypeptide described herein, and DENND1A.V2 C-terminal specific binding proteins can be identified. The CDR sequences of the light and heavy chains encoded by the phage DNA, or any other DNA that encodes the antigen binding regions, can be determined using techniques known to those skilled in the art. The CDR sequences can then be cloned into expression vectors to produce DENND1A.V2 C-terminal specific antibodies or DENND1A.V2 C-terminal specific fragments thereof as described above. Thus, in embodiments, the DENND1A.V2 C-terminal specific antibodies or DENND1A.V2 C-terminal specific fragments thereof as described above will be distinct from polypeptides in the library. In an embodiment, the DENND1A.V2 C-terminal specific antibodies or DENND1A.V2 C-terminal specific fragments thereof do not contain any phage/phagemid protein, including but not necessarily limited to bacteriophage coat protein(s). Newer approaches for generating antibodies or antigen binding fragments such as the non-limiting example of camel nanobodies are contemplated herein.

The invention also provides isolated nucleic acids encoding the anti-DENND1A.V2 antibodies, vectors and host cells comprising the nucleic acids, and recombinant techniques for the production of the antibodies. An isolated nucleic acid may be operably linked to a heterologous promoter. The present invention further provides isolated nucleic acid molecules and their complements that contain genetic sequences (genes) which encode an amino acid sequence with at least about 65, 70, 75, 80, 85, 90, 95, 96, 97, 98 or 99% sequence identity, with the protein/polypeptide sequences disclosed herein. Exemplary encoding nucleotide sequences are provided, but those of skill in the art will recognize that, due to the redundancy of the genetic code, other nucleotide sequences may also encode the same protein/polypeptide. For recombinant production of the antibody, the nucleic acid encoding the antibody is isolated and inserted into a replicable vector for further cloning (e.g. for amplification of the DNA) or for expression. DNA encoding the monoclonal antibody is readily isolated and sequenced using conventional procedures (for example, by using oligonucleotide probes that are capable of binding specifically to genes encoding the heavy and light chains of the antibody). Many vectors are available and known in the art, for example pIgG1-H and PIgG1-L, etc. The vector components generally include, but are not limited to, one or more of the following: a signal sequence, an origin of replication, one or more marker genes, an enhancer element, a promoter, and a transcription termination sequence.

The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Exemplary expression vectors include but are not limited to CMV or β-actin driven plasmids (i.e, pcDNA, pCM6, pDRIVE-β-act, etc).

Amino acid sequence modification(s) of the anti-DENND1A.V2 antibodies described herein are contemplated. For example, it may be desirable to improve the binding affinity and/or other biological properties of the antibody. Amino acid sequence variants of the anti-DENND1A.V2 antibody are prepared by introducing appropriate nucleotide changes into the anti-DENND1A.V2 antibody nucleic acid, or by peptide synthesis. Such modifications include, for example, deletions from, and/or insertions into and/or substitutions of, residues within the amino acid sequences of the anti-DENND1A.V2 antibody. Substitutions may be conservative or non-conservative. Any combination of deletion, insertion, and substitution is made to arrive at the final construct, provided that the final construct possesses the desired characteristics. The amino acid changes also may alter post-translational processing of the anti-DENND1A.V2 antibody, such as changing the number or position of glycosylation sites. In general, the amino acid sequences of such variants are at least about 50, 55, 60, 65, 70, 75, 80, 85, 90, 95, 96, 97, 98, or 99% identical to the sequence from which they are derived, or, for fragments, to a contiguous portion of a sequence of the same.

A useful method for identification of certain residues or regions of the anti-DENND1A.V2 antibody that are preferred locations for mutagenesis is called "alanine scanning mutagenesis". Here, a residue or group of target residues are identified (e g, charged residues such as Arg, Asp, His, Lys, and Glu) and replaced by a neutral or negatively charged amino acid (most preferably alanine or polyalanine) to affect the interaction of the amino acids with DENND1A antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed the anti-DENND1A.V2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-DENND1A.V2 antibody with an N terminal methionyl. Other insertional variants of the anti-DENND1A.V2 antibody molecule include the fusion to the N- or C-terminus of the anti-DENND1A.V2 antibody to an enzyme or a polypeptide which increases the serum half-life of the antibody Another type of variant is an amino acid substitution variant. These variants have at least one amino acid residue in the anti-DENND1A.V2 antibody molecule replaced by a different residue. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the anti-DENND1A.V2 antibody may be substituted, generally with serine, to improve the oxidative stability of the molecule and prevent aberrant crosslinking. For example, the two cysteines in the $V_H$ of SEQ ID NO:58 can be replaced with serine as follows: EVQLLESGGGLVQPGGSLRLSSAASGFTFSSYAM-SWVRQAPGKGLEWVSIIGTDGDDTN YADSVKGR-FTISRDNSKNTLYLQMNSLRAEDTAVYYSAKAE-ASFDYWGQGTLVTVSS (SEQ ID NO:71). Conversely, residues capable of forming disulfide bond(s) may be added to the antibody to improve its stability (particularly where the antibody is an antibody fragment such as an Fv fragment).

A particularly preferred type of substitutional variant involves substituting one or more hypervariable region residues of a parent antibody (for example, a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (for example, 6-7 sites) are mutated to generate all possible amino acid substitutions at each site. The phage-displayed variants are then screened for their biological activity (for example, binding affinity, appropriate effects on cellular function). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human DENND1A.V2. Such contact residues and neighboring residues are candidates for substitution according to the techniques elaborated herein. Once such variants are generated, the panel of variants is subjected to screening as described herein and antibodies with superior properties in one or more relevant assays may be selected for further development. Another type of amino acid variant of the antibody alters the original glycosylation pattern of the antibody By "altering" we mean deleting one or more residues capable of being glycosylated, or substituting one or more residues that are typically glycosylated or residues that are not susceptible to glycosylation and/or adding one or more amino acids that are glycosylation sites. For example, a N-linked glycosylation motif may be added in the $V_H$ of SEQ ID NO:58 as follows:

```
                                        (SEQ ID NO: 72)
EVQLLESGGGLVQPGGSLRLSSAASGFTFSSYAMSWVRQAPGKGLEWVSI

IGTDGDDTNYTDSVKGRFTISRDNSKNTLYLQMNSLRAEDTAVYYSAKAE

ASFDYWGQGTLVTVSS.
```

Embodiments of the invention relate to the treatment of DENND1A.V2 related disorders. The term "treatment" refers to both therapeutic treatment and prophylactic or preventative measures. Those in need of treatment include those already with the disorder as well as those in whom the disorder is to be prevented. Hence, the mammal to be treated herein may have been diagnosed as having the disorder or may be predisposed or susceptible (e.g. having a genetic predisposition) to the disorder.

The term "mammal" for purposes of treatment refers to any animal classified as a mammal, including humans, domestic and farm animals, and zoo, sports, or pet animals, such as dogs, horses, cats, cows, etc. Preferably, the mammal is human.

In some embodiments, the antibodies and/or antigen binding fragments of the invention are provided in a pharmaceutical formulation, which can contain components such as pharmaceutically acceptable carriers, excipients, stabilizers, etc. The antibodies and/or antigen binding fragments may also be combined with other drugs or therapies for the treatment of disorders correlated with expression of DENND1A.V2 mRNA or protein. For example, a monoclonal antibody against DENND1A.V2 may be administered for the treatment of PCOS in combination with hormonal therapy.

PCOS, type II diabetes associated with PCOS, and other disorders of females and males that is the direct result of expression of DENND1A.V2 which results in excess steroid biosynthesis are examples of a disease or disorder positively correlated with expression of DENND1A.V2 mRNA or protein. Affected tissues include, but are not limited to: ovarian, vascular smooth muscle, skeletal muscle, adipose tissue, and the endometrium.

The term "therapeutically effective amount" refers to an amount of a drug or pharmaceutical composition effective to treat a disease or disorder in a subject. In the case of PCOS or another DENND1A.V2 related disorder, the therapeutically effective amount of the antibody may reduce and/or prevent to some extent one or more of the symptoms associated with the disorder. For example, the amount of measurable testosterone (total and free), androstenedione, and dehydroepiandrosterone sulfate (DHEAS) in a biological sample obtained from a subject being treated as described herein (e.g. a blood sample) may decrease, e.g. at least about 10, 20, 30, 40, 50, 60, 70, 80 or 90% or more; and/or other symptoms may be ameliorated, e.g. ovulatory cycles will return, ovarian morphology may normalize, including disappearance of multiple follicular cysts, and hyperinsulinemia and insulin resistance may be diminished.

In further embodiments, the antibodies or antigen binding fragments thereof may be administered by any suitable means, including, but not limited to; subcutaneous, parenteral, vaginally, intraperitoneal, intrapulmonary, and intranasal. Parenteral infusions include intravenous, intramuscular, intraarterial, intraperitoneal, intralymphatic or subcutaneous administration. In addition, the monoclonal antibodies and/or antigen binding fragments thereof may be administered by pulse infusion, e.g., with declining doses. Methods of oral administration are also contemplated. Slow-release formulations may be used with modifications such as pegylation to extend the half-life of the pharmaceutical composition.

For the prevention or treatment of disease, the appropriate dosage of antibody will depend on the type of disease to be treated, the severity and course of the disease, whether the antibody is administered for preventive and/or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (for example, 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.5 mg/kg to about 10 mg/kg. Thus, one or more doses of about 0.5 mg/kg, 2 mg/kg, 4 mg/kg or 10 mg/kg (or any combination thereof) may be administered to the patient. Such doses may be administered intermittently, for example, every week or every three weeks. An initial higher loading dose, followed by one or more lower doses may be administered. An exemplary dosing regimen comprises administering an initial loading dose of about 4 mg/kg, followed by a weekly maintenance dose of about 2 mg/kg of the anti-DENND1A.V2 antibody. However, other dosage regimens may be useful. The progress of this therapy is easily monitored by conventional techniques and assays. Aside from administration of the antibody protein to the patient, the present application contemplates administration of the antibody by gene therapy. Such administration of nucleic acid encoding the antibody is encompassed by the expression "administering a therapeutically effective amount of an antibody".

Embodiments of the invention include polynucleotides encoding the antibodies and antigen binding fragments thereof, expression vectors comprising those polynucleotides, in vitro cell cultures wherein the cells comprise the expression vectors and express the antibodies or the antigen binding fragments thereof, and methods of using such expression vectors and cell cultures for making the antibodies and antigen binding fragments thereof. Other embodiments include RNAi, shRNA or other nucleotide containing compositions for the treatment of a disorder that is positively correlated with expression of DENND1A.V2.

There are two major approaches to delivering the nucleic acid (optionally contained in a vector) into the patient's cells, in vivo and ex vivo. For in vivo delivery the nucleic acid is injected directly into the patient, e.g. into the bloodstream or at the site where the antibody is required. For ex vivo treatment, the patient's cells are removed, the nucleic acid is introduced into these isolated cells and the modified cells are administered to the patient either directly or, for example, encapsulated within porous membranes which are re-implanted into the patient. There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

Exemplary in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Choi, for example). In some situations, it is desirable to provide the nucleic acid source with an agent that targets the target cells, such as an antibody specific for a cell surface membrane protein of the target cell, a ligand for a receptor on the target cell, etc. Where liposomes are employed, proteins which bind to a cell surface membrane protein associated with endocytosis may be used for targeting and/or to facilitate uptake; for example capsid proteins or fragments thereof tropic for a particular cell type, antibodies for proteins which undergo internalization in cycling, and proteins that target intracellular localization and enhance intracellular half-life.

In some embodiments, the targeted cells are theca cells and contacting the theca cells with the antibodies or antigen binding fragments described herein decreases androgen and/or progesterone biosynthesis in the theca cells and/or decreases CYP17A1 and/or CYP11A1 gene expression, as well as CYP17 and CYP11A1 mRNA and/or protein in the cells. These decreases reduce or prevent symptoms associated with overexpression of CYP17A1 and/or CYP11A1 gene regulation and CYP17 and/or CYP11A1 mRNA and/or protein; for example, excess androgen production. Exemplary symptoms of excess androgen production which may be lessened or resolved include but are not limited to: anovulation associated with hyperandrogenemia, hirsutism, ovarian morphology, infertility. In some embodiments, the antibodies or antigen binding fragments described herein reduce or prevent other phenotypes associated with PCOS, for example abnormal insulin signaling, insulin resistance in adipose, skeletal muscle, and endometrial tissue, abnormal FSH signaling in granulosa cells, and combinations thereof.

Embodiments of the invention also provide methods for altering signaling by cell surface receptors in cells having increased DENND1AV.2 expression as compared to control cells, The methods comprise a step of contacting such cells with an antibody or antigen binding fragment thereof as described herein, wherein the antibody or antigen binding fragment specifically recognizes DENND1A.V2 protein and does not specifically recognize DENND1A.V1 protein.

Articles of manufacture containing materials useful for the treatment of the disorders described herein are also provided. The articles of manufacture comprise a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). At least one active agent in the composition is an anti-DENND1A.V2 antibody or antibody fragment as described herein. The label or package insert indicates that the composition is used for treating the condition of choice and may provide instructions for use of the composition.

Anti-DENND1A.V2 antibodies are useful in diagnostic assays for DENND1A.V2 protein, for example, detecting its expression in specific cells, tissues, or serum. Aspects of the invention provide a method for diagnosis of a disorder that is positively correlated with expression of DENND1A.V2 mRNA and/or protein in a subject comprising contacting a biological sample from said subject with one or more antibodies comprising the amino acid sequence represented by SEQ ID NOs:53, 58, 59, 62, 63 or 65 and comparing the amount of DENND1A.V2 detected to a reference negative control. The disorder may be PCOS. A reference value may be obtained from samples from healthy, normal patients without the disease. If the measured value is greater than the normal reference value, then it can be concluded that the subject has the disease, and if the measured value is the same or less than the normal reference value, then it can be concluded that the subject does not have the disease. In certain embodiments, determining a statistically significant increase in DENND1A Variant 2 mRNA of at least 1.5 fold, and 2-3 fold of DENND1A Variant 2 protein in a sample as compared to a reference is a diagnosis of PCOS or aids in diagnosis of PCOS. In certain embodiments, the increase relative to a reference is at least 2.0, 3.0 or 4.0 fold, inclusive, and including all digits there between, and to the first decimal place. The reference value may also be a positive control value obtained from patients already diagnosed with the disease or disorder. In this case, if the measured value is the same or higher than the positive reference value, then it can be concluded that the subject has the disease. If the measured value is lower, for example at least a statistically significant 1.5 fold decrease, then it can be concluded that the subject does not have the disease. In some embodiments, both positive and negative reference values are used in diagnosis. If it is concluded that the subject has the disease, then one can continue with a step or method of treatment as described herein.

Examples of biological samples include, but are not limited to; urine, blood, plasma, serum, and saliva. In some embodiments, the biological sample is a biopsy or surgical specimen of the ovary, endometrium, adipose tissue, or skeletal muscle. For diagnostic applications, the antibody typically will be labeled with a detectable moiety. Numerous labels are available and known in the art (e.g. various fluorimetric or colorimetric tags). In another embodiment of the invention, the anti-DENND1A.V2 antibody need not be labeled, and the presence thereof can be detected using a labeled antibody which binds to the DENND1A.V2 antibody. The antibodies of the present invention may be employed in any known assay method, such as competitive binding assays, direct and indirect sandwich assays, and immunoprecipitation assays.

If DENNDIA Variant 2 mRNA is detected, this may be accomplished by a variety of techniques known in the art. Suitable techniques for determining the presence or absence or quantitating DENND1A Variant 2 mRNA include but are not limited to; hybridization of probes or primers directed to DENND1A Variant 2 mRNA, or by using various chip technologies, polynucleotide or oligonucleotide arrays, and combinations thereof. Thus, in various embodiments, probes to the DENND1A Variant 2 mRNA or a DNA equivalent of it can be arranged and/or fixed on a solid support.

DENND1A Variant 2 mRNA may be tested directly or may be amplified enzymatically in vitro by, for example, use of the polymerase chain reaction (PCR), Real-Time (RT) PCR, including quantitative real-time (qRT-PCR) PCR analysis, or any other in vitro amplification methods. For amplification reactions, primers can be designed which hybridize to and form a complex with DENND1A Variant 2 mRNA, and used to obtain nucleic acid amplification products (i.e., amplicons). Those skilled in the art will recognize how to design suitable primers and perform amplification and/or hybridization reactions in order to carry out various embodiments of the method of the invention. In general, the primers should be long enough to be useful in amplification reactions, and generally primers which are at least 12 bases in length are considered suitable for such purposes; but primers as short as 8 bases can be used depending on reaction conditions. The primers/probes used for detecting DENND1A Variant 2 RNA can comprise modifications, such as being conjugated to one or more detectable labels; such as fluorophores in the form of a reporter dye and/or a quenching moiety for use in reactions such as real time (RT)-PCR, which allow quantitation of DNA amplified from RNA, wherein the quantitation can be performed over time concurrent with the amplification. In one embodiment, the amplification reaction comprises at least one polynucleotide probe specific for DENNDIA Variant 2 mRNA, wherein the probe includes one terminal nucleotide modified to include a fluorescent tag, and the other terminal nucleotide modified to comprise a moiety that quenches fluorescence from the fluorescent tag. For instance, for use in qRT-PCR, such a probe can be designed so that it binds with specificity to a portion of DENNDA1 Variant 2 or its complement, that is between and does not overlap sequences to which two RT-PCR primers hybridize. Using this design, signal from the fluorescent tag will be quenched until the probe is degraded via exonuclease activity of the polymerase during amplification, at which point the fluorescent nucleotide will be separated from the quenching moiety and its signal will be detectable.

If desired, the determination of DENNDIA Variant 2 mRNA and/or protein can be compared to a reference value. The reference to which the Variant 2 mRNA and/or protein levels from the individual can be compared can be any suitable reference, examples of which include but are not limited to samples obtained from individuals who do not have the particular condition for which a diagnosis is sought, such as PCOS. Such references can include matched controls (i.e., matched for age, sex, or other demographics), a standardized curve(s), and/or experimentally designed controls such as known input RNA or protein used to normalize experimental data for qualitative or quantitative determination of the DENND1A Variant 2 from the sample for mass, molarity, concentration and the like. The reference level may also be depicted graphically as an area on a graph. In certain embodiments, determining Variant 2 mRNA and/or protein in a sample in an amount above a reference is a diagnosis of PCOS, or aids in a physician's diagnosis of PCOS. In certain embodiments, the reference is normal theca cells, which are compared to PCOS theca cells. In another embodiment, the reference is a sample that contains exosomes from an individual who does not have PCOS.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention will be further illustrated by the following examples. However, these examples and figures should not be interpreted in any way as limiting the scope of the present invention.

Example 1. Overexpression of DENND1A.V2 Produces a PCOS Theca Phenotype

Materials and Methods

Normal and PCOS Theca Cells. Human theca interna tissue was obtained from follicles of women undergoing hysterectomy, following informed consent under a protocol approved by the Institutional Review Board of The Pennsylvania State University College of Medicine. Individual follicles were dissected away from ovarian stroma, dissected, and dispersed with 0.05% collagenase I, 0.05% collagenase IA, and 0.01% deoxyribonuclease, in medium containing 10% fetal bovine serum (FBS), as previously described [31]. The isolated follicles were size-selected for diameters ranging from 3-5 mm so that theca cells derived from follicles of similar size from normal and PCOS subjects could be compared. Theca cells were cultured on fibronectin coated dishes utilizing previously described growth medium (1:1 mixture of Dulbecco's Eagles Medium (DME) and Hams F-12 medium containing 5% FBS, 5% horse serum (HS), 2% UltroSer G™, 20 nM insulin, 20 nM selenium, 1 µM vitamin E and antibiotics). Sera and growth factors were obtained from the following sources: FBS and DME/F12 (Irvine Scientific®, Irvine, Calif.): horse serum (Life Technologies, Grand Island, N.Y.); UltroSer G™ (Reactifs IBF, Villeneuve-la-Garenne, France): other compounds were purchased from Sigma® (St. Louis, Mo.). The cells were grown in reduced oxygen tension (5% $O_2$, 90% $N_2$, and 5% $CO_2$) and given supplemental antioxidants (vitamin E and selenium) to prevent oxidative damage.

The theca cell cultures utilized in these studies have been described and functionally characterized previously [15, 17, 32]. Experiments comparing PCOS and normal theca were performed utilizing $4^{th}$-passage (31-38 population doublings) theca cells isolated from size-matched follicles obtained from age-matched subjects. The use of fourth passage cells, propagated from frozen stocks of second passage cells in the media described above, allowed multiple experiments to be performed from the same patient population. For all studies, theca cell cultures obtained from at least 5 independent normal and 5 independent PCOS patients were examined. The passage conditions and split ratios for all normal and PCOS cells were identical.

The PCOS and normal ovarian tissue came from age-matched women, 38-40 years old. The diagnosis of PCOS was made according to NIH consensus guidelines [10], which include hyperandrogenemia, oligoovulation, polycystic ovaries, and the exclusion of 21-hydroxylase deficiency, Cushing's syndrome, and hyperprolactinemia. All of the PCOS theca cell preparations studied came from ovaries of women with fewer than six menses per year and elevated serum total testosterone or bioavailable testosterone levels, as previously described [15, 33]. Each of the PCOS ovaries contained multiple subcortical follicles of less than 10 mm in diameter. The control (normal) theca cell preparations came from ovaries of fertile women with normal menstrual histories, menstrual cycles of 21-35 days, and no clinical signs of hyperandrogenism. Neither PCOS nor normal subjects were receiving hormonal medications at the time of surgery. Indications for surgery were dysfunctional uterine bleeding, endometrial cancer, and/or pelvic pain.

Western Blot Analysis.

Fourth passage normal and PCOS theca cells were grown until subconfluent and transferred into serum free medium with and without forskolin for 24 hours. Following treatment theca cells were harvested in ice cold modified RIPA buffer (30 mM Tris, 150 mM NaCl, 50 mM Na F, 0.5 mM EDTA, 0.5% deoxycholic acid, 1.0% Nonident P-40, 0.1% SDS) containing 1 mM sodium orthovanadate, 0.1 mM phenymethylsufonyl fluoride, 1 mM dithiothreitol, 0.2 mM benzamidine, 1 µM microcystin, 1 ng/ml leupeptin, and 1 µg/ml pepstatin A. Protein concentration was determined using a BCA protein assay (Pierce, Rockford, Ill., USA). Whole cell lysates (35 µg/ln) were separated on a 10% SDS-PAGE, transferred to PVDF membrane, and Western analysis was performed as previously described [32][34].

Immunohistochemical Localization of DENND1A.V2.

Immunohistochemical analysis for DENND1A was performed on 4-5 µm thick sections of formalin-fixed, paraffin-embedded tissue on a Ventana Discovery XT stainer (Ventana Medical Systems, Tucson, Ariz.), using the Sigma DENND1A antibody found to be specific to DENND1A.V2. The staining protocol briefly consisted of incubation in the primary antibody for 30 minutes at 1:300 dilution followed by detection and visualization with Ventana OmniMap DAB anti-Rabbit detection kit (Ventana Medical Systems, Tucson, Ariz.). FFPE samples of adrenal cortex were used as a positive tissue control [34]. A color image of the DENND1A.V2 immunohistochemistry has been published by McAllister et. al [34].

Quantitative DENND1A. V1, DENND1A.V2, CYP17A1, and CYP11A1 Single Step Ultra-Fast qRT-PCR.

Quantitation of DENND1A. V1 and V.2, CYP17A1, and CYP11A1 mRNA abundance was determined using the Single Step Brilliant™ III Ultra Fast qRT-PCR Reagents (Agilent) using 50-100 ng total RNA/tube, and 200 nM final concentration of each forward and reverse primers, and 100 nM probe. The specific primer and probe sequences used are provided in detail below. The "ZEN" moiety is shown as in the probe at an illustrative location but can be positioned elsewhere in the probe, as desired. The gene specific one step PCR was carried out in duplicate for each mRNA sample and for a series of dilutions in an Mx3000p Thermocycler system (Stratagene) according to manufacturer's instructions for this instrument. An arbitrary value of theca RNA template was assigned to each serial dilution (ie, 1000, 300, 100, 30, 10, 3, 1, 0.3, 0.1 ng) and plotted against the Ct value (y-axis=Ct; x-axis=value, log scale) to generate a standard curve. Each unknown was assigned an arbitrary value based on the slope and y-intercept of the standard curve. The same process was carried out for TATA-box binding protein (TBP) in order to use TBP values for normalization of each reaction. The mean target value for each unknown was divided by the mean TBP value for each unknown to generate a normalized value for the target for each sample [34].

Primer and Probe Sets

The DENND1A Variant 2 specific mRNA Primer and Probe set[25] was specific to the 3'UTR, Forward Primer (5' GGGCTGACTTCGGAGTGTGT 3') (SEQ ID NO:34), Reverse Primer (5' GGG CTG ACT TCG GAG TGT GT3) (SEQ ID NO:35), Probe (5'/56-FAM/CCAAAGAGC/ZEN/CGG TGT CTG ATA ATC CCA/3iA3AbkFQ/–3) (SEQ ID NO:36).

Second Confirmatory DENND1A Variant 2 specific mRNA Primer and Probe set was specific to the 33aa 3'CDS Forward Primer (5' TCCACATGTTGTTAAGA GACCAAAG 3') (SEQ ID NO:37), Reverse Primer (5' CCGCAAAATGGGTAATGCTT 3') (SEQ ID NO:38), Probe (5'/56-FAM/AGCCCTGAG/ZEN/CAAAACACCATTG-CAA/3iA3AbkFQ/–3') (SEQ ID NO:39).

The DENND1A Variant 1 specific mRNA Primer and Probe set Forward Primer (5'GGATTCATTTCCATAAAC-CAAGTTAAAG3') (SEQ ID NO:40), Reverse Primer (5'CACAATTTCCTGCGTGTCTCA3') (SEQ ID NO:41), Probe (5'/56-FAM/ATGGCCCGA/ZENCCATTT AAGAAAACAACCA/#IA3BkFQ/–3) (SEQ ID NO:42)

The CYP17 mRNA Primer and Probe set. Forward primer (5'-GGCCTCAAA TGGCAAC TCTAGA-3') (SEQ ID NO:43), Reverse Primer (5'-CTTCTGATCGCCATCCTT-GAA-3') (SEQ ID NO:44), Probe(5' 6-FAM-TCGCGTC-CAACAACCGTAAGGGTATC-3' BHQ-1) (SEQ ID NO:45)

The CYP11A1 mRNA Primer and Probe set. Forward primer (5'GAGGGAGACGGGCACACA-3') (SEQ ID NO:46), Reverse Primer (5'-TGACATAAA CCGACTC-CACGTT-3') (SEQ ID NO:47), Probe(5' 6-FAM-TCCAC-CTTCACCATGTCCAGAATTTCCA-3' BHQ-1) (SEQ ID NO:48)

The TATA-box binding protein (TBP) mRNA Primer and Probe set. TBP was also determined for each cDNA sample for normalization. Forward Primer (5'-CACGGC ACT-GATTTTCAGTTC-3') (SEQ ID NO:49), Reverse Primer (5'-TCTTGCTGCCAGTCTGGACT-3') (SEQ ID NO:50), Probe (5' JOE-TGTGCACAGGAGCCAAGAGTGAAGA-3' BHQ-1) (SEQ ID NO:51).

Quantitation of Steroid Biosynthesis. ELISAs for dehyroepiandrosterone (DHEA), 17-hydroxyprogesterone (17OHP4), testosterone (T), and progesterone (P4) were performed without organic solvent extraction using kits from DRG International, Inc. (Springfield, N.J.) as described by the manufacturer's protocol, and normalized by cell count.

Exosomal RNA Extraction and Purification. Mid-day urine samples were obtained from normal women and women with PCOS, using the same clinical criteria described above for normal and PCOS theca cells, following informed consent under an IRB protocol approved by the Institutional Review Board of The Pennsylvania State University College of Medicine. The urine samples are collected and placed at 4° C. until processed, then aliquoted into 15 mL tubes and are centrifuged in a swing bucket in a Sorvall Super T21 Table Top Centrifuge at 300 g at 4° C. for 10 minutes to remove particulate matter. The supernatant is then serially centrifuged at 2000 g at 4° C. for 10 minutes to clear cellular debris, and the supernatant is transferred to a 17×100 mm culture tube and centrifuged at 12,000 g at 4° C. for 30 minutes using a floor Beckman Coulter Avanti® J-E Centrifuge. This final cleared supernatant is frozen at −80° C., and is extracted using a modified protocol of the "Urine Exosome RNA Isolation Kit" from Norgen® (Thorold, CAN). The resulting RNA is quantified using a Nanodrop. DENND1A.V2 mRNA was then quantitated by qRT-PCR, and normalized using 5S mRNA abundance [34].

Replication-Deficient Adenovirus Infections.

For these studies, DENND1A.V2 adenovirus (hDENND1A.V2-pADenoG) was obtained from Applied Biological Materials, Inc. (Vancouver, BC) that was constructed by cloning DENND1A.V2 from pCMV6-XL4 plasmid encoding the DENND1A.V2 into pADenoG, from Origene (Rockville, Md.)[34]. Control empty NULL non-expressing adenovirus (pAdenoG Null) also obtained from Applied Biological Materials, Inc. (Vancouver, BC) [35-37]. These recombinant adenoviruses were propagated and expanded in HEK293T monolayer cells, purified using a Virabind™ Adenovirus Miniprep Kit, (Cell Biolabs, Inc, San Diego, Calif.), and titered by QuickTiter Adenovirus Titer Elisa Kit, (Cell Biolabs, Inc., San Diego, Calif.). Both the DENND1A.V2 or Control empty NULL non-expressing adenovirus (pAdenoG Null) were used to infect normal theca cells as previously described [34] [38]. Adenoviral infections involved growing fourth passage theca cells to 75% confluence, rinsing the cells with phosphate buffered saline, and layering of the adenovirus on the cells in 50% of the normal treatment volume of serum free medium for 60 min. Subsequently, the cells were cultured in serum-free media with and without treatment as indicated.

Transient Transfection of Normal and PCOS Theca Cells.

Human theca cells isolated from normal cycling women and women with PCOS were transfected as previously described [17, 22, 39]. One hour prior to transfection, the cells were transferred into DME high-glucose medium containing 20 mmol/L HEPES and 2% heat-inactivated calf serum (Atlanta Biologicals, Inc., Atlanta, Ga.) and moved to a 3% $CO_2$, 95% ambient air, 37° C. incubator. The calcium phosphate precipitate contained 2 µg/dish of luciferase plasmid, and 0.1 µg/dish of an expression vector for β-galactosidase, pSVβ-gal (Promega, Madison, Wis.) for each 30 mm well. Following transfection, the cells were rinsed with 15% glycerol/HBSS followed by PBS, and treated in transfection media containing vehicle or 10 µM forskolin for 48 h. Cells were harvested with trypsin, pelleted, and resuspended in reporter lysis buffer (Promega). Luciferase activity was determined with the Luciferase Assay System (Promega) on a Sirius Luminometer (Zylux Corp., Oak Ridge, Tenn.). β-Galactosidase activity was measured by the chemiluminescent assay Galacto-Light Plus™ (Tropix, Bedford, Mass.) and utilized for normalization of transfection efficiency. Transfections were performed in triplicate in theca cells isolated from 4 or more independent normal control patients, and 4 or more independent PCOS patients unless otherwise noted in the text of this Example.

Statistical Analysis.

Data are presented and described in this Example as the mean±SEM performed triplicate. The results from qRT-PCR, steroid, and transfection analysis were collected from individual patients and ANOVA was performed using Prism 5.0c (GraphPad Software, San Diego, Calif.). P values were determined by the Boniferri method for multiple comparisons when significant differences were indicated by ANOVA [34].

DNA Extraction.

DNA was extracted from theca cell cultures isolated and propagated from independent normal cycling (n=6) and PCOS women (n=6). The frozen theca cell culture plates were retrieved from −80° C. and 1 mL of lysis solution, containing 0.10 µL 1M Tris-HCl pH 8.0 (Invitrogen, Carlsbad, Calif.), 0.01 µL 0.5M EDTA pH 8.0 (Promega, Madison, Wis.), 0.02 μL 10% SDS (Fisher Biotech, Fair Lawn, N.J.), 0.04 μL 5M NaCl (Promega, Madison, Wis.), 0.01 μL 10 mg/mL Proteinase K (Life Technologies™, Carlsbad, Calif.), and 0.82 mL of water, was added to each plate[34]. Plates were scraped to retrieve cells in solution. The lysis solution containing the cells was transferred to 1.5 mL microcentrifuge tubes, which were incubated in a tube rotator at 55° C. overnight. Samples were centrifuged at independent normal cycling (n=6) and PCOS women (n=6): The table lists the variants along with rs identifiers for snps, previously listed and identified in dbSNPs, chromosome locations, position/function of the variant in the gene, reference allele in human reference genome Hg19. The minor allele frequency of the snp in our sample set (6 Normal, 6 PCOS) were calculated and compared with the allele frequency in European American population if present[34].

TABLE 1

DENND1A variants identified by Whole Exome Sequence Analysis of DNA extracted from independent normal cycling and PCOS women.

| Gene DENND1A SNP | Location Chr | Position | Function | Ref Allele | # Samples with SNP | Calculated minor allele freq Normal | PCOS | EA |
|---|---|---|---|---|---|---|---|---|
| rs3739837 | 9 | 126143662 | utr-3 | G | 1 N, 1 PCOS | A (0.083) | A (0.083) | A (0.1109) |
| rs2491348 | 9 | 126144746 | Synonymous-coding | T | 6 N, 6 PCOS | C (1.0) | C (1.0) | T (0.0003) |
| rs2808409 | 9 | 126144758 | Synonymous-coding | T | 6 N, 6 PCOS | C (1.0) | C (1.0) | ABSENT |
| rs2808411 | 9 | 126146197 | Intron | C | 6 N, 6 PCOS | G (1.0) | G (1.0) | C (0.082) |
| rs10739631 | 9 | 126164562 | Intron | T | 6 N, 6 PCOS | C (1.0) | C (1.0) | ABSENT |
| rs7872778 | 9 | 126201672 | Intron | G | 1 N, 0 PCOS | A (0.083) | Absent | ABSENT |
| rs62581072 | 9 | 126201742 | Intron | G | 0 N, 1 PCOS | Absent | A (0.083) | ABSENT |
| rs10739633 | 9 | 126202551 | Intron | A | 5 N, 5 PCOS | C (0.75) | C (0.75) | ABSENT |
| rs3829851 | 9 | 126219706 | Synonymous-coding | A | 1 N, 0 PCOS | G (0.083) | Absent | G (0.055) |
| snp4115 | 9 | 126219742 | Intron | C | 0 N, 1 PCOS | Absent | 1 (0.083) | ABSENT |
| snp3842 | 9 | 126220063 | Intron | G | 0 N, 1 PCOS | Absent | T (0.083) | ABSENT |
| rs61736953 | 9 | 126220114 | Synonymous-coding | C | 1 N, 2 PCOS | T (0.083) | T (0.166) | T(0.0884) |
| rs12377595 | 9 | 126439100 | Intron | T | 2 N, 3 PCOS | G (0.166) | G (0.33) | G (0.2490) |
| rs9785285 | 9 | 126520068 | Synonymous-coding | T | 3 N, 2 PCOS | C (0.33) | C (0.166) | C (0.2123) |
| rs41274356 | 9 | 126531724 | Intron | T | 1 N, 0 PCOS | C (0.083) | Absent | C (0.0239) |
| rs1778890 | 9 | 126531755 | Intron | T | 3 N, 2 PCOS | C (0.33) | C (0.166) | C (0.2148) |
| snp3895 | 9 | 126554844 | Intron | A | 0 N, 1 PCOS | Absent | G (0.083) | ABSENT |
| rs670028 | 9 | 126641091 | Intron | A | 2 N, 0 PCOS | G (0.25) | Absent | ABSENT |

12,000 rpm for 5 min at room temperature. Approximately 400 μL of sample was transferred to 1.5 mL microcentrifuge tube containing 500 μL of isopropyl alcohol and inverted several times to precipitate DNA. DNA was washed twice with 70% EtOH and transferred to microcentrifuge tube containing 400 μL of 1× Tris-EDTA pH 7.4 (Fisher Bior-Reagents, Fair Lawn, N.J.). Tubes were incubated in a tube rotator at 55° C. for 2 h to dissolve DNA in solution[34].

Whole Exome Sequencing.

The DNA samples were subjected to whole exome sequencing at 100 millions reads, at 100× coverage using the Agilent SureSelect 51M capture kit with Illumina HiSeq 2000 sequencing, in conjunction with BGI Americas (Cambridge, Mass.).

Exome Sequence Analysis.

Sequence reads obtained were aligned to the reference genome (Human hg19) by BGI [34]. Variant calling and summary of data production was performed by BGI. Visualization of data and identification of called variants was done using the IGV (Integrative Genomic Viewer) software [40]. Only those variants with support numbers>15 (count of the uniquely mapped base) for the minor allele were selected from the normal and PCOS theca cell samples for further analysis. SNPs in DENND1A were identified and their minor allele frequencies were calculated. Data is presented in Table 1[34].

Table 1 shows the DENND1A variants identified by Whole Exome Sequence Analysis of DNA extracted from Exome Data Comparison.

Minor allele frequencies of the DENND1A variants identified by our WES analysis were compared to the allele frequencies of these variants in the population using the online database—Exome 6500 [34]. Comparisons were made with the European American population frequencies since the theca cell samples in this study were extracted from patients of Western European descent [34].

Results

DENND1A.V2 Protein Expression is Increased in PCOS Theca Cells.

Figure 1B:
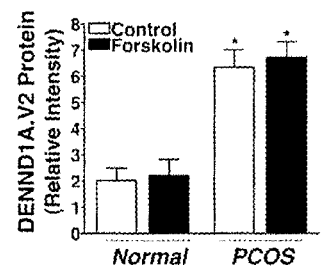
Figure 1C:
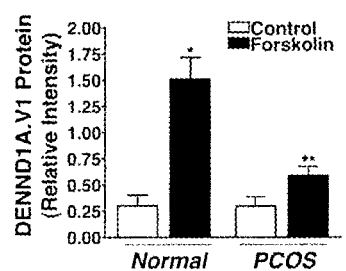

To examine whether the alternatively spliced forms of DENND1A are differentially expressed in normal and PCOS theca cells[34], Western Blot analysis was performed on whole cell extracts from theca cells isolated from normal and PCOS women, that were grown until subconfluent and transferred into serum free medium treated with and without 20 μM forskolin for 24 h. An intermediate N-terminal DENND1A antibody (Sigma) was utilized, and we expected bands at approximately 112 kD, corresponding, to DENND1A.V1, and a 62 kD band, corresponding to DENND1A.V2. As shown in FIG. 1A, representative Western Blot analysis demonstrated increased 62 kD DENND1A.V2 in PCOS theca cells treated under both basal and forskolin-stimulated conditions compared to normal theca cells. However, the 112 kD DENND1A.V1 was not significantly increased in PCOS theca cells. In FIG. 1B, cumulative analysis of whole cell lysates harvested from theca cells isolated from 5 independent normal and 5 independent PCOS subjects, demonstrated that DENND1A.V2 protein was increased (*, P<0.01) in PCOS theca cells as compared to normal theca cells under both control and forskolin-stimulated conditions. Forskolin treatment did not appear to affect DENND1A.V2 protein accumulation in normal or PCOS theca cells. In contrast, cumulative analysis of DENND1A.V1 in normal and PCOS theca cells, showed that DENND1A.V1 protein level was increased (*, P<0.01) by forskolin treatment in normal cells (FIG. 1C). In addition, in forskolin-stimulated PCOS theca cells, DENND1A.V1 was significantly reduced compared to normal cells. The ratio of DENND1A.V2/V1 protein was increased (**, P<0.01) in PCOS theca cells under control and forskolin stimulated conditions (FIG. 1D)[34]. Similar results were obtained in Western analyses performed using Abcam antibody specific for the N-terminal and Sigma antibody for intra-peptide sequence of DENND1A. DENND1A Western data were quantitated and normalized by total mTOR which is not significantly different in normal and PCOS theca cells, nor regulated by forskolin treatment. Actin and GAPDH cannot be utilized to normalize Westerns as they are regulated by forskolin in theca cells, and are differentially expressed in normal and PCOS cells.

Figure 1D:
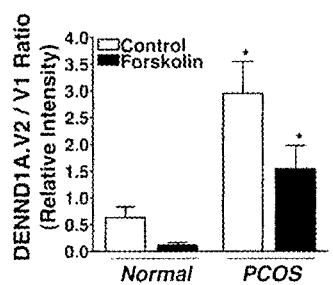
Figure 1E:
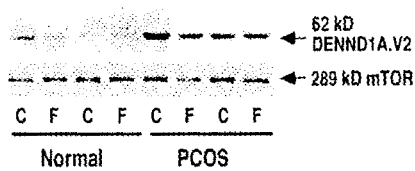
Figure 1F:
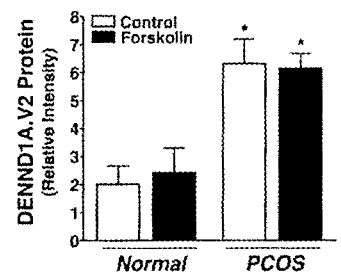

Western analyses were also performed to evaluate the efficacy of a rabbit polyclonal antibody, generated against the 21 amino acid peptide (QKSITHFAAKFPTRG-WTSSSH)(SEQ NO:6) that is specific to DENND1A.V2. Western Blot analysis was performed using whole cell extracts from theca cells isolated and propagated from normal and PCOS women, that were treated with and without 20 µM forskolin for 24 h in serum free media. As shown in FIG. 1E, representative Western Blot analysis demonstrated an increase in 62 kD DENND1A.V2 in PCOS theca cells treated under both basal and forskolin-stimulated conditions. In these experiments, protein loading was normalized by total mTOR. These data are in agreement with parallel Western blot analyses presented in FIG. 1A with the N-terminal DENND1A antibody. As shown in FIG. 1F, representative Western Blot analysis demonstrated increased 62 kD DENND1A.V2 in PCOS theca cells treated under both basal and forskolin stimulated conditions. In FIG. 1F, cumulative analysis of whole cell lysates harvested from theca cells isolated from 4 independent normal and 4 independent PCOS patients, demonstrated that DENND1A.V2 protein is significantly increased in PCOS theca cells as compared to normal theca cells under both control and forskolin-stimulated conditions (*, P<0.01). Forskolin treatment did not appear to affect DENND1A.V2 protein accumulation in normal or PCOS theca cells.

DENND1A.V2 Immunohistochemical Staining is Increased in the Ovarian Theca Compartment.

Figures 2A, 2B:
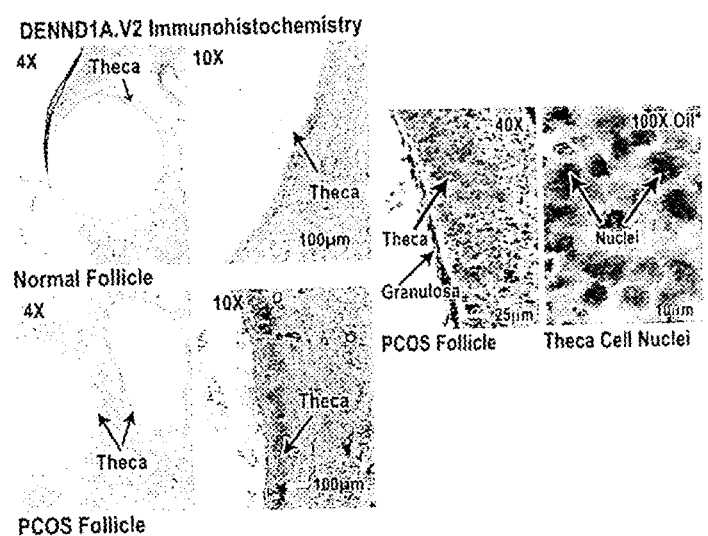
FIG. 2A-B. Immunohistochemical localization of DENND1A.V2 in normal cycling and PCOS ovary.

To further examine the localization of DENND1A.V2 in the ovary, the paraffin embedded blocks of ovarian tissue obtained from the normal cycling and PCOS patient populations, and an antibody specific to DENND1A.V2 was utilized[34]. As shown in FIG. 2A immuno-staining was prominent in the theca compartment of the ovary (4×), and increased in PCOS theca as compared to theca cells in normal ovaries (10×). In FIG. 2B, DENND1A.V2 staining in PCOS theca and granulosa cells is shown (40×). Staining is primarily in the PCOS theca nuclei, cytoplasm, and cell membranes as shown (100×, Oil mag) in FIG. 2B.

DENND1A.V2 mRNA Abundance is Increased in PCOS Theca Cells Compared to Normal Theca Cells, and Correlates with Increased Androgen Production by PCOS Theca Cells.

Figure 3A:
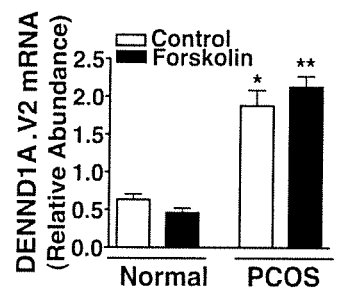
FIG. 3A-B. DENND1A.V2 mRNA abundance is increased in PCOS theca cells, and is correlated with increased androgen production. DENND1A.V2 (FIG. 3A) mRNA abundance was compared in theca cells propagated from 6 individual normal and 6 individual PCOS women that were treated in the absence (C) and presence (F) of 20 µM forskolin for 16 h, using qRT-PCR. DENND1A.V2 mRNA was significantly increased under basal (*, $P<0.05$) and forskolin (**, $P<0.01$) stimulated conditions in PCOS theca cells, as compared to normal cells (FIG. 3B). Both control (C) and forskolin (F)-stimulated DHEA accumulation from the 6 normal and 6 PCOS women's theca cell preparations were compared with DENND1A.V2 mRNA under the same conditions (FIG. 3B).
Figure 3B:
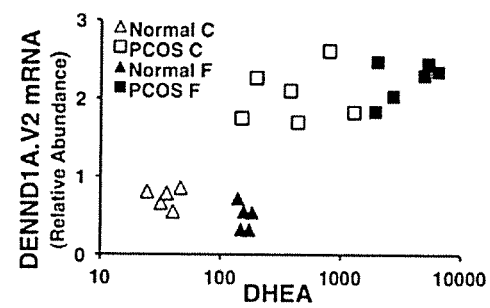

The abundance of DENND1A.V2 mRNA was examined in theca cells isolated from 6 normal and 6 PCOS patients treated with and without 20 µM forskolin (FIG. 3A), quantitated by QRT-PCR analysis, and normalized using TATA box binding protein (TBP) mRNA. DENND1A.V2 mRNA was significantly increased under basal and forskolin-stimulated conditions in PCOS theca cells, as compared to normal cells. There was no significant increase in DENND1A.V2 mRNA accumulation in response to forskolin stimulation. To examine whether DENND1A.V2 mRNA was associated with increased androgen biosynthesis, we examined DHEA accumulation in the matched 6 normal and 6 PCOS theca cell preparations under the same conditions. As shown in FIG. 3B, normal theca cells with lower DHEA synthesis have reduced DENND1A.V2 mRNA, whereas the increase in basal and forskolin stimulated DHEA production in PCOS theca cells is associated with increased DENND1A.V2 mRNA abundance [34].

Urine Exosomal DENND1A.V2 mRNA is Increased in PCOS Women.

Figure 4:
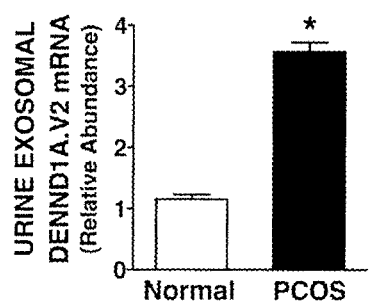
FIG. 4. DENND1A Variant 2 mRNA is increased in urine exosomes isolated from PCOS women as compared to normal women. Comparison of DENND1A.V2 RNA accumulation in exosomal mRNA purified and isolated from mid-day urine obtained from isolated from 5 normal cycling and 6 PCOS women (*, $P<0.001$) using real-time qPCR analysis.

Exosomes are small nucleic acid rich vesicles that are shed into blood and urine, and provide a stable source of RNA for use in personalized medicine and clinical diagnostics. Thus, to examine whether increased DENND1A.V2 in PCOS theca cells reflects corresponding increases in systemic DENND1A.V2 mRNA accumulation in PCOS women, exosomal mRNA isolated from mid-day urine samples from multiple normal cycling and well-characterized PCOS women was examined. Urine exosomal mRNA was isolated and prepared, as described in Materials and Methods, from mid-day urine samples from normal cycling and PCOS women. As shown in FIG. 4, and in agreement with the qRT-PCR in PCOS theca cells, DENND1A.V2 mRNA is significantly increased in urine exosomes isolated from PCOS, as compared to normal cycling women [34].

Forced Expression of DENND1A.V2 Increases Normal Theca Cell Steroidogenesis.

Figure 5A:
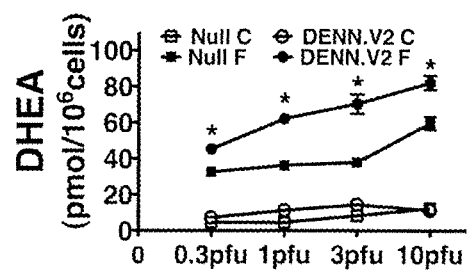
FIG. 5A-E. Forced expression of DENND1A.V2 in normal theca cells results in augmented androgen and progestin production. To examine the effects of forced expression DENND1A.V2 on androgen biosynthesis in normal theca cells, DHEA production by representative normal theca cells infected with 0.3, 1.0, 3.0, and 10 pfu/cell of either empty (Null) or DENND1A.V2 adenovirus, treated in the absence (C) or presence (F) of 20 µM forskolin for 72 h is presented in FIG. 5A. As shown, DENND1A.V2 adenoviral infection and forced DENND1A.V2 expression, increases forskolin-stimulated DHEA production in normal theca cells, compared to control Null adenovirus. In subsequent studies normal theca cells were infected with either 3 pfu/cell of DENND1A.V2, or control, Null adenovirus and treated in the absence (C) or presence of (F) of 20 µM forskolin for 72 h. DHEA (FIG. 5B), 17OHP4 (FIG. 5C), T (FIG. 5D) and Progesterone (FIG. 5E), were then measured and normalized by cell count. As shown, DENND1A.V2 adenovirus infection significantly increased basal 17OHP4 (FIG. 5C; *, $P<0.01$), T (FIG. 5D; *, $P<0.05$), and P4 (FIG. 5E; *, $P<0.05$) accumulation compared with control Null adenovirus. In addition, DENND1A.V2 adenovirus infection significantly increased forskolin-stimulated DHEA (FIG. 5B; *, $P<0.001$), 17OHP4 (FIG. 5C; *, $P<0.001$), and P4 (FIG. 5E; *, $P<0.001$) compared with control Null adenovirus. Thus forced expression of DENND1A.V2 in normal theca cells augments androgen and progesterone biosynthesis, and promotes a PCOS phenotype.
Figure 5B:
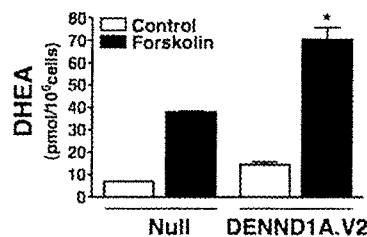
Figure 5C:
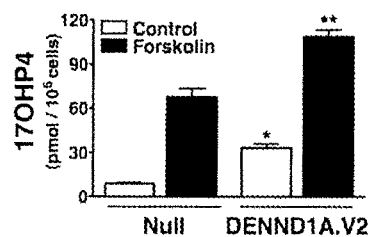
Figure 5D:
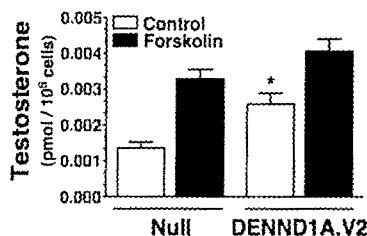
Figure 5E:
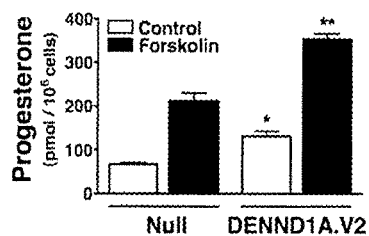

An adenovirus expressing human DENND1A.V2 was utilized to test the hypothesis that increased expression of DENND1A.V2 converts normal theca cells to a PCOS phenotype of increased androgen and progesterone production. In these experiments, normal theca cells were infected with 0.3, 1.0, 3.0, and 10 pfu/cell of either empty (Null-pAdenoG) or DENND1A.V2 expressing (hDENND1A.V2-pADenoG) adenovirus, treated with or without 20 µM forskolin in serum free medium. Following 72 h of treatment, DHEA in the media was quantitated. Infection with all doses of DENND1A.V2 adenovirus significantly increased forskolin-stimulated DHEA production compared with control adenovirus (FIG. 5A). In subsequent experiments, the effects of infection of theca cells from several individual normal women with 3.0 pfu of control adenovirus or adenovirus expressing DENND1A.V2 on DHEA (FIG. 5B), 17OHP4 (FIG. 5C), T (FIG. 5D), and P4 (FIG. 5E) was investigated. DENND1A.V2 adenovirus infection significantly increased basal 17OHP4, T, and P4 accumulation compared with control adenovirus. In addition, DENND1A.V2 adenovirus infection significantly increased forskolin-stimulated DHEA, 17OHP4, and P4 compared with control adenovirus. For these experiments Western analysis confirmed that DENND1A.V2 protein was increased following forced expression (data not shown) [34]. Thus, forced expression of DENND1A.V2 in normal theca cells, converted the cells to a PCOS phenotype of increased androgen and progestin biosynthesis [15, 16, 34].

Forced Expression of DENND1A.V2 Increases CYP17A1 and CYP11A1 Gene Expression in Normal Theca Cells.

Figure 6A:
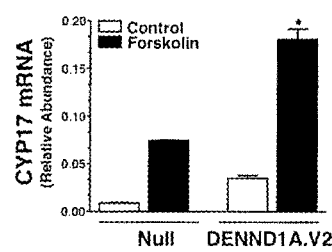
FIG. 6A-D. Forced expression of DENND1A.V2 in normal theca cells results in augmented CYP17 and CYP11A1 mRNA accumulation, as well as CYP17A1 and CYP11A1 promoter regulation. To examine the effects of DENND1A.V2 on CYP17 and CYP11A1 mRNA accumulation, normal theca cells were infected either 3 pfu/cell of DENND1A.V2, or control, Null adenovirus and treated in the absence (C; control) or presence (F; forskolin) of 20 µM forskolin for 16 h. Following RNA isolation, CYP17 and CYP11A1 mRNA was quantitated by qRT-PCR and normalized by TBP mRNA. As shown, forced expression of DENND1A.V2 in normal theca cells, significantly increased forskolin-stimulated CYP17 mRNA (FIG. 6A; *, $P<0.01$) and CYP11A1 mRNA (FIG. 6B; *, $P<0.05$) accumulation. To examine the effects of DENND1A.V2 on CYP17A1 transcription, normal theca cells were transfected with a CYP17A1 promoter gene plasmid (−770 CYP17A1/LUC), and infected with DENND1A V2 or Null adenovirus (FIG. 6C).
Figure 6B:
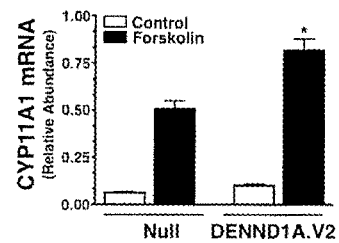

To examine the effects of DENND1A.V2 expression on CYP17 and CYP11A1 mRNA accumulation, cultures of $4^{th}$ passage normal theca cells were infected with 3 pfu DENND1A.V2 adenovirus, or Null adenovirus, and treated with or without 20 μM forskolin for 16 h. Following treatment, RNA was harvested, and CYP17 and CYP11A1 mRNA abundance was quantitated and normalized by TBP abundance. Both CYP17A1 mRNA (FIG. 6A) and CYP11A1 mRNA (FIG. 6B) accumulation were significantly increased following 3 pfu/cell DENND1A.V2 infection under forskolin-stimulated conditions, as compared to infection with control adenovirus. These finding were also confirmed using transfection of normal theca cells with a DENND1A.V2 expression plasmid (DENND1A.V2/pCMV-XL4) obtained from Origene (Rockville, Md.)[34], as well as following DENND1A.V2 lentiviral particle infection (data not shown).

Figure 6C:
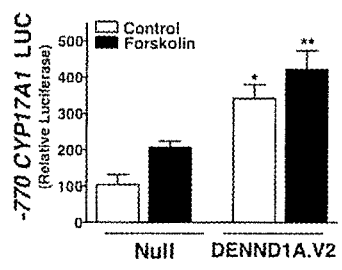

To examine the effects of DENND1A.V2 on CYP17A1 transcription, normal theca cells were transfected with pG13 luciferase reporter plasmid containing −770/+44 of the 5'-flanking regions of the human CYP17A1 gene (−770 CYP17A1/LUC) using the calcium phosphate method [17, 22, 34]. Following transfection the cells were infected with the DENND1A.V2 adenovirus or control adenovirus for 1 h, and treated with serum-free medium with and without 20 μM forskolin, an activator of adenylate cyclase. 24 h thereafter luciferase activity was determined. Transfections were performed in triplicate, normalized for transfection efficiency using β-galactosidase. FIG. 6C shows that 3 pfu/cell DENND1A.V2 adenovirus infection increases both basal and forskolin-stimulated −770CYPI7A1/LUC promoter activity as compared to control adenovirus [34].

Figure 6D:
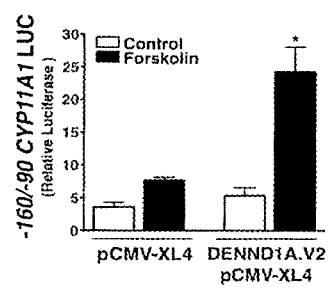

A CYP11A1 pG13 reporter construct containing the −160/−90 bp element of the proximal CYP11A1 promoter (−160/−90 CYP11A1/LUC) which confers increased CYP11A1 expression in PCOS theca cells was used to examine the effects of DENND1A.V2 on CYP11A1 transcription in theca cells. Normal theca cells were transfected with the −160/−90 CYP11A1/LUC plasmid with a DENND1A.V2/pCMV-XL4 or empty pCMV-XL4. 48 h following transfection the cells were harvested and luciferase was measured. As shown in FIG. 6D, DENND1A.V2 increases forskolin-stimulated −160/−90 CYP11A1/LUC promoter activity as compared to empty plasmid. Collectively, these data suggest that the increased theca cell steroidogenesis resulting from augmented DENND1A.V2 expression is due at least in part to transcriptional activation of the CYP17A1 and CYP11A1 genes [34].

Knock-down of DENND1A.V2 mRNA in PCOS Theca Cells Reduces CYP17A1 and CYP11A1 Expression, Androgen and Progesterone Production.

Figure 7A:
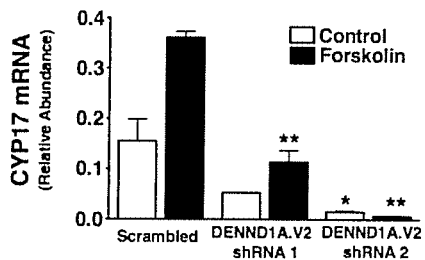
FIG. 7A-F. Knock-down of DENND1A.V2 in PCOS theca cells results in a significant reduction in CYP17A1 and CYP11A1 expression, and decreased androgen and progestin biosynthesis. Knockdown of endogenous DENND1A.V2 in PCOS theca cells, following transfection of PCOS theca cells with silencing DENND1A.V2 shRNA1 and shRNA2 plasmids significantly inhibited both basal (P<0.05) and 20 μM forskolin (*, P<0.01) stimulated CYP17 mRNA accumulation, as compared to Scrambled plasmid (FIG. 7A). Transfection with silencing DENND1A.V2 shRNA plasmids on PCOS theca also significantly inhibited forskolin-stimulated (*, P<0.05) CYP11A1 mRNA accumulation (FIG. 7B).
Figure 7B:
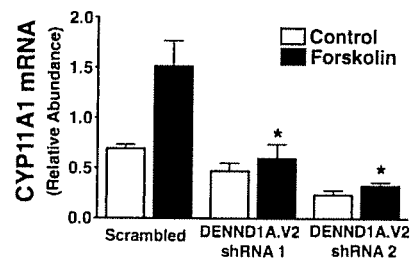

To determine the effect of knock-down of endogenous DENND1A.V2 mRNA on CYP17A1 and CYP11A1 mRNA levels, silencing DENND1A.V2 shRNA plasmids were transfected into PCOS theca cells, and basal and forskolin stimulated CYP17A1 mRNA was assessed using qRT-PCR. In these experiments $4^{th}$ passage PCOS theca cells were transfected with pRSV-Scrambled plasmid or plasmids specific to DENND1A.V2 (pSV-shRNA1 or pRSV-shRNA2). 6 h following transfection, the cells were treated with and without 20 μM forskolin, and 24h thereafter, total RNA was harvested, and CYP17A1, CYP11A1 and TBP mRNA abundance was measured. As shown in FIG. 7A, DENND1A.V2 shRNA1 and shRNA2 retrovirus plasmid significantly inhibited both basal and forskolin stimulated CYP17A1 mRNA accumulation in PCOS theca cells. Both of the DENND1A.V2 shRNA plasmids also significantly inhibited forskolin-stimulated CYP11A1 mRNA (FIG. 7B) in PCOS theca cells [34]. For these experiments Western and qRT-PCR analyses confirmed that DENND1A.V2 protein was significantly decreased following DENND1A shRNA transfection [34].

Figure 7C:
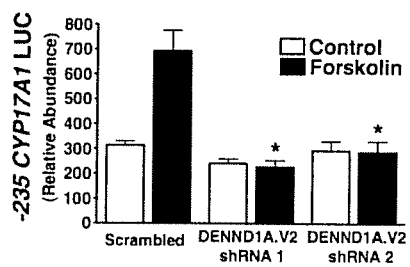

Parallel studies were performed to evaluate whether silencing shRNAs specific to DENND1A.V2 would inhibit CYP17A1 promoter function (i.e., transcription) in PCOS theca cells. PCOS theca cells were transfected with a CYP17A1 luciferase reporter plasmid (−235 CYP17A1/LUC) containing −235/+44 of the CYP17A1 promoter fused to the luciferase gene in pGL3. Scrambled pRV expression vector or plasmid encoding the silencing DENND1A.V2 pRV-shRNA1 or pRV-shRNA2 was also added to the transfection mixture. 6 h following transfection, the cells were rinsed with PBS, and treated in serum-free medium with and without 20 μM forskolin. 24 h thereafter luciferase activity was determined. The results from these experiments showed that transfection of DENND1A.V2 shRNA1 inhibited basal and cAMP-dependent CYP17A1 reporter activity in PCOS theca cells, compared to scrambled shRNA. An increase in both basal and forskolin-stimulated −235 CYP17A1/LUC promoter regulation in PCOS theca cells was observed. As shown in FIG. 7C, co-transfection of −235CYP17A1/LUC with a silencing DENND1A.V2 shRNA1 or shRNA2 resulted in a significant reduction of forskolin-dependent CYP17A1 reporter activity in PCOS theca cells, compared to Scrambled shRNA [34].

Silencing of DENND1A.V2 Expression by shRNA Lentivirus Particles Inhibits PCOS Theca Cell Steroidogenesis.

Figure 7D:
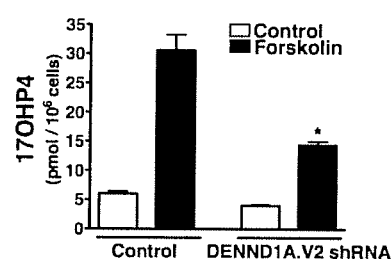
Figure 7E:
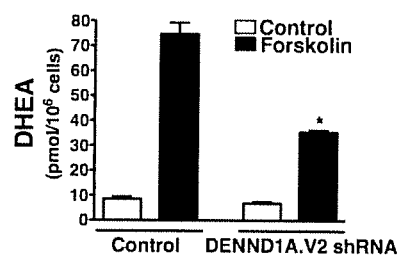
Figure 7F:
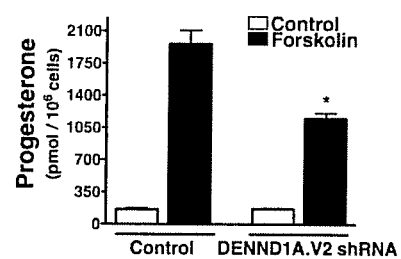

To evaluate the effect of knockdown of DENND1A.V2 on steroid biosynthesis, custom Thermo/Dharmacon GIPZ DENND1A.V2 shRNA particles were utilized. PCOS theca cells were infected with 300,000 particles/well of silencing shRNA DENND1A.V2 lentivirus or a control non-silencing lentivirus in serum free medium[34]. Six hours thereafter the lentivirus mixture was removed the cells were transferred into serum free medium in the presence or absence of forskolin for 72 h. Infection with silencing shRNA DENND1A.V2 lentivirus significantly inhibited forskolin-stimulated 17OHP4 (FIG. 7D), DHEA biosynthesis (FIG. 7E), and P4 (FIG. 7F). Although there was a trend towards inhibition in basal steroidogenesis following DENND1A.V2 lentivirus infection, the design of lentiviral infection experiments precluded the accurate assessment of basal steroid concentrations.

Rabbit polyclonal Anti-DENND1A.V2 Specific IgG Reduces DHEA Secretion and CYP17A1 mRNA in PCOS Theca Cells.

DENND1A is known to be associated with the cell membrane and clathrin coated pits, potentially making DENND1A epitopes available to antibodies added to the cell exterior. We generated a rabbit polyclonal antibody against a 21 amino acid peptide (QKSITHFAAKFPTRGWTSSSH) (SEQ ID NO:6) that is specific to DENND1A.V2 (FIG. 1C-D). This DENND1A.V2 specific IgG was added to the culture medium of normal and PCOS theca cells to determine whether it could be used to block or neutralize DENND1A.V2 function, and thus alter steroid biosynthesis in normal and PCOS theca cells. In these experiments PCOS theca cells were treated with increasing concentrations of a DENND1A.V2 isoform specific IgG or non-specific IgG, in the presence or absence of 20 μM forskolin. As shown in FIG. 8A, DENND1A.V2 IgG significantly inhibits forskolin-stimulated DHEA biosynthesis, with an approximate $ID_{50}$ of 0.25 μg/mL. In contrast, non-specific IgG had no effect on DHEA biosynthesis[34].

Figure 8C:
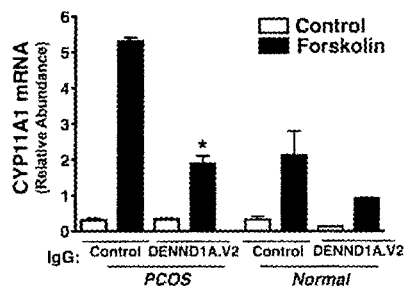

Subsequent experiments were performed to examine the effects of 0.5 µg/mL of rabbit polyclonal DENND1A.V2 specific IgG or 0.5 µg/mL non-specific IgG on CYP17A1 mRNA (FIG. 8B) and CYP11A1 mRNA (FIG. 8C) accumulation following 16 h treatment in the presence and absence of 20 µM forskolin in normal and PCOS theca cells from various individual patients [34]. The data in FIG. 8B demonstrate that 0.5 µg/mL DENND1A.V2 specific IgG significantly inhibits CYP17A1 mRNA accumulation in PCOS theca cells, under control and forskolin-stimulated conditions following 16 h of treatment. In contrast, in normal theca cells, DENND1A.V2 IgG had no effect on basal or forskolin-stimulated CYP17A1 mRNA (FIG. 8B). As shown in FIG. 8C, DENND1A.V2 specific IgG also significantly inhibited forskolin-stimulated CYP11A1 mRNA accumulation in PCOS theca cells, while having no effect on CYP11A1 mRNA accumulation in normal theca cells.

Figure 8D:
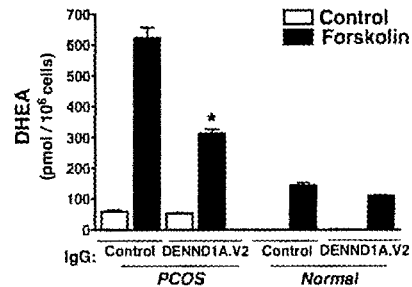
Figure 8E:
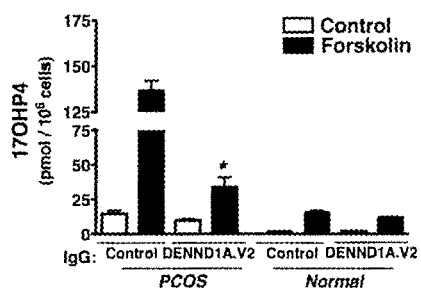
Figure 8F:
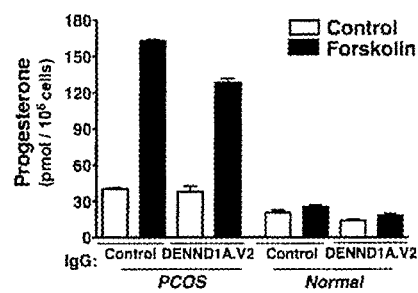

In parallel experiments, normal and PCOS theca cells from individual patients were treated with 0.5 µg/mL of affinity purified rabbit polycolonal DENND1A.V2 specific IgG or 0.5 µg/mL or non-specific IgG and basal and forskolin stimulated absence DHEA (FIG. 8D), 17OHP4 (FIG. 8E), and P4 (FIG. 8F) biosynthesis on a per cell basis was measured following 72 h treatment. The results of these experiments showed that rabbit polyclonal DENND1A.V2 specific IgG significantly inhibited forskolin-stimulated DHEA (FIG. 8D) and 17OHP4 (FIG. 8E), in PCOS theca cells by 50% as compared to control IgG, without affecting normal theca cells.

Discussion

It will be apparent from the foregoing that we have carried out the first studies to examine the expression of DENND1A in well characterized theca cells from normal cycling and PCOS women. The discovery that increased expression of a splice variant of DENND1A mRNA, DENND1A.V2, is characteristic of PCOS theca cells provided a basis for pursuing studies on the functional consequences of this molecule in terms of theca cell function [34].

Forced expression of DENND1A.V2 in normal theca cells increases CYP17A1 and CYP11A1 gene expression and converts the cells to a PCOS phenotype of augmented androgen and progestin biosynthesis. In contrast, knockdown of DENND1A.V2 with silencing shRNA plasmids or lentivirus in PCOS theca cells reverts the cells to a normal phenotype of reduced CYP17A1 and CYP11A1 gene expression and androgen and progestin biosynthesis. These observations suggest that DENND1A is involved in a signaling cascade that augments transcription of steroidogenic genes that subsequently results in increased androgen production.

DENND1A.V2 is a truncated connecdenn 1, which has a clathrin-binding domain and is thought to facilitate endocytosis. Among the loci associated with PCOS in Han Chinese [41-43], several reside in or near genes that potentially define a network, including the FSHR, LHCGR, and INSR, which encode receptors that reside on the plasma membrane, and which are internalized by clathrin coated pits, where DENND1A protein is located [25, 42, 44]. The DENN domains of DENND1A function as Rab-specific guanine nucleotide exchange factors [26]. Ras related protein 5B (RAB5B), another PCOS GWAS candidate, is a Rab-GTPase, also thought to be involved in endocytosis and receptor recycling and could, therefore, be a molecule interacting with the DENN domain [45, 46]. RAB5B signaling has also been reported to involve PI3K, PKB, and MAPK/ERK components [44-47]. Without being bound by theory, it is possible that the truncated form of DENND1A.V2 affects insulin or LH-receptor turnover and sensitivity in theca and/or granulosa cells, further affecting ovarian function and steroid biosynthesis in PCOS women. DENND1A has also been shown to be associated with lipids, particularly phosphoinsitol-3-phosphate, and other endocytosis/endosome proteins [26], and could potentially be involved in insulin and LH-receptor signaling. Alternatively, DENND1A.V2 may have a more direct role in controlling gene expression. DENND1A.V2 may be translocated into the nucleus, a process that may be facilitated by RAB5B, another GWAS discovered PCOS candidate, where it may be involved in transcriptional activation of CYP17A1 and CYP11A1 gene expression [34].

Using specific rabbit polyclonal, and human and mouse monoclonals anti-DENND1A.V2 IgG, it has been shown in the Examples herein that DENND1A.V2 epitopes are available to extracellular antibodies. The observation that augmented CYP17A1 and CYP11A mRNA and androgen biosynthesis in PCOS theca cells can be reduced using DENND1A.V2 specific IgG indicates that biologic agents such as humanized monoclonal antibodies against DENND1A.V2 are useful therapeutic agents for the hyperandrogenemia associated with PCOS, and possibly other phenotypes related to insulin action.

These findings demonstrate that a splice variant (DENND1A.V2) derived from the DENND1A gene, has a functional role in controlling theca cell steroidogenesis [34]. Overexpression of DENND1A.V2 is sufficient to convert normal theca cells into a PCOS biochemical phenotype characterized by increased CYP17A1 and CYP11A1 gene expression and augmented androgen and progestin production. Suppression of DENND1A.V2 function pushes PCOS theca cells towards a normal phenotype in terms of steroidogenic enzyme gene expression and steroid production. The fact that DENND1A.V2 mRNA is elevated in urine of women with PCOS and that a DENND1A.V2-specific IgG can transform the biochemical characteristics of PCOS theca cells, reducing steroidogenesis, indicates the usefulness of DENND1A.V2-specific antibodies for non-invasive detection of PCOS and also for biological therapy of PCOS [34]

Example 2. Humanized Monoclonal Antibodies Specific for DENND1A.V2 Isolated from a Phage Display Library are Useful for the Treatment of PCOS Materials and Methods Phage Display Screening.

To obtain a functional humanized mAB specific to DENND1A.V2, a newly made Phage Display Scl-2 Library (Creative Biolabs, New York) was screened [48-54]. The antibody and antigen binding fragments were intended to target the unique 33 amino acid C-terminus of the DENND1A.V2 protein. The 33 amino acid DENND1A.V2 sequence that is unique between DENND1A Variants 1 and 2 is: NTIATPATLHILQKSITHFAAKFPTRGWTSS SH (SEQ ID NO:5). For panning, the unique 21 amino acid sequence segment: QKSITHFAAKFPTRGWTSSSH (SEQ ID NO:6) was utilized. This is the sequence that was previously used to obtain a functional rabbit polyclonal antibody to DENND1A.V2 (see Example 1).

Materials Used for Phage Display

A newly prepared phage display Scl-2 Library

E. coli TG1 host strain

M13KO7 helper phage:

Primers:

L1: 5'-TggAATTgTgAgCggATAACAATT-3' (SEQ ID NO:54)

S6: 5'-gTAAATgAATTTTCTgTATgAgg-3' (SEQ ID NO:55)

Target: CH22, DENND1A.V2

Rabbit anti-M13 pAb-HRP

Initially, two DENND1A variant 2 peptide-protein conjugates [KLH- and BSA-conjugate] to QKSITHFAAKFPTRGWTSSSH (SEQ ID NO:6) were utilized to perform phage display panning to select specific binders to the peptide itself. After coating the peptide-BSA conjugate directly, affinity panning and QC phage ELISA were conducted. The results showed that no specific enriching effect was observed.

A biotinylated version of the DENND1A.V2 specific peptide (QKSITHFAAKFPTRGWTSSSH; SEQ ID NO:6) was synthesized, and new panning was performed with a freshly made phage library as described in Table 2 by immobilizing the bio-peptide with strepavidin pre-coated plates. A strong enriching effect was observed after three rounds of screening. 40 clones were picked up either from the trypsin-digestion eluate or the competitive eluate, and subjected to phage amplification and phage ELISA (Tables 3-4).

TABLE 2

Human Phage Panning process for CH22 DENND1A.V2 amino acid sequence target QKSITHFAAKFPTRGWTSSSH (SEQ ID NO: 6) (i.e., Biotin-CH22)

| Round | Conditions | Input | Output | Enriching factor |
|---|---|---|---|---|
| $1^{st}$ | Target protein: 100 ug/ml Biotin-CH22<br>Washing: 0.1% Tween20 PBST, 10 times<br>Elution: Trypsin digestion<br>Pre counter select: 2% M-PBS | $1.10 \times 10^{11}$ | $2.48 \times 10^5$ | $4.44 \times 10^5$ |
| $2^{nd}$-P | Target protein: 60 ug/ml Biotin-CH22<br>Washing: 0.2% Tween20 PBST, 10 times<br>Elution: Trypsin digestion<br>Pre counter select: 2% M-PBS | $1.60 \times 10^{11}$ | $8.32 \times 10^5$ | $1.92 \times 10^5$ |
| $2^{nd}$-N | Target protein: no coating<br>Washing: 0.2% Tween20 PBST, 10 times<br>Elution: Trypsin digestion<br>Pre counter select: 2% M-PBS | $4.00 \times 10^{10}$ | $3.00 \times 10^3$ | $1.33 \times 10^7$ |
| $3^{rd}$-P1 | Target protein: 40 ug/ml Biotin-CH22<br>Washing: 0.2% Tween20 PBST, 10 times<br>Elution: Trypsin digestion<br>Pre counter select: 2% M-PBS | $1.60 \times 10^{11}$ | $7.98 \times 10^6$ | $2.01 \times 10^4$ |
| $3^{rd}$-N | Target protein: no coating<br>Washing: 0.2% Tweenβ20 PBST, 10 times<br>Elution: Trypsin digestion<br>Pre counter select: 2% M-PBS | $4.00 \times 10^{10}$ | $4.78 \times 10^4$ | $8.37 \times 10^5$ |
| $3^{rd}$-P2 | Target protein: 40 ug/ml Biotin-CH22<br>Washing: 0.2% Tween20 PBST, 10 times<br>Elution: Competitive digestion<br>Pre counter select: 2% M-PBS | $1.60 \times 10^{11}$ | $1.01 \times 10^6$ | $1.58 \times 10^5$ |
| $3^{rd}$-N | Target protein: no coating<br>Washing: 0.2% Tween20 PBST, 10 times<br>Elution: Competitive digestion<br>Pre counter select: 2% M-PBS | $4.00 \times 10^{10}$ | $5.50 \times 10^3$ | $7.27 \times 10^6$ |

Enriching factor = input/output

TABLE 3

QC monoclonal phage ELISA-1. Reactivity of the human M13K07 monoclonal phage clones to the biotinylated DENND1A.V2 amino acid sequence QKSITHFAAKFPTRGWTSSSH (SEQ ID NO: 6) (i.e., Biotin-CH22)

| Clones | Coating: Biotin-CH22 | No coating |
|---|---|---|
| 1 | 0.140 | 0.101 |
| 2 | 0.228 | 0.109 |
| 3 | 0.128 | 0.099 |
| 4 | 0.123 | 0.099 |
| 5 | 0.127 | 0.125 |
| 6 | 0.115 | 0.128 |
| 7 | 0.134 | 0.100 |
| 8 | 0.115 | 0.105 |
| 9 | 0.159 | 0.096 |
| 10 | 0.273 | 0.108 |
| 11 | 0.143 | 0.096 |
| 12 | 0.142 | 0.094 |
| 13 | 0.147 | 0.088 |
| 14 | 0.223 | 0.095 |
| 15 | 0.422 | 0.196 |
| 16 | 1.669 | 0.089 |
| 17 | 0.130 | 0.133 |
| 18 | 0.221 | 0.100 |
| 19 | 0.124 | 0.121 |
| 20 | 0.127 | 0.111 |
| 21 | 0.170 | 0.102 |
| 22 | 0.137 | 0.102 |
| 23 | 0.167 | 0.102 |
| 24 | 0.230 | 0.094 |
| 25 | 0.135 | 0.110 |
| 26 | 0.135 | 0.085 |
| 27 | 0.140 | 0.085 |
| 28 | 0.179 | 0.104 |
| 29 | 0.165 | 0.089 |

TABLE 3-continued

QC monoclonal phage ELISA-1. Reactivity of the human
M13K07 monoclonal phage clones to the biotinylated
DENND1A.V2 amino acid sequence QKSITHFAAKFPTRGWTSSSH
(SEQ ID NO: 6) (i.e., Biotin-CH22)

| Clones | Coating: Biotin-CH22 | No coating |
|---|---|---|
| 30 | 0.125 | 0.098 |
| 31 | 0.140 | 0.109 |
| 32 | 0.164 | 0.074 |
| 33 | 0.121 | 0.096 |
| 34 | 0.196 | 0.102 |
| 35 | 0.248 | 0.142 |
| 36 | 0.179 | 0.108 |
| 37 | 0.118 | 0.085 |
| 38 | 0.126 | 0.111 |
| 39 | 0.151 | 0.104 |
| 40 | 0.146 | 0.089 |
| 1-A | 0.311 | 0.091 |
| 2-A | 0.731 | 0.103 |
| 3-A-1 | 0.877 | 0.077 |
| 3-A-2 | 0.951 | 0.070 |
| M13KO7 | 0.477 | 0.074 |
| 1% M-PBS | 0.081 | 0.066 |

M13KO7 phages: 10(3) cfu/ml
1-A: Amplified phages of the $1^{st}$ eluate
2-A: Amplified phages of the $2^{nd}$ eluate
3-A: Amplified phages of the $3^{rd}$ eluate

TABLE 4

QC monoclonal phage ELISA-2. Reactivity of the human
M13K07 monoclonal phage clones to the biotinylated
DENND1A.V2 amino acid sequence QKSITHFAAKFPTRGWTSSSH
(SEQ ID NO: 6) (i.e., Biotin-CH22).

| Clones | Coating: Biotin-CH22 | No coating |
|---|---|---|
| 41 | 0.184 | 0.096 |
| 42 | 0.193 | 0.108 |
| 43 | 0.178 | 0.116 |
| 44 | 0.179 | 0.096 |
| 45 | 0.218 | 0.102 |
| 46 | 0.200 | 0.099 |
| 47 | 0.238 | 0.100 |
| 48 | 0.176 | 0.101 |
| 49 | 0.158 | 0.103 |
| 50 | 0.221 | 0.114 |
| 51 | 0.165 | 0.097 |
| 52 | 0.181 | 0.094 |
| 53 | 0.220 | 0.141 |
| 54 | 0.141 | 0.098 |
| 55 | 0.161 | 0.097 |
| 56 | 0.169 | 0.101 |
| 57 | 0.229 | 0.111 |
| 58 | 0.208 | 0.144 |
| 59 | 0.345 | 0.157 |
| 60 | 0.326 | 0.116 |
| 61 | 0.167 | 0.115 |
| 62 | 0.213 | 0.159 |
| 63 | 0.190 | 0.130 |
| 64 | 0.162 | 0.106 |
| 65 | 0.278 | 0.081 |
| 66 | 0.180 | 0.120 |
| 67 | 0.227 | 0.101 |
| 68 | 0.369 | 0.122 |
| 69 | 0.270 | 0.098 |
| 70 | 0.223 | 0.129 |
| 71 | 0.199 | 0.105 |
| 72 | 0.164 | 0.115 |
| 73 | 0.222 | 0.107 |
| 74 | 0.214 | 0.109 |
| 75 | 0.154 | 0.102 |
| 76 | 0.289 | 0.100 |
| 77 | 0.176 | 0.094 |
| 78 | 0.184 | 0.113 |
| 79 | 1.535 | 0.112 |
| 80 | 0.279 | 0.102 |
| M13KO7 | 0.533 | 0.114 |
| 1% M-PBS | 0.115 | 0.072 |

M13KO7: 10(10) cfu/ml

Figure 13A:
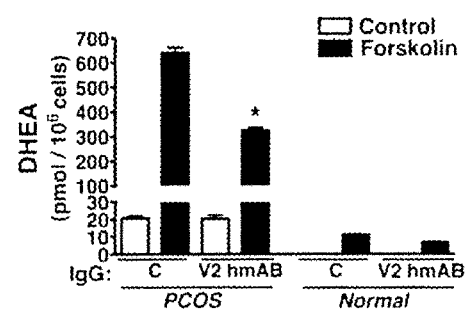
FIG. 13A-B. Effects of recombinant human DENND1A.V2 specific IgG1 on DHEA biosynthesis in normal and PCOS theca cells. Both rabbit polyclonal and human recombinant DENND1A.V2 reduce DHEA biosynthesis in PCOS theca cells. Experiments performed to compare the effect of 9 μg/mL human recombinant DENND1A.V2 IgG1 (V2 hmAB) and non-specific IgG1 in normal and PCOS theca cells treated in the absence (C; control) and presence of 20 μM forskolin.

Using the biotinylated DENND1A.V2 peptide QKSITH-FAAKFPTRGWTSSSH (SEQ ID NO:6) as the target, two strong binding scFv's (clones 16 and 79) were identified (Tables 3-4). Sequence analysis of scFv phage clones 16 and 79 showed that the nucleotide and peptide sequences of these clones were identical (FIG. 9A-B). The VL and VH of this scFV were cloned into plasmids containing the human light (pIgG1-L) and heavy chains (pIgG1-H) of IgG1 (FIG. 10A-D). Following transfection, these constructs were expressed in HEK293 cells, and the resulting human recombinant DENND1A.V2 IgG1 was expressed and purified (FIG. 11A-C). Briefly, a plasmid vector was transfected into 293E cells. The suspension culture was collected 96 hours after transfection. The product was purified by HiTrap rProteinA FF and filtered using a 0.2 μm filter. The resulting human recombinant DENND1A.V2 specific IgG (V2 hmAB) (FIG. 11B) was then utilized to perform functional studies using ovarian androgen producing human theca cells isolated from normal cycling women and women with PCOS (FIGS. 12A-B and FIG. 13A).

Results

Phage Display Results.

As shown in Table 2, a strong enriching effect was found after three rounds of screening. Accordingly, 40 clones were picked up either from the trypsin-digestion eluate or the competitive eluate for further QC ELISA assay. The first 40 clones from the trypsin-digestion eluate were subjected to QC phage ELISA. As shown in Table 3, one strong positive clone, clone 16, were identified together with a few weak positive clones. The second 40 clones from the competitive eluate were also subjected to QC phage ELISA. As shown in Table 4, a second strong positive clone, clone 79, was identified with a few weak positive clones. DNA sequencing was performed on the two strong positive clones and several weak positive binding clones. 7 unique scFvs were identified. Two strong positive clones (clones 16 and 79) shared the same scFv sequence (see FIG. 9).

Soluble scFv Expression and Soluble scFv ELISA.

The strong positive scFv gene (identical clones 16, 79) was cloned into a soluble scFv expression vector pCDisplay-2 for further soluble scFv expression and soluble scFv ELISA. As shown in Table 5, when the *E. coli* lysate containing soluble scFv-AP fusion proteins was coated directly, expression was successfully confirmed. As shown in Table 6, when biotinylated DENND1A.V2 peptide was immobilized via a streptavidin pre-coated plate, the positive binding of scFv-AP was confirmed as well.

TABLE 5

ELISA analysis of soluble scFv fusion proteins from phage
clones 16 and 79 using *E coli* lysate directly.

| Clones | 30° C. | 37° C. |
|---|---|---|
| 16-① | 1.934 | 0.682 |
| 16-② | 1.681 | 0.882 |
| 79-① | 1.821 | 1.161 |

TABLE 5-continued

ELISA analysis of soluble scFv fusion proteins from phage clones 16 and 79 using *E coli* lysate directly.

| Clones | 30° C. | 37° C. |
|---|---|---|
| 79-② | 1.975 | 0.943 |
| TG1 | | 0.098 |
| 1% M-TBS | | 0.130 |

TABLE 6

QC soluble scFv ELISA using immobilize DENND1A.V2 biotinylated peptide via strep-avidin pre-coating plate.

| Clones | Temp. | Coating: Biotin-CH22 | No coating |
|---|---|---|---|
| 16-① | 30° C. | 2.132 | 0.191 |
| | 37° C. | 2.102 | 0.206 |
| 16-② | 30° C. | 2.118 | 0.179 |
| | 37° C. | 2.172 | 0.160 |
| 79-① | 30° C. | 2.144 | 0.222 |
| | 37° C. | 2.144 | 0.196 |
| 79-② | 30° C. | 2.142 | 0.212 |
| | 37° C. | 2.100 | 0.211 |
| TG1 | — | 0.150 | 0.139 |
| 1% M-TBS | — | 0.121 | 0.130 |

The VL and VH of the scFv identified from phage display, were cloned into plasmids containing the human light (pIgG1-L) and heavy chains (pIgG1-H) of IgG1, and sequenced. As shown in FIGS. 10A-D the VH and VL of the heavy and light chains of these clones were identical to those of the scFv (FIG. 9A-9B). The CDRs of both the VH and VL are underlined and bracketed.

Recombinant human DENND1A.V2 specific IgG1 functionally inhibits DHEA biosynthesis in PCOS theca cells.

Dose response experiments were performed to examine whether the recombinant human IgG1 obtained from phage display screening with the biotinylated DENND1A.V2 21 amino acid peptide (QKSITHFAAKFPTRGWTSSSH)(SEQ ID NO:6) could neutralize the effects of augmented DENND1A.V2 expression and reduce steroid biosynthesis in PCOS theca cells (FIG. 12). In these experiments PCOS theca cells were treated with increasing concentrations (0.01-6 µg/mL) of a human recombinant monoclonal IgG1 specific for DENND1A.V2 (V2 hmAB) or a non-specific IgG1, treated in the absence (C) and presence of 20 µM forskolin (F) for 72 h. As shown in FIG. 12A, there was a dose dependent decrease in DHEA biosynthesis. V2 hmAB significantly decreased (*, $P<0.01$) forskolin-stimulated DHEA biosynthesis with an approximate ID50 of 1.8 µg/mL, compared to control IgG1. Examination of the effects of 3.0 ng/ml and 6.0 ng/ml non-specific IgG1 or V2 hmAB on PCOS theca cell biosynthesis, showed that both basal and forskolin (*, $P<0.1$) stimulated DHEA biosynthesis were inhibited following treatment with V2 hmAB as compared to control IgG1 (FIG. 12B). In parallel preliminary studies, human recombinant DENND1A.V2 IgG1 also inhibited basal and forskolin-stimulated CYP17 mRNA accumulation (data not shown).

Subsequent experiments were performed to examine the effects of a maximal dose of human recombinant DENND1A.V2 IgG1 (V2 hmAB) (9 µg/ml) and non-specific IgG1 (9 µg/ml) on androgen biosynthesis in normal and PCOS theca cells from various individual patients, treated in the absence (C) and presence of 20 µM forskolin, for 72 h. As shown in FIG. 13A, a maximal dose of V2 hmAB IgG1 significantly (*, $P<0.01$) inhibited forskolin-stimulated DHEA biosynthesis in PCOS theca cells, while having minimal effect on DHEA accumulation in normal theca cells.

Figure 13B:
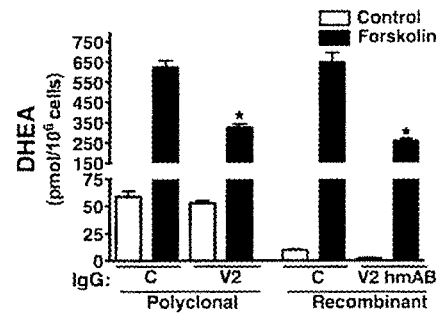

A comparison of the effects of rabbit DENND1A.V2 polyclonal (FIG. 8) and human recombinant DENND1A.V2 IgG1 (FIGS. 12A-B and 13A) on DHEA biosynthesis demonstrated that both antibodies generated against the C-terminal DENND1A.V2 21 amino acid peptide have reduced basal and forskolin-stimulated androgen biosynthesis in PCOS theca cells, as compared to control IgG (FIG. 13B)

Example 3. Mouse Monoclonal Antibodies Specific for DENND1A.V2 Provides the CDR Sequence Information of a Functional IgG1 for the Construction of Humanized Monoclonals for the Therapeutic Treatment of PCOS Materials and Methods Production of Mouse Monoclonal Antibodies to DENND1A Peptide.

Mouse monoclonal antibodies to the DENND1A peptide QKSITHFAAKFPTRGWTSSSH (SEQ ID NO:6) were prepared using standard procedures [55]. BALB/c mice were immunized using KLH-coupled peptide in RIBI adjuvant. Immunizations were delivered both subcutaneously and intra-peritoneally in volumes of 0.05 ml per site per mouse per immunization. Immunizations were given bi-weekly 3 times, the final booster immunization was given as KLH-peptide in saline. Three days after the final booster immunization, the mice were anesthetized using ketamine/xylazine and spleen and lymph nodes removed following exsanguination. Single cell suspensions of immune cells were prepared and fused with P3X63-Ag8.653 myeloma cells for the production of hybridomas. Supernatants from cultures of hybridomas were screened by ELISA for reactivity to the peptide, and to BSA-peptide and positive cultures isolated for expansion and cloning. Positive clones producing reactive antibodies in ELISA were adapted to serum free conditions using Sigma serum-free culture media and then high titer antibodies were produced using BDBiosciences CELLine devices. Cultures containing antibody were then purified using Protein A/G columns (Pierce, Rockford, Ill.) and used in the various antibody detection and function assays.

Figure 14:
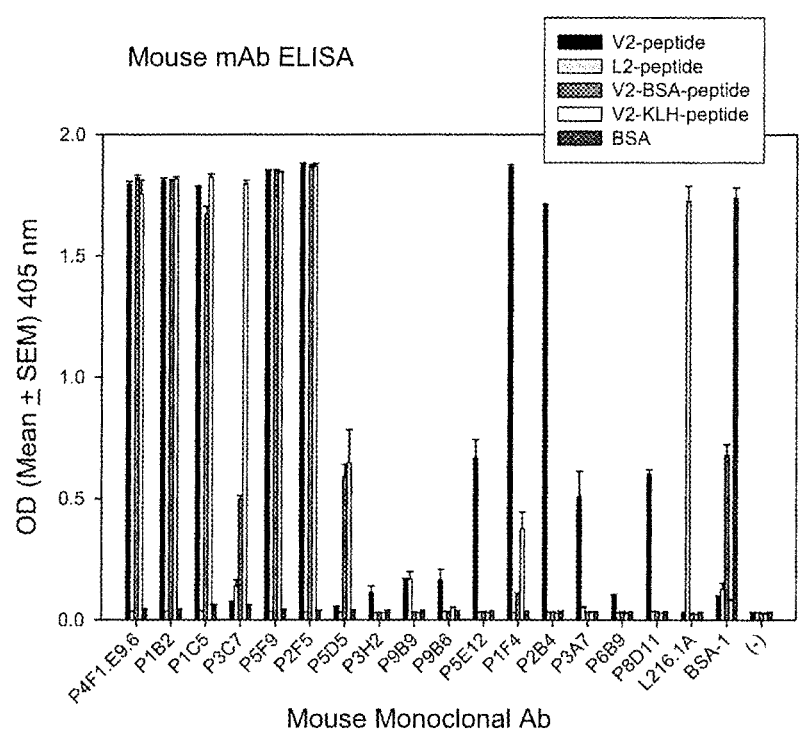
FIG. 14. Mouse monoclonal antibody reactivity of selected hybridomas in ELISA to DENND1A peptide. An ELISA scan of mouse monoclonal antibody supernatants for selected hybridomas was performed. Each hybridoma supernatant (1:10 dilution) was tested for binding reactivity to DENND1A.V2 antigens including free peptide (V2-peptide, QKSITHFAAKFPTRGWTSSSH) (SEQ ID NO:6), labeled V2-KLH-peptide and V2-BSA-peptide, as well as control peptide and BSA. A control peptide to the HPV16 L2 (L2 peptide) sequence (aa17-36) and a monoclonal reactive to this peptide (L216.1A), were used as internal negative control monoclonal antibodies. A second control monoclonal (BSA-1) was reactive to BSA. Several monoclonal antibodies were identified to have specific reactivity to DENND1A.V2 free peptide as well as V2-KLH- and V2-BSA labeled peptide, including P1B2, P1C5, P4F1, P5F9, and P2F5.

ELISA binding activity of a panel of mouse monoclonal antibodies. ELISA was conducted to assess binding characteristics of selected monoclonal antibodies that appeared positive in the primary screening of the fusions. The basic method is to coat ELISA plate wells with various DENND1A.V2 antigen sources (KLH-peptide; BSA-peptide, free peptide, control peptide and BSA) at 1 ug/ml in Bicarbonate binding buffer (pH 9.6) then test a single dilution of hybridoma cell culture supernatant in duplicate. The optical density readings at 405 nm were established from a plate reader, and mean±SEM of OD readings plotted for each antigen and each hybridoma supernatant. Some of the reactive hybridomas were cloned by limiting dilution, isotype characterized, and retested in the ELISA. An example of the binding profiles of the mouse monoclonal antibodies by ELISA are shown in FIG. 14. Several monoclonal antibodies were identified to have specific reactivity to DENND1A.V2 free peptide (SEQ ID NO:6) as well as KLH- and BSA labeled peptide, including P1B2, P1C5, P4F1, P5F9, and P2F5.

RNA Extraction and Sequence Analysis of the Mouse DENND1A.V2 Monoclonal Antibodies.

ELISA-positive monoclonal hybridoma cells were pelleted by centrifugation and re-suspended in TRIzol Reagent (Life Technologies) for RNA isolation. Total RNA was extracted from the homogenate and the resulting RNA pellet was dissolved in 100 µl HyClone HyPure Molecular Biology Grade Water (Thermo Scientific). cDNA was synthesized using the RevertAid First Strand cDNA synthesis kit which included both the random hexamer primers and the recombinant M-MuLV RT used for the synthesis. The resulting cDNA was amplified by ChoiceTaq DNA Polymerase (Denville Scientific Inc.) and IgG1 heavy chain redundant and kappa light chain redundant primers [55][56]. PCR products were purified using the QIAquick PCR purification kit (Qiagen). Using the same primers as was used for PCR amplification, PCR products were directly sequenced by Operon. Sequences were analyzed and translated using DNAMAN software and sequenced using the same PCR primers.

Functional Evaluation of the Mouse Monoclonal Antibodies on Androgen Biosynthesis.

The hybridoma cells from the P1B2 and P1C5 mouse monoclonal clones were further subcloned, and the culture media from these cultures were utilized to treat PCOS theca cells, to evaluate their effects on ovarian androgen biosynthesis in PCOS theca cells as described in Example 1, Material and Methods.

Sequence Analysis of the Mouse DENND1A.V2 Monoclonal Antibodies.

RNA was prepared from the PIB2 and P1C5 hybridoma clones. A partial nucleotide and amino sequence of the heavy and light chains of mAb P1B2, and heavy chains of P1C5 are shown in FIGS. 16A-D.

Results

Mouse DENND1A.V2 mAB ELISA.

An ELISA scan of mouse monoclonal antibody supernatants for selected hybridomas identified several monoclonal antibodies that had specific reactivity to DENND1A.V2 free peptide (SEQ ID NO:6) as well as KLH- and BSA labeled peptide, including P1B2, P1C5, P4F1, P5F9, and P2F5 (FIG. 14)

Inhibitory Effects of Mouse Monoclonal V2 IgG1 on Androgen Biosynthesis.

Figure 15:
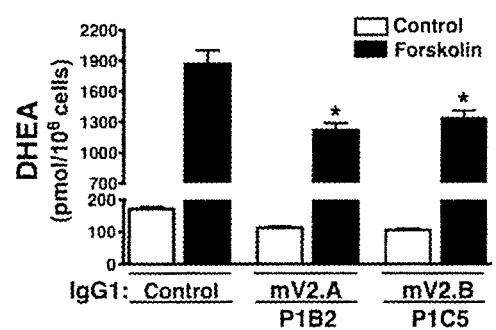
FIG. 15. Inhibitory effects of mouse monoclonal DENND1A.V2 IgG1 on androgen biosynthesis. Experiments were performed to examine the functional effects of the DENND1A.V2 mouse monoclonal antibodies, P1B2 and P1C5, that were shown to be reactive in the ELISA screen (FIG. 14) on androgen biosynthesis in PCOS theca cells. PCOS theca cells were treated with 40 μL of tissue culture supernatant of either P1B2 (mV2.A) and P1C5 (mV2.B) mouse IgG1, or negative control mouse IgG1, in the presence and absence of 20 μM forskolin for 72 h.

Experiments were performed to investigate whether the mouse P1B2 (mV2.A) and P1C5 (mV2.B). DENND1A.V2 monoclonal antibodies that were generated against KLH-conjugated DENND1A.V2 specific 21 amino acid peptide (QKSITHFAAKFPTRGWTSSSH) (SEQ ID NO:6), could similarly neutralize DENND1A.V2 in PCOS theca cells and suppress androgen biosynthesis. In these experiments, PCOS theca cells were treated with 40 µL of tissue culture supernatant of either mV2.A and mV2.B mouse IgG1, or negative control mouse IgG1 in the presence and absence of 20 µM forskolin for 72 h. The data in FIG. 14 demonstrate that both DENND1A.V2 specific mV2.A and mV2.B mouse IgG1 inhibit forskolin-stimulated DHEA biosynthesis in PCOS theca cells (*, P<0.05) as compared to negative control mouse IgG1. The data in FIGS. 12-13 and 15 demonstrates that both human and mouse DENND1A/V2 specific antibodies suppress DHEA biosynthesis in PCOS theca cells. This is in agreement with results obtained using rabbit DENND1A.V2 specific polyclonal antibody (FIG. 8). These data further support the notion that monoclonal antibodies specific to DENND1A.V2 could be used as a therapeutic modality for PCOS.

Sequences of the DENND1A.V2 Specific Mouse Monoclonal Antibodies P1B2 and P1C5.

Both the DNA and protein sequences of the mouse monoclonal DENND1A.V2 specific IgG1, P1B2 heavy chain (FIGS. 16A and C; SEQ ID NOs: 60 and 62), P1B2 light chain (FIGS. 16B and D; SEQ ID NOs:61 and 63), and the heavy chain of P1C5 (FIG. 16E-F; SEQ ID NOs: 64 and 65) nucleotide and amino acid sequences are provided. The CDRs are bracketed.

REFERENCES

1 Dunaif, A. (2012) Polycystic ovary syndrome in 2011: Genes, aging and sleep apnea in polycystic ovary syndrome. *Nat Rev Endocrinol* 8, 72-74
2 Balen, A., et al. (2009) Defining polycystic ovary syndrome. *BMJ* 338, a2968
3 Franks, S., et al. (2008) Ovarian morphology is a marker of heritable biochemical traits in sisters with polycystic ovaries. *The Journal of Clinical Endocrinology and Metabolism* 93, 3396-3402
4 Franks, S., et al. (2008) Follicle dynamics and anovulation in polycystic ovary syndrome. *Human Reproduction Update* 14, 367-378
5 Dunaif, A., Chang, R. J., Franks, S. et al. (2008) *Polycystic Ovary Syndrome: Current Controversies, from the Ovary to the Pancreas*. Humana Press, Totowa, N.J.
6 Azziz, R., et al. (2006) Positions statement: criteria for defining polycystic ovary syndrome as a predominantly hyperandrogenic syndrome: an Androgen Excess Society guideline. *The Journal of clinical endocrinology and metabolism* 91, 4237-4245
7 Rotterdam, et al. (2004) Revised 2003 consensus on diagnostic criteria and long-term health risks related to polycystic ovary syndrome (PCOS). *Human reproduction* 19, 41-47
8 Franks, S., et al. (2000) Pathogenesis of polycystic ovary syndrome: evidence for a genetically determined disorder of ovarian androgen production. *Hum Fertil (Camb)* 3, 77-79
9 Goodarzi, M. O., et al. (2011) Polycystic ovary syndrome: etiology, pathogenesis and diagnosis. *Nat Rev Endocrinol* 7, 219-231
10 Zawadzki, J. and Dunaif, A. (1992) *Diagnostic criteria for polycystic ovary syndrome: Towards a rational approach*. Blackwell Scientific Publications, Boston, Mass., 377-384
11 Jakubowicz, D. and Nestler, J. (1997) 17α-Hydroxyprogesterone response to leuprolide and serum androgens in obese women with and without polycystic ovary syndrome after dietary weight loss. *The Journal of Clinical Endocrinology and Metabolism* 82, 556-559
12 Gilling-Smith, C., et al. (1997) Evidence for a primary abnormality in theca cell steroidogenesis in the polycystic ovarian syndrome. *Clin Endocrinol* 47, 1158-1165
13 Nestler, J. E., et al. (1998) Insulin stimulates testosterone biosynthesis by human thecal cells from women with polycystic ovary syndrome by activating its own receptor and using inositolglycan mediators as the signal transduction system. *The Journal of Clinical Endocrinology and Metabolism* 83, 2001-2005
14 Gilling-Smith, C., et al. (1994) Hypersecretion of androstenedione by isolated thecal cells from polycystic ovaries. *The Journal of Clinical Endocrinology and Metabolism* 79, 1158-1165

15 Nelson, V. L., et al. (1999) Augmented androgen production is a stable steroidogenic phenotype of propagated theca cells from polycystic ovaries. *Molecular Endocrinology* 13, 946-957

16 Nelson, V. L., et al. (2001) The biochemical basis for increased testosterone production in theca cells propagated from patients with polycystic ovary syndrome. *The Journal of Clinical Endocrinology and Metabolism* 86, 5925-5933

17 Wickenheisser, J. K., et al. (2000) Differential activity of the cytochrome P450 17alpha-hydroxylase and steroidogenic acute regulatory protein gene promoters in normal and polycystic ovary syndrome theca cells. *The Journal of Clinical Endocrinology and Metabolism* 85, 2304-2311

18 Magoffin, D. A. (2006) Ovarian enzyme activities in women with polycystic ovary syndrome. *Fertility and sterility* 86 Suppl 1, S9-S11

19 Jakimiuk, A. J., et al. (2001) Luteinizing hormone receptor, steroidogenesis acute regulatory protein, and steroidogenic enzyme messenger ribonucleic acids are overexpressed in thecal and granulosa cells from polycystic ovaries. *Journal of Clinical Endocrinology and Metabolism* 86, 1318-1323

20 Wickenheisser, J. K., et al. (2012) Cholesterol side-chain cleavage gene expression in theca cells: augmented transcriptional regulation and mRNA stability in polycystic ovary syndrome. *PloS one* 7, e48963

21 Strauss, J. F., 3rd (2003) Some new thoughts on the pathophysiology and genetics of polycystic ovary syndrome. *Ann NY Acad Sci* 997, 42-48

22 Wickenheisser, J. K., et al. (2004) Increased cytochrome P450 17alpha-hydroxylase promoter function in theca cells isolated from patients with polycystic ovary syndrome involves nuclear factor-1. *Molecular Endocrinology* 18, 588-605

23 Wood, J. R., et al. (2004) The molecular signature of polycystic ovary syndrome (PCOS) theca cells defined by gene expression profiling. *J Reprod Immunol* 63, 51-60

24 Wood, J. R., et al. (2003) The molecular phenotype of polycystic ovary syndrome (PCOS) theca cells and new candidate PCOS genes defined by microarray analysis. *The Journal of Biological Chemistry* 278, 26380-26390

25 Strauss, J. F., 3rd, et al. (2012) Persistence pays off for PCOS gene prospectors. *The Journal of Clinical Endocrinology and Metabolism* 97, 2286-2288

26 Marat, A. L., et al. (2011) DENN domain proteins: regulators of Rab GTPases. *The Journal of Biological Chemistry* 286, 13791-13800

27 Jones, P. T., et al. (1986) Replacing the complementarity-determining regions in a human antibody with those from a mouse. *Nature* 321, 522-525

28 Riechmann, L., et al. (1988) Reshaping human antibodies for therapy. *Nature* 332, 323-327

29 Presta, L. G. (1992) Antibody engineering. *Curr Opin Stuctural Biol* 2, 593-596

30 Verhoeyen, M., et al. (1988) Reshaping human antibodies: grafting an antilysozyme activity. *Science* 239, 1534-1536

31 McAllister, J. and Simpson, E. (1993) *Human theca interna cells in culture*. Academic Press, San Diego, Calif. 330-339

32 Nelson-DeGrave, V. L., et al. (2004) Valproate potentiates androgen biosynthesis in human ovarian theca cells. *Endocrinology* 145, 799-808

33 Legro, R. S., et al. (1998) Phenotype and genotype in polycystic ovary syndrome. *Recent Prog Horm Res* 53, 217-256

34 McAllister, J. M., et al. (2014) Overexpression of a DENND1A isoform produces a polycystic ovary syndrome theca phenotype. *Proceedings of the National Academy of Sciences of the United States of America* 111, E1519-1527

35 De Windt, L. J., et al. (2000) Calcineurin promotes protein kinase C and c-Jun NH2-terminal kinase activation in the heart. Cross-talk between cardiac hypertrophic signaling pathways. *The Journal of Biological Chemistry* 275, 13571-13579

36 Liang, Q., et al. (2001) The transcription factor GATA4 is activated by extracellular signal-regulated kinase 1- and 2-mediated phosphorylation of serine 105 in cardiomyocytes. *Molecular and Cellular Biology* 21, 7460-7469

37 Fujishiro, M., et al. (2001) MKK6/3 and p38 MAPK pathway activation is not necessary for insulin-induced glucose uptake but regulates glucose transporter expression. *The Journal of Biological Chemistry* 276, 19800-19806

38 Nelson-Degrave, V. L., et al. (2005) Alterations in mitogen-activated protein kinase kinase and extracellular regulated kinase signaling in theca cells contribute to excessive androgen production in polycystic ovary syndrome. *Molecular Endocrinology* 19, 379-390

39 Graham, F. and Eb, A. V. D. (1973) A new technique for the assay of infectivity of human adenovirus 5. *Virology* 52, 456-457

40 Thorvaldsdottir, H., et al. (2013) Integrative Genomics Viewer (IGV): high-performance genomics data visualization and exploration. *Briefings in Bioinformatics* 14, 178-192

41 Chen, Z. J., et al. (2011) Genome-wide association study identifies susceptibility loci for polycystic ovary syndrome on chromosome 2p16.3, 2p21 and 9q33.3. *Nat Genet* 43, 55-59

42 Shi, Y., et al. (2012) Genome-wide association study identifies eight new risk loci for polycystic ovary syndrome. *Nat Genet* 44, 1020-1025

43 Goodarzi, M. O., et al. (2012) Replication of association of DENND1A and THADA variants with polycystic ovary syndrome in European cohorts. *J Med Genet* 49, 90-95

44 Allaire, P. D., et al. (2010) The Connecdenn DENN domain: a GEF for Rab35 mediating cargo-specific exit from early endosomes. *Molecular Cell* 37, 370-382

45 Stenmark, H. (2009) Rab GTPases as coordinators of vesicle traffic. *Nat Rev Mol Cell Biol* 10, 513-525

46 Stenmark, H. and Olkkonen, V. M. (2001) The Rab GTPase family. *Genome Biol* 2, 3007

47 Chiariello, M., et al. (1999) The small GTPases Rab5a, Rab5b and Rab5c are differentially phosphorylated in vitro. *FEBS Lett* 453, 20-24

48 Chen, G. and Sidhu, S. S. (2014) Design and generation of synthetic antibody libraries for phage display. *Methods in Molecular Biology* 1131, 113-131

49 Sidhu, S. S. (2000) Phage display in pharmaceutical biotechnology. *Current Opinion in Biotechnology* 11, 610-616

50 Sidhu, S. S. (2001) Phage display: increasing the rewards from genomic information. *Drug Discovery Today* 6, 936

51 Sidhu, S. S. (2001) Engineering M13 for phage display. *Biomolecular Engineering* 18, 57-63

52 Sidhu, S. S., et al. (2003) Exploring protein-protein interactions with phage display. *Chembiochem: a European Journal of Chemical Biology* 4, 14-25

53 Sidhu, S. S., et al. (2007) M13 bacteriophage coat proteins engineered for improved phage display. *Methods in Molecular Biology* 352, 205-219

54 Held, H. A. and Sidhu, S. S. (2004) Comprehensive mutational analysis of the M13 major coat protein: improved scaffolds for C-terminal phage display. *Journal of Molecular Biology* 340, 587-597
55 Brendle, S. A., et al. (2010) Binding and neutralization characteristics of a panel of monoclonal antibodies to human papillomavirus 58. *The Journal of General Virology* 91, 1834-1839
56 Wang, Z., et al. (2000) Universal PCR amplification of mouse immunoglobulin gene variable regions: the design of degenerate primers and an assessment of the effect of DNA polymerase 3' to 5' exonuclease activity. *Journal of Immunological Methods* 233, 167-177

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An antibody or antigen binding fragment thereof that recognizes a DENN/MADD-domain-containing 1A variant 2 (DENND1A.V2) and comprises six complementarity-determining region (CDR) sequences of SEQ ID NO: 53.

2. The antibody or antigen binding fragment thereof of claim 1, wherein a heavy chain of the antibody or antigen binding fragment thereof comprises a sequence at least 70% identical to SEQ ID NO: 58 and wherein a light chain of the antibody comprises a sequence at least 70% identical to SEQ ID NO: 59.

3. The antibody or antigen binding fragment thereof of claim 1, wherein a heavy chain of the antibody or antigen binding fragment thereof comprises SEQ ID NO: 58 and wherein a light chain of the antibody comprises SEQ ID NO: 59.

4. The antibody or antigen binding fragment thereof of claim 1, wherein the antibody is a human monoclonal antibody.

5. The antibody or antigen binding fragment thereof of claim 1, wherein the antibody is humanized.

6. A pharmaceutical composition comprising the antibody or the antigen binding fragment of claim 1 and a pharmaceutically acceptable carrier.

* * * * *

SEQUENCE LISTING

```
<160> NUMBER OF SEQ ID NOS: 72

<210> SEQ ID NO 1
<211> LENGTH: 2166
<212> TYPE: DNA
<213> ORGANISM: Homo sapiens

<400> SEQUENCE: 1
cgcgcgccgg gcacgcgcgc cggcgaccat ggcgttcgcc gggctggagc gagtacatta      60
acccctggag gcggcggcgg cggcgaggga gcgagcctcg agcgggcggg ccccagcctg     120
agggaaggga ggaaggggcg gggagagcgc cagagggagg ccggtcggcc gcgggcgggc     180
gggcagcgca gcgccgagcg gggcccgcgg gcccatgagg aggcctgggg accatgggct     240
ccaggatcaa gcagaatcca gagaccacat ttgaagtata tgttgaagtg gcctatccca     300
ggacaggtgg cactctttca gatcctgagg tgcagaggca attcccggag gactacagtg     360
accaggaagt tctacagact ttgaccaagt tttgtttccc cttctatgtg gacagcctca     420
cagttagcca agttggccag aacttcacat tcgtgctcac tgacattgac agcaaacaga     480
gattcgggtt ctgccgctta tcttcaggag cgaagagctg cttctgtatc ttaagctatc     540
tcccctggtt cgaggtattt tataagctgc ttaacatcct ggcagattac acgacaaaaa     600
gacaggaaaa tcagtggaat gagcttcttg aaactctgca caaacttccc atccctgacc     660
caggagtgtc tgtccatctc agcgtgcatt cttattttac tgtgcctgat accagagaac     720
ttcccagcat acctgagaat agaaatctga cagaatattt tgtggctgtg gatgttaaca     780
acatgttgca tctgtacgcc agtatgctgt acgaacgccg gatactcatc atttgcagca     840
aactcagcac tctgactgcc tgcatccacg ggtctgcggc gatgctctac cccatgtact     900
ggcagcacgt gtacatcccc gtgctgccgc cgcatctgct ggactactgc tgtgctccca     960
tgccctacct cataggaatc catttaagtt taatggagaa agtcagaaac atggccctgg    1020
atgatgtcgt gatcctgaat gtggacacca acaccctgga aacccccttc gatgacctcc    1080
agagcctccc aaacgacgtg atctcttccc tgaagaacag gctgaaaaag gtctccacaa    1140
ccactgggga tggtgtggcc agagcgttcc tcaaggccca ggctgctttc ttcggtagct    1200
accgaaacgc tctgaaaatc gagccggagg agccgatcac tttctgtgag gaagccttcg    1260
tgtcccacta ccgctccgga gccatgaggc agttcctgca gaacgccaca cagctgcagc    1320
tcttcaagca gtttattgat ggtcgattag atcttctcaa ttccggcgaa ggtttcagtg    1380 atgttttga agaggaaatc aacatgggcg agtacgctgg cagtgacaaa ctgtaccatc    1440
agtggctctc cactgtccgg aaaggaagtg gagcaattct gaatactgta aagaccaaag    1500
caaatccggc catgaagact gtctacaagt tcgcaaaaga tcatgcaaaa atgggaataa    1560
aagaggtgaa aaaccgcttg aagcaaaagg acattgccga gaatggctgc gcccccaccc    1620
cagaagagca gctgccaaag actgcaccgt ccccactggt ggaggccaag gaccccaagc    1680
```

```
tccgagaaga ccggcggcca atcacagtcc actttggaca ggtgcgccca cctcgtccac    1740
atgttgttaa gagaccaaag agcaacatcg cagtggaagg ccggaggacg tctgtgccga    1800
gccctgagca aaacaccatt gcaacaccag ctacactcca catcctacag aaaagcatta    1860
cccattttgc ggccaagttc ccgacgagag gctggacctc ttcatcacat tgacttacgc    1920
cgttgctttt ccagactggg cagaggggct gacttcgcag tgtgtgccaa agagccggtg    1980
tctgataatc ccattttcct gcttatcacc tgaactgtgt cagtatcact tttagttttg    2040
ttggttggtt ggtttgttgt tgtttaata tgccctgttt tctacttctg ttggaaaata    2100 tttgggggttg aaataaacca gtgggagcat ggaaaaaaaa aaaaaaaaaa aaaaaaaaa    2160 aaaaaa                                                              2166
```

<210> SEQ ID NO 2
<211> LENGTH: 559
<212> TYPE: PRT
<213> ORGANISM: Homo sapiens

<400> SEQUENCE: 2

```
Met Gly Ser Arg Ile Lys Gln Asn Pro Glu Thr Thr Phe Glu Val Tyr
1               5                   10                  15

Val Glu Val Ala Tyr Pro Arg Thr Gly Gly Thr Leu Ser Asp Pro Glu
            20                  25                  30

Val Gln Arg Gln Phe Pro Glu Asp Tyr Ser Asp Gln Glu Val Leu Gln
        35                  40                  45

Thr Leu Thr Lys Phe Cys Phe Pro Phe Tyr Val Asp Ser Leu Thr Val
    50                  55                  60

Ser Gln Val Gly Gln Asn Phe Thr Phe Val Leu Thr Asp Ile Asp Ser
65                  70                  75                  80

Lys Gln Arg Phe Gly Phe Cys Arg Leu Ser Ser Gly Ala Lys Ser Cys
                85                  90                  95

Phe Cys Ile Leu Ser Tyr Leu Pro Trp Phe Glu Val Phe Tyr Lys Leu
            100                 105                 110

Leu Asn Ile Leu Ala Asp Tyr Thr Thr Lys Arg Gln Glu Asn Gln Trp
        115                 120                 125

Asn Glu Leu Leu Glu Thr Leu His Lys Leu Pro Ile Pro Asp Pro Gly
    130                 135                 140

Val Ser Val His Leu Ser Val Ser Tyr Phe Thr Val Pro Asp Thr
145                 150                 155                 160

Arg Glu Leu Pro Ser Ile Pro Glu Asn Arg Asn Leu Thr Glu Tyr Phe
                165                 170                 175

Val Ala Val Asp Val Asn Asn Met Leu His Leu Tyr Ala Ser Met Leu
            180                 185                 190

Tyr Glu Arg Arg Ile Leu Ile Cys Ser Lys Leu Ser Thr Leu Thr
        195                 200                 205

Ala Cys Ile His Gly Ser Ala Ala Met Leu Tyr Pro Met Tyr Trp Gln
    210                 215                 220

His Val Tyr Ile Pro Val Leu Pro Pro His Leu Leu Asp Tyr Cys Cys
225                 230                 235                 240

Ala Pro Met Pro Tyr Leu Ile Gly Ile His Leu Ser Leu Met Glu Lys
                245                 250                 255

Val Arg Asn Met Ala Leu Asp Asp Val Val Ile Leu Asn Val Asp Thr
            260                 265                 270

Asn Thr Leu Glu Thr Pro Phe Asp Asp Leu Gln Ser Leu Pro Asn Asp
        275                 280                 285
```

```
Val Ile Ser Ser Leu Lys Asn Arg Leu Lys Lys Val Ser Thr Thr Thr
            290                 295                 300

Gly Asp Gly Val Ala Arg Ala Phe Leu Lys Ala Gln Ala Ala Phe Phe
305                 310                 315                 320

Gly Ser Tyr Arg Asn Ala Leu Lys Ile Glu Pro Glu Pro Ile Thr
            325                 330                 335

Phe Cys Glu Glu Ala Phe Val Ser His Tyr Arg Ser Gly Ala Met Arg
                340                 345                 350

Gln Phe Leu Gln Asn Ala Thr Gln Leu Gln Leu Phe Lys Gln Phe Ile
            355                 360                 365

Asp Gly Arg Leu Asp Leu Leu Asn Ser Gly Glu Gly Phe Ser Asp Val
370                 375                 380

Phe Glu Glu Glu Ile Asn Met Gly Glu Tyr Ala Gly Ser Asp Lys Leu
385                 390                 395                 400

Tyr His Gln Trp Leu Ser Thr Val Arg Lys Gly Ser Gly Ala Ile Leu
                405                 410                 415

Asn Thr Val Lys Thr Lys Ala Asn Pro Ala Met Lys Thr Val Tyr Lys
            420                 425                 430

Phe Ala Lys Asp His Ala Lys Met Gly Ile Lys Glu Val Lys Asn Arg
435                 440                 445

Leu Lys Gln Lys Asp Ile Ala Glu Asn Gly Cys Ala Pro Thr Pro Glu
450                 455                 460

Glu Gln Leu Pro Lys Thr Ala Pro Ser Pro Leu Val Glu Ala Lys Asp
465                 470                 475                 480

Pro Lys Leu Arg Glu Asp Arg Pro Ile Thr Val His Phe Gly Gln
                485                 490                 495

Val Arg Pro Pro Arg Pro His Val Val Lys Arg Pro Lys Ser Asn Ile
            500                 505                 510

Ala Val Glu Gly Arg Arg Thr Ser Val Pro Ser Pro Glu Gln Asn Thr
            515                 520                 525

Ile Ala Thr Pro Ala Thr Leu His Ile Leu Gln Lys Ser Ile Thr His
530                 535                 540

Phe Ala Ala Lys Phe Pro Thr Arg Gly Trp Thr Ser Ser Ser His
545                 550                 555

<210> SEQ ID NO 3
<211> LENGTH: 5041
<212> TYPE: DNA
<213> ORGANISM: Homo sapiens

<400> SEQUENCE: 3
cgcgcgccgg gcacgcgcgc cggcgaccat ggcgttcgcc gggctggagc gagtacatta      60
acccctggag gcggcggcgg cggcgaggga gcgagcctcg agcgggcggg ccccagcctg     120
agggaaggga ggaagggggcg gggagagcgc cagaggagg ccggtcggcc gcgggcgggc     180
gggcagcgca gcgccgagcg gggcccgcgg gcccatgagg aggcctgggg accatgggct     240
ccaggatcaa gcagaatcca gagaccacat ttgaagtata tgttgaagtg cctatccca      300 ggacaggtgg cactctttca gatcctgagg tgcagaggca attcccggag gactacagtg     360
accaggaagt tctacagact ttgaccaagt tttgtttccc cttctatgtg acagcctca      420 cagttagcca agttggccag aacttcacat tcgtgctcac tgacattgac agcaaacaga     480
gattcgggtt ctgccgctta tcttcaggag cgaagagctg cttctgtatc ttaagctatc     540 tccctggtt cgaggtattt tataagctgc ttaacatcct ggcagattac acgacaaaaa     600
```

-continued

```
gacaggaaaa tcagtggaat gagcttcttg aaactctgca caaacttccc atccctgacc      660
caggagtgtc tgtccatctc agcgtgcatt cttattttac tgtgcctgat accagagaac      720
ttcccagcat acctgagaat agaaatctga cagaatattt tgtggctgtg atgttaaca       780 acatgttgca tctgtacgcc agtatgctgt acgaacgccg atactcatc atttgcagca       840 aactcagcac tctgactgcc tgcatccacg ggtctgcggc gatgctctac cccatgtact      900
ggcagcacgt gtacatcccc gtgctgccgc cgcatctgct ggactactgc tgtgctccca      960
tgccctacct cataggaatc catttaagtt taatggagaa agtcagaaac atggccctgg     1020
atgatgtcgt gatcctgaat gtggacacca acaccctgga aaccccttc gatgacctcc      1080 agagcctccc aaacgacgtg atctcttccc tgaagaacag gctgaaaaag gtctccacaa     1140
ccactgggga tggtgtggcc agagcgttcc tcaaggccca ggctgctttc ttcggtagct     1200
accgaaacgc tctgaaaatc gagccggagg agccgatcac tttctgtgag gaagccttcg     1260
tgtcccacta ccgctccgga gccatgaggc agttcctgca gaacgccaca cagctgcagc     1320
tcttcaagca gtttattgat ggtcgattag atcttctcaa ttccggcgaa ggtttcagtg     1380
atgtttttga agaggaaatc aacatggggcg agtacgctgg cagtgacaaa ctgtaccatc     1440
agtggctctc cactgtccgg aaaggaagtg gagcaattct gaatactgta aagaccaaag     1500
caaatccggc catgaagact gtctacaagt cgcaaaaga tcatgcaaaa atgggaataa      1560
aagaggtgaa aaaccgcttg aagcaaaagg acattgccga gaatggctgc gcccccaccc     1620
cagaagagca gctgccaaag actgcaccgt ccccactggt ggaggccaag gaccccaagc     1680
tccgagaaga ccggcggcca atcacagtcc actttggaca ggtgcgccca cctcgtccac     1740
atgttgttaa gagaccaaag agcaacatcg cagtggaagg ccggaggacg tctgtgccga     1800
gccctgagca gccgcagccg tatcggacac tcagggagtc agacagcgcg gaaggcgacg     1860
aggcagagag tccagagcag caagtgcgga agtccacagg ccctgtccca gctcccctg      1920 accgggctgc cagcatcgac cttctggaag acgtcttcag caacctggac atggaggccg     1980
cactgcagcc actgggccag gccaagagct tagaggacct tcgtgccccc aaagacctga     2040
gggagcagca agggaccttt gactatcaga ggctggatct gggcgggagt gagaggagcc     2100
gcggggtgac agtggccttg aagcttaccc accggtacaa caagctctgg agcctgggcc     2160
aggacgacat ggccatcccc agcaagcccc cagctgcctc ccctgagaag ccctcggccc     2220
tgctcgggaa ctccctggcc ctgcctcgaa ggccccagaa ccgggacagc atcctgaacc     2280
ccagtgacaa ggaggaggtg cccaccccta ctctgggcag catcaccatc ccccggcccc     2340
aaggcaggaa gaccccagag ctgggcatcg tgcctccacc gccccattcc cgccggcca      2400 agctccaggc tgccggcgcc gcacttggtg acgtctcaga gcggctgcag acggatcggg     2460
acaggcgagc tgccctgagt ccagggctcc tgcctggtgt tgtcccccaa ggccccactg     2520
aactgctcca gccgctcagc cctggcccg gggctgcagg cacgagcagt gacgccctgc     2580
tcgccctcct ggaccgctc agcacagcct ggtcaggcag caccctcccg tcacgcccg      2640 ccaccccgaa tgtagccacc ccattcaccc cccaattcag cttccccct gcagggacac     2700 ccacccatt cccacagcca ccactcaacc cctttgtccc atccatgcca gcagcccac      2760 ccaccctgcc cctggtctcc acaccagccg ggccttcgg ggcccctcca gcttccctgg     2820
ggccggcttt tgcgtccggc ctcctgctgt ccagtgctgg cttctgtgcc cctcacaggt     2880
ctcagcccaa cctctccgcc ctctccatgc ccaacctctt tggccagatg cccatgggca     2940
```

```
cccacacgag cccctacag ccgctgggtc cccagcagt tgccccgtcg aggatccgaa    3000
cgttgcccct ggcccgctca agtgccaggg ctgctgagac caagcagggg ctggccctga   3060
ggcctggaga ccccccgctt ctgcctccca gcccctca aggcctggag ccaacactgc    3120
agccctctgc tcctcaacag gccagagacc cctttgagga tttgttacag aaaaccaagc   3180
aagacgtgag cccgagtccg gccctggccc cggccccaga ctcggtggag cagctcagga   3240
agcagtggga gaccttcgag tgagccgggc cctgagggtg ggggatgcac cgaggcccga   3300
gggtccgtcc actgctgcgg ttccgaggct ccccgccac tctctctctg cccaggttct    3360
gctggtggga agggatggga cccctctctg ctgcccctc ctcccctcca cactgcccat    3420
ctctgatgtc tggccctggg aatggcacc agttccagcc tgggaatcaa cccagttcct   3480
gagtgcccat cccaccccgc ggttgcctct cctcggcacc cttgattggg ttttgcacta   3540
aagaggtcag ctgggccaat gatattgctc cagaccgagt cctacccacc ttccccgga   3600 agtgtcccaa gaggctccga aggcctcccc tccgagccca gctctcctgt ctcctccaca   3660
gccaggccct gcacgcccac ctcctcggac acaggtgaca gggttaccct ccagtttgag   3720
ctcatctgca cgagacacag gtagcttggg gttgaagtta ggactcctcc tgggctggag   3780
gatttacctg gtggggcact tccagactgt ttctagcaat atacacacac gttctttcct    3840
gtgtcttcac cccaaaactt cagttgattc tgacctggga ggatctgggg accaggggt    3900 cttgggctgc cttgtgatac acagccccag ccaccctgca cggggctgc gagcaccagc   3960 aactttgatt tatagaagga aaatggaaac ccccatctga gtattttggg aggagccccc   4020
agccctcatc cagctctggc acgctgatac ctccaggtac tccctcact gtcaaagctg    4080 gggctcagcc tcttgtcatc tggagctttg tgggcaaagc tgagaagctg caacccagat   4140
ttcaacccaa aaaggtcaag ctgaatgcct cagactgatg tggaaggcag ctggccttcc   4200
tgggttggaa cgaggcagtg gccctgagcc ccttctccag gccaggtag aaaggacaaa    4260 cttggtctct gcctcgggga agcaggagga gggctagaag ccagtccctc cccacctgcc   4320
cagagctcca ggccagcaca gaaattcctg aggccaacgt caccaaagtt agattgaatg   4380
tttattatct ttcttttttcc tttttaccttt attgatttga tgaatcttga aatggattca   4440
tttccataaa ccaagttaaa gtatggcccg accatttaag aaaacaacca tctgagacac   4500
gcaggaaatt gtgagcattt cgacccgagc tctcatttcc tatttgtgaa gggtcagaca   4560
cagtctaccc aggggtgtct gggggacaag ggggtctctg gagatgtcac ccagggagcc   4620
ccctctatgt ctgagaggct gccactgctg cacatgctca gtgaggcttg gcggccatcc   4680
tggcacatgg ctcttcctgg gtcaaccgtg acctgtctgg ctcaggaatg ggctctggct   4740
gctgggggag ccgtgtcact cctgggccat ggggcacct cctgggcact taggtgtttc    4800
agcatagatt ccagtttcgc accctgggca gaccccagg ccccatccgg gatagggcag    4860
aggaggtgct ggcggcccca gggaaggagg gtgtgtaccc caaggcccc tggctgtgct    4920 gaggggctgg ggtgagcgct ccatgttcac atgagcactg ctgcctcttc acttgtggga   4980 cttttttgcaa acccaaggat gaactttgtg tgcattcaat aaaatcatct tggggaagag   5040
g                                                                   5041
```

<210> SEQ ID NO 4
<211> LENGTH: 1009
<212> TYPE: PRT
<213> ORGANISM: Homo sapiens

<400> SEQUENCE: 4

```
Met Gly Ser Arg Ile Lys Gln Asn Pro Glu Thr Thr Phe Glu Val Tyr
1               5                   10                  15

Val Glu Val Ala Tyr Pro Arg Thr Gly Gly Thr Leu Ser Asp Pro Glu
            20                  25                  30

Val Gln Arg Gln Phe Pro Glu Asp Tyr Ser Asp Gln Glu Val Leu Gln
        35                  40                  45

Thr Leu Thr Lys Phe Cys Phe Pro Phe Tyr Val Asp Ser Leu Thr Val
    50                  55                  60

Ser Gln Val Gly Gln Asn Phe Thr Phe Val Leu Thr Asp Ile Asp Ser
65                  70                  75                  80

Lys Gln Arg Phe Gly Phe Cys Arg Leu Ser Ser Gly Ala Lys Ser Cys
                85                  90                  95

Phe Cys Ile Leu Ser Tyr Leu Pro Trp Phe Glu Val Phe Tyr Lys Leu
            100                 105                 110

Leu Asn Ile Leu Ala Asp Tyr Thr Thr Lys Arg Gln Glu Asn Gln Trp
        115                 120                 125

Asn Glu Leu Leu Glu Thr Leu His Lys Leu Pro Ile Pro Asp Pro Gly
    130                 135                 140

Val Ser Val His Leu Ser Val His Ser Tyr Phe Thr Val Pro Asp Thr
145                 150                 155                 160

Arg Glu Leu Pro Ser Ile Pro Glu Asn Arg Asn Leu Thr Glu Tyr Phe
                165                 170                 175

Val Ala Val Asp Val Asn Asn Met Leu His Leu Tyr Ala Ser Met Leu
            180                 185                 190

Tyr Glu Arg Arg Ile Leu Ile Cys Ser Lys Leu Ser Thr Leu Thr
        195                 200                 205

Ala Cys Ile His Gly Ser Ala Ala Met Leu Tyr Pro Met Tyr Trp Gln
    210                 215                 220

His Val Tyr Ile Pro Val Leu Pro Pro His Leu Leu Asp Tyr Cys Cys
225                 230                 235                 240

Ala Pro Met Pro Tyr Leu Ile Gly Ile His Leu Ser Leu Met Glu Lys
                245                 250                 255

Val Arg Asn Met Ala Leu Asp Asp Val Val Ile Leu Asn Val Asp Thr
            260                 265                 270

Asn Thr Leu Glu Thr Pro Phe Asp Asp Leu Gln Ser Leu Pro Asn Asp
        275                 280                 285

Val Ile Ser Ser Leu Lys Asn Arg Leu Lys Lys Val Ser Thr Thr Thr
    290                 295                 300

Gly Asp Gly Val Ala Arg Ala Phe Leu Lys Ala Gln Ala Ala Phe Phe
305                 310                 315                 320

Gly Ser Tyr Arg Asn Ala Leu Lys Ile Glu Pro Glu Glu Pro Ile Thr
                325                 330                 335

Phe Cys Glu Glu Ala Phe Val Ser His Tyr Arg Ser Gly Ala Met Arg
            340                 345                 350

Gln Phe Leu Gln Asn Ala Thr Gln Leu Gln Leu Phe Lys Gln Phe Ile
        355                 360                 365

Asp Gly Arg Leu Asp Leu Leu Asn Ser Gly Gly Phe Ser Asp Val
    370                 375                 380

Phe Glu Glu Glu Ile Asn Met Gly Glu Tyr Ala Gly Ser Asp Lys Leu
385                 390                 395                 400

Tyr His Gln Trp Leu Ser Thr Val Arg Lys Gly Ser Gly Ala Ile Leu
                405                 410                 415
```

-continued

Asn Thr Val Lys Thr Lys Ala Asn Pro Ala Met Lys Thr Val Tyr Lys
            420                 425                 430

Phe Ala Lys Asp His Ala Lys Met Gly Ile Lys Glu Val Lys Asn Arg
            435                 440                 445

Leu Lys Gln Lys Asp Ile Ala Glu Asn Gly Cys Ala Pro Thr Pro Glu
            450                 455                 460

Glu Gln Leu Pro Lys Thr Ala Pro Ser Pro Leu Val Glu Ala Lys Asp
465                 470                 475                 480

Pro Lys Leu Arg Glu Asp Arg Arg Pro Ile Thr Val His Phe Gly Gln
            485                 490                 495

Val Arg Pro Pro Arg Pro His Val Val Lys Arg Pro Lys Ser Asn Ile
            500                 505                 510

Ala Val Glu Gly Arg Arg Thr Ser Val Pro Ser Pro Glu Gln Pro Gln
            515                 520                 525

Pro Tyr Arg Thr Leu Arg Glu Ser Asp Ser Ala Glu Gly Asp Glu Ala
            530                 535                 540

Glu Ser Pro Glu Gln Gln Val Arg Lys Ser Thr Gly Pro Val Pro Ala
545                 550                 555                 560

Pro Pro Asp Arg Ala Ala Ser Ile Asp Leu Leu Glu Asp Val Phe Ser
            565                 570                 575

Asn Leu Asp Met Glu Ala Ala Leu Gln Pro Leu Gly Gln Ala Lys Ser
            580                 585                 590

Leu Glu Asp Leu Arg Ala Pro Lys Asp Leu Arg Glu Gln Pro Gly Thr
            595                 600                 605

Phe Asp Tyr Gln Arg Leu Asp Leu Gly Gly Ser Glu Arg Ser Arg Gly
            610                 615                 620

Val Thr Val Ala Leu Lys Leu Thr His Pro Tyr Asn Lys Leu Trp Ser
625                 630                 635                 640

Leu Gly Gln Asp Asp Met Ala Ile Pro Ser Lys Pro Pro Ala Ala Ser
            645                 650                 655

Pro Glu Lys Pro Ser Ala Leu Leu Gly Asn Ser Leu Ala Leu Pro Arg
            660                 665                 670

Arg Pro Gln Asn Arg Asp Ser Ile Leu Asn Pro Ser Asp Lys Glu Glu
            675                 680                 685

Val Pro Thr Pro Thr Leu Gly Ser Ile Thr Ile Pro Arg Pro Gln Gly
            690                 695                 700

Arg Lys Thr Pro Glu Leu Gly Ile Val Pro Pro Pro Ile Pro Arg
705                 710                 715                 720

Pro Ala Lys Leu Gln Ala Ala Gly Ala Ala Leu Gly Asp Val Ser Glu
            725                 730                 735

Arg Leu Gln Thr Asp Arg Asp Arg Arg Ala Ala Leu Ser Pro Gly Leu
            740                 745                 750

Leu Pro Gly Val Val Pro Gln Gly Pro Thr Glu Leu Leu Gln Pro Leu
            755                 760                 765

Ser Pro Gly Pro Gly Ala Ala Gly Thr Ser Ser Asp Ala Leu Leu Ala
770                 775                 780

Leu Leu Asp Pro Leu Ser Thr Ala Trp Ser Gly Ser Thr Leu Pro Ser
785                 790                 795                 800

Arg Pro Ala Thr Pro Asn Val Ala Thr Pro Phe Thr Pro Gln Phe Ser
            805                 810                 815

Phe Pro Pro Ala Gly Thr Pro Thr Pro Phe Pro Gln Pro Leu Asn
            820                 825                 830

```
Pro Phe Val Pro Ser Met Pro Ala Ala Pro Pro Thr Leu Pro Leu Val
        835                 840                 845

Ser Thr Pro Ala Gly Pro Phe Gly Ala Pro Pro Ala Ser Leu Gly Pro
    850                 855                 860

Ala Phe Ala Ser Gly Leu Leu Leu Ser Ser Ala Gly Phe Cys Ala Pro
865                 870                 875                 880

His Arg Ser Gln Pro Asn Leu Ser Ala Leu Ser Met Pro Asn Leu Phe
                885                 890                 895

Gly Gln Met Pro Met Gly Thr His Thr Ser Pro Leu Gln Pro Leu Gly
            900                 905                 910

Pro Pro Ala Val Ala Pro Ser Arg Ile Arg Thr Leu Pro Leu Ala Arg
        915                 920                 925

Ser Ser Ala Arg Ala Ala Glu Thr Lys Gln Gly Leu Ala Leu Arg Pro
    930                 935                 940

Gly Asp Pro Pro Leu Leu Pro Pro Arg Pro Pro Gln Gly Leu Glu Pro
945                 950                 955                 960

Thr Leu Gln Pro Ser Ala Pro Gln Gln Ala Arg Asp Pro Phe Glu Asp
                965                 970                 975

Leu Leu Gln Lys Thr Lys Gln Asp Val Ser Pro Ser Pro Ala Leu Ala
            980                 985                 990

Pro Ala Pro Asp Ser Val Glu Gln  Leu Arg Lys Gln Trp  Glu Thr Phe
        995                 1000                 1005

Glu

<210> SEQ ID NO 5
<211> LENGTH: 33
<212> TYPE: PRT
<213> ORGANISM: Artificial Sequence
<220> FEATURE:
<223> OTHER INFORMATION: Artificial 33 amino acid DENND1A.V2 sequence
      unique between DENND1A Variants 1 and 2

<400> SEQUENCE: 5

Asn Thr Ile Ala Thr Pro Ala Thr Leu His Ile Leu Gln Lys Ser Ile
1               5                   10                  15

Thr His Phe Ala Ala Lys Phe Pro Thr Arg Gly Trp Thr Ser Ser Ser
            20                  25                  30

His

<210> SEQ ID NO 6
<211> LENGTH: 21
<212> TYPE: PRT
<213> ORGANISM: Artificial Sequence
<220> FEATURE:
<223> OTHER INFORMATION: Artificial 21 amino acid DENND1A.V2 sequence
      unique between DENND1A Variants 1 and 2

<400> SEQUENCE: 6

Gln Lys Ser Ile Thr His Phe Ala Ala Lys Phe Pro Thr Arg Gly Trp
1               5                   10                  15

Thr Ser Ser Ser His
            20

<210> SEQ ID NO 7
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence
```

```
<400> SEQUENCE: 7

Asn Thr Ile Ala Thr Pro Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 8

Thr Ile Ala Thr Pro Ala Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 9

Ile Ala Thr Pro Ala Thr Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 10

Ala Thr Pro Ala Thr Leu His
1               5

<210> SEQ ID NO 11
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 11

Thr Pro Ala Thr Leu His Ile
1               5

<210> SEQ ID NO 12
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 12

Pro Ala Thr Leu His Ile Leu
1               5
```

-continued

```
<210> SEQ ID NO 13
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 13

Ala Thr Leu His Ile Leu Gln
1               5

<210> SEQ ID NO 14
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 14

Thr Leu His Ile Leu Gln Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 15

Leu His Ile Leu Gln Lys Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 16

His Ile Leu Gln Lys Ser Ile
1               5

<210> SEQ ID NO 17
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 17

Ile Leu Gln Lys Ser Ile Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence
```

```
<400> SEQUENCE: 18

Leu Gln Lys Ser Ile Thr His
1               5

<210> SEQ ID NO 19
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 19

Gln Lys Ser Ile Thr His Phe
1               5

<210> SEQ ID NO 20
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 20

Lys Ser Ile Thr His Phe Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 21

Ser Ile Thr His Phe Ala Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 22

Ile Thr His Phe Ala Ala Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 23

Thr His Phe Ala Ala Lys Phe
1               5
```

```
<210> SEQ ID NO 24
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 24

His Phe Ala Ala Lys Phe Pro
1               5

<210> SEQ ID NO 25
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 25

Phe Ala Ala Lys Phe Pro Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 26

Ala Ala Lys Phe Pro Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 27

Ala Lys Phe Pro Thr Arg Gly
1               5

<210> SEQ ID NO 28
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 28

Lys Phe Pro Thr Arg Gly Trp
1               5

<210> SEQ ID NO 29
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence
```

```
<400> SEQUENCE: 29

Phe Pro Thr Arg Gly Trp Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 30

Pro Thr Arg Gly Trp Thr Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 31

Thr Arg Gly Trp Thr Ser Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 32

Arg Gly Trp Thr Ser Ser Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Artificial segment of the DENND1A.V2 C-terminal
      sequence

<400> SEQUENCE: 33

Gly Trp Thr Ser Ser Ser His
1               5

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
gggctgactt cggagtgtgt                                                 20

<210> SEQ ID NO 35
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 35
gggctgactt cggagtgtgt                                                    20

<210> SEQ ID NO 36
<211> LENGTH: 29
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is the exemplary position of a dye or
      secondary quenching moiety
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 36
nccaaagagc ncggtgtctg ataatccca                                          29

<210> SEQ ID NO 37
<211> LENGTH: 25
<212> TYPE: DNA
<213> ORGANISM: Artificial Sequence
<220> FEATURE:
<223> OTHER INFORMATION: Synthetic primer

<400> SEQUENCE: 37
tccacatgtt gttaagagac caaag                                              25

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
ccgcaaaatg ggtaatgctt                                                    20

<210> SEQ ID NO 39
<211> LENGTH: 27
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 39
nagccctgag ncaaaacacc attgcaa                                            27
```

```
<210> SEQ ID NO 40
<211> LENGTH: 28
<212> TYPE: DNA
<213> ORGANISM: Artificial Sequence
<220> FEATURE:
<223> OTHER INFORMATION: Synthetic primer

<400> SEQUENCE: 40
ggattcattt ccataaacca agttaaag                                           28

<210> SEQ ID NO 41
<211> LENGTH: 21
<212> TYPE: DNA
<213> ORGANISM: Artificial Sequence
<220> FEATURE:
<223> OTHER INFORMATION: Synthetic primer

<400> SEQUENCE: 41
cacaatttcc tgcgtgtctc a                                                  21

<210> SEQ ID NO 42
<211> LENGTH: 30
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 42
natggcccga nccatttaag aaaacaacca                                         30

<210> SEQ ID NO 43
<211> LENGTH: 22
<212> TYPE: DNA
<213> ORGANISM: Artificial Sequence
<220> FEATURE:
<223> OTHER INFORMATION: Synthetic primer

<400> SEQUENCE: 43
ggcctcaaat ggcaactcta ga                                                 22

<210> SEQ ID NO 44
<211> LENGTH: 21
<212> TYPE: DNA
<213> ORGANISM: Artificial Sequence
<220> FEATURE:
<223> OTHER INFORMATION: Synthetic primer

<400> SEQUENCE: 44
cttctgatcg ccatccttga a                                                  21

<210> SEQ ID NO 45
<211> LENGTH: 26
<212> TYPE: DNA
<213> ORGANISM: Artificial Sequence
<220> FEATURE:
<223> OTHER INFORMATION: Synthetic probe

<400> SEQUENCE: 45
tcgcgtccaa caaccgtaag ggtatc                                             26
```

```
<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
gagggagacg ggcacaca                                                 18

<210> SEQ ID NO 47
<211> LENGTH: 22
<212> TYPE: DNA
<213> ORGANISM: Artificial Sequence
<220> FEATURE:
<223> OTHER INFORMATION: Synthetic primer

<400> SEQUENCE: 47
tgacataaac cgactccacg tt                                            22

<210> SEQ ID NO 48
<211> LENGTH: 28
<212> TYPE: DNA
<213> ORGANISM: Artificial Sequence
<220> FEATURE:
<223> OTHER INFORMATION: Synthetic probe

<400> SEQUENCE: 48
tccaccttca ccatgtccag aatttcca                                      28

<210> SEQ ID NO 49
<211> LENGTH: 21
<212> TYPE: DNA
<213> ORGANISM: Artificial Sequence
<220> FEATURE:
<223> OTHER INFORMATION: Synthetic primer

<400> SEQUENCE: 49
cacggcactg attttcagtt c                                             21

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
tcttgctgcc agtctggact                                               20

<210> SEQ ID NO 51
<211> LENGTH: 25
<212> TYPE: DNA
<213> ORGANISM: Artificial Sequence
<220> FEATURE:
<223> OTHER INFORMATION: Synthetic probe

<400> SEQUENCE: 51
tgtgcacagg agccaagagt gaaga                                         25

<210> SEQ ID NO 52
<211> LENGTH: 720
<212> TYPE: DNA
<213> ORGANISM: Artificial Sequence
<220> FEATURE:
<223> OTHER INFORMATION: Synthetic scFv sequence
```

<400> SEQUENCE: 52

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg gctggagtg gtctcaatt attggtactg atggtgatga tacaaattac     180
gcagactccg tgaagggccg gttcaccatc tccagagaca attccaagaa cacgctgtat   240
ctgcaaatga acagcctgag agccgaggac acggccgtat attactgtgc gaaagctgaa   300
gctagttttg actactgggg ccagggaacc ctggtcaccg tctcgagcgg tggaggcggt   360
tcaggcggag gtggcagcgg cggtggcggg tcgacggaca tccagatgac ccagtctcca   420
tcctccctgt ctgcatctgt aggagacaga gtcaccatca cttgccgggc aagtcagagc   480
attagcagct atttaaattg gtatcagcag aaaccaggga agcccctaa gctcctgatc    540
tatggtgcat ccgatttgca aagtggggtc ccatcaaggt tcagtggcag tggatctggg   600
acagatttca ctctcaccat cagcagtctg caacctgaag attttgcaac ttactactgt   660
caacagtatg attctgctcc tagtacgttc ggccaaggga ccaaggtgga atcaaacgg    720
```

<210> SEQ ID NO 53
<211> LENGTH: 240
<212> TYPE: PRT
<213> ORGANISM: Artificial Sequence
<220> FEATURE:
<223> OTHER INFORMATION: Synthetic scFv sequence

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Gly Thr Asp Gly Asp Asp Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Glu Ala Ser Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Asp Leu Gln Ser Gly Val Pro Ser
            180                 185                 190

Arg Phe Ser Gly Ser Gly Ser Gly Thr Asp Phe Thr Leu Thr Ile Ser
        195                 200                 205
```

```
Ser Leu Gln Pro Glu Asp Phe Ala Thr Tyr Tyr Cys Gln Gln Tyr Asp
    210                 215                 220

Ser Ala Pro Ser Thr Phe Gly Gln Gly Thr Lys Val Glu Ile Lys Arg
225                 230                 235                 240
```

<210> SEQ ID NO 54
<211> LENGTH: 24
<212> TYPE: DNA
<213> ORGANISM: Artificial Sequence
<220> FEATURE:
<223> OTHER INFORMATION: Synthetic primer

<400> SEQUENCE: 54

```
tggaattgtg agcggataac aatt                                              24
```

<210> SEQ ID NO 55
<211> LENGTH: 23
<212> TYPE: DNA
<213> ORGANISM: Artificial Sequence
<220> FEATURE:
<223> OTHER INFORMATION: Synthetic primer

<400> SEQUENCE: 55

```
gtaaatgaat tttctgtatg agg                                               23
```

<210> SEQ ID NO 56
<211> LENGTH: 1389
<212> TYPE: DNA
<213> ORGANISM: Artificial Sequence
<220> FEATURE:
<223> OTHER INFORMATION: Recombinant DENND1.V2 IgG1 heavy chain

<400> SEQUENCE: 56

```
atggatagcc gtctgaacct ggtcttcctg gtcctgattc tgaaaggggt ggaggtgcag        60
ctgttggagt ctgggggagg cttggtacag cctggggggt ccctgagact ctcctgtgca       120
gcctctggat tcacctttag cagctatgcc atgagctggg tccgccaggc tccagggaag       180
gggctggagt gggtctcaat tattggtact gatggtgatg atacaaatta cgcagactcc       240
gtgaagggcc ggttcaccat ctccagagac aattccaaga acacgctgta tctgcaaatg       300
aacagcctga gagccgagga cacggccgta tattactgtg cgaaagctga agctagtttt       360
gactactggg gccagggaac cctggtcacc gtctcgagcg ctagcaccaa gggcccatcg       420
gtcttccccc tggcaccctc ctccaagagc acctctgggg gcacagcggc cctgggctgc       480
ctggtcaagg actacttccc cgaaccggtg acggtgtcgt ggaactcagg cgccctgacc       540
agcggcgtgc acaccttccc ggctgtccta cagtcctcag gactctactc cctcagcagc       600
gtggtgaccg tgccctccag cagcttgggc acccagacct acatctgcaa cgtgaatcac       660
aagcccagca acaccaaggt ggacaagaaa gttgagccca atcttgtga caaaactcac       720
acatgcccac cgtgcccagc acctgaactc ctggggggac cgtcagtctt cctcttcccc       780
ccaaaaccca aggacaccct catgatctcc cggacccctg aggtcacatg cgtggtggtg       840
gacgtgagcc acgaagaccc tgaggtcaag ttcaactggt acgtggacgg cgtggaggtg       900
cataatgcca agacaaagcc gcgggaggag cagtacaaca gcacgtaccg tgtggtcagc       960
gtcctcaccg tcctgcacca ggactggctg aatggcaagg agtacaagtg caaggtctcc      1020
aacaaagccc tcccagcccc catcgagaaa accatctcca aagccaaagg gcagccccga      1080
gaaccacagg tgtacaccct gcctccatct cgggatgagc tgaccaagaa ccaggtcagc      1140
ctgacctgcc tggtcaaagg cttctatccc agcgacatcg ccgtggagtg ggagagcaat      1200
```

| | |
|---|---|
| gggcagccgg agaacaacta caagaccacg cctcccgtgc tggactccga cggctccttc | 1260 |
| ttcctctata gcaagctcac cgtggacaag agcaggtggc agcagggaa cgtcttctca | 1320 |
| tgctccgtga tgcatgaggc tctgcacaac cactacacgc agaagagcct ctccctgtct | 1380 |
| ccgggtaaa | 1389 |

<210> SEQ ID NO 57
<211> LENGTH: 699
<212> TYPE: DNA
<213> ORGANISM: Artificial Sequence
<220> FEATURE:
<223> OTHER INFORMATION: Recombinant DENND1.V2 IgG1 light chain

<400> SEQUENCE: 57

| | |
|---|---|
| atgggttggt cctgtattat cctgttcctg gtcgctactg ctactggggt gcatagtgac | 60 |
| atccagatga cccagtctcc atcctccctg tctgcatctg taggagacag agtcaccatc | 120 |
| acttgccggg caagtcagag cattagcagc tatttaaatt ggtatcagca gaaaccaggg | 180 |
| aaagccccta agctcctgat ctatggtgca tccgatttgc aaagtggggt cccatcaagg | 240 |
| ttcagtggca gtggatctgg gacagatttc actctcacca tcagcagtct gcaacctgaa | 300 |
| gattttgcaa cttactactg tcaacagtat gattctgctc ctagtacgtt cggccaaggg | 360 |
| accaaggtgg aaatcaaacg tacggtggct gcaccatctg tcttcatctt cccgccatct | 420 |
| gatgagcagt tgaaatctgg aactgcctct gttgtgtgcc tgctgaataa cttctatccc | 480 |
| agagaggcca aagtacagtg gaaggtggat aacgccctcc aatcgggtaa ctcccaggag | 540 |
| agtgtcacag agcaagacag caaggacagc acctacagcc tcagcagcac cctgacgctg | 600 |
| agcaaagcag actacgagaa acacaaagtc tacgcctgcg aagtcaccca tcagggcctg | 660 |
| agctcgcccg tcacaaagag cttcaacagg ggagagtgt | 699 |

<210> SEQ ID NO 58
<211> LENGTH: 465
<212> TYPE: PRT
<213> ORGANISM: Artificial Sequence
<220> FEATURE:
<223> OTHER INFORMATION: Recombinant DENND1.V2 IgG1 heavy chain

<400> SEQUENCE: 58

```
Met Asp Ser Arg Leu Asn Leu Val Phe Leu Val Leu Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ile Ile Gly Thr Asp Gly Asp Asp Thr Asn Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Ala Glu Ala Ser Phe Asp Tyr Trp Gly Gln Gly
        115                 120                 125

Thr Leu Val Thr Val Ser Ser Ala Ser Thr Lys Gly Pro Ser Val Phe
    130                 135                 140
```

```
Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 59
<211> LENGTH: 234
<212> TYPE: PRT
<213> ORGANISM: Artificial Sequence
<220> FEATURE:
<223> OTHER INFORMATION: Recombinant DENND1.V2 IgG1 light chain

<400> SEQUENCE: 59

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30
```

Ala Ser Val Gly Asp Arg Val Thr Ile Thr Cys Arg Ala Ser Gln Ser
            35                  40                  45

Ile Ser Ser Tyr Leu Asn Trp Tyr Gln Gln Lys Pro Gly Lys Ala Pro
 50                  55                  60

Lys Leu Leu Ile Tyr Gly Ala Ser Asp Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asp
            100                 105                 110

Ser Ala Pro Ser Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 60
<211> LENGTH: 351
<212> TYPE: DNA
<213> ORGANISM: Artificial Sequence
<220> FEATURE:
<223> OTHER INFORMATION: P1B2 heavy chain

<400> SEQUENCE: 60
cagcagtctg ggcagacct tgtgaggtca ggggcctcag tcaagttgtc ctgcacagct      60
tctggcttca acattaaaga cttctatatg cactgggtga agcagaggcc tgaacagggc    120
ctggagtgga ttggatggat tgatcctgag aatggtgata ctgattatgc cccgaagttc    180
cagggcaggg ccactatgac tgcagacaca tcctccaaca cagcctacct gcagctcaac    240
agcctcacat ctgaggacac tgccgtctat tactgtaatg cccatacctt cctgcatggt    300
aactccgaac ctatggacta ctggggtcaa ggaacctcag tcaccgtctc c             351

<210> SEQ ID NO 61
<211> LENGTH: 324
<212> TYPE: DNA
<213> ORGANISM: Artificial Sequence
<220> FEATURE:
<223> OTHER INFORMATION: P1B2 light chain

<400> SEQUENCE: 61
attgtgatga cccagtctcc aaaattcatg tccacatcag taggagacag ggtcagcatc     60
acctgcaagg ccagtcagga tgtgattgct gctgttgcct ggtatcaaca gaaaccagga    120
caatctcctg aactactgat ttactcggca tcctaccgct acactggagt ccctgatcgc    180
ttcactggca gtggatctgg gacggatttc actttcacca tcagcagtgt gcaggctgaa    240

-continued

```
gacctggcag tttattactg tcagcaacat tatagtactc cgtggacgtt cggtggaggc    300
accaagctgg acatcaaacg ggct                                            324
```

<210> SEQ ID NO 62
<211> LENGTH: 118
<212> TYPE: PRT
<213> ORGANISM: Artificial Sequence
<220> FEATURE:
<223> OTHER INFORMATION: P1B2 heavy chain

<400> SEQUENCE: 62

```
Gln Gln Ser Gly Ala Asp Leu Val Arg Ser Gly Ala Ser Val Lys Leu
1               5                   10                  15

Ser Cys Thr Ala Ser Gly Phe Ser Asn Ile Lys Asp Phe Tyr Met His
            20                  25                  30

Trp Val Lys Gln Arg Pro Glu Gln Gly Leu Glu Trp Ile Gly Trp Ile
        35                  40                  45

Asp Pro Glu Asn Gly Asp Thr Asp Tyr Ala Pro Lys Phe Gln Gly Arg
    50                  55                  60

Ala Thr Met Thr Ala Asp Thr Ser Ser Asn Thr Ala Tyr Leu Gln Leu
65                  70                  75                  80

Asn Ser Leu Thr Ser Glu Asp Thr Ala Val Tyr Tyr Cys Asn Ala His
                85                  90                  95

Thr Phe Leu His Gly Asn Ser Glu Pro Met Asp Tyr Trp Gly Gln Gly
            100                 105                 110

Thr Ser Val Thr Val Ser
        115
```

<210> SEQ ID NO 63
<211> LENGTH: 108
<212> TYPE: PRT
<213> ORGANISM: Artificial Sequence
<220> FEATURE:
<223> OTHER INFORMATION: P1B2 light chain

<400> SEQUENCE: 63

```
Ile Val Met Thr Gln Ser Pro Lys Phe Met Ser Thr Ser Val Gly Asp
1               5                   10                  15

Arg Val Ser Ile Thr Cys Lys Ala Ser Gln Asp Val Ile Ala Ala Val
            20                  25                  30

Ala Trp Tyr Gln Gln Lys Pro Gly Gln Ser Pro Glu Leu Leu Ile Tyr
        35                  40                  45

Ser Ala Ser Tyr Arg Tyr Thr Gly Val Pro Asp Arg Phe Thr Gly Ser
    50                  55                  60

Gly Ser Gly Thr Asp Phe Thr Phe Thr Ile Ser Ser Val Gln Ala Glu
65                  70                  75                  80

Asp Leu Ala Val Tyr Tyr Cys Gln Gln His Tyr Ser Thr Pro Trp Thr
                85                  90                  95

Phe Gly Gly Gly Thr Lys Leu Asp Ile Lys Arg Ala
            100                 105
```

<210> SEQ ID NO 64
<211> LENGTH: 357
<212> TYPE: DNA
<213> ORGANISM: Artificial Sequence
<220> FEATURE:
<223> OTHER INFORMATION: P1C5 heavy chain -continued

```
<220> FEATURE:
<221> NAME/KEY: misc_feature
<222> LOCATION: (6)..(6)
<223> OTHER INFORMATION: n is a, c, g, or t

<400> SEQUENCE: 64
caagtncagc tgcagcagtc tggggcagag cttgtgaggt caggggcctc agtcaagttg      60
tcctgcacag cttctggctt caacattaaa gactactata tgcactgggt gaagcagagg    120
cctgaacagg gcctggagtg gattggatgg attgatcctg agaatggtga tactgaatat    180
gccccgaagt tccagggcaa ggccactctg actgcagaca tcctccaa cacagcctac     240 ctgcaactca gcagcctgac atctgaggac actgccgtct attactgtaa tgcccactac    300
ggtactagcc aggggctat ggactactgg ggtcaaggaa cctcagtcac cgtctcc       357

<210> SEQ ID NO 65
<211> LENGTH: 119
<212> TYPE: PRT
<213> ORGANISM: Artificial Sequence
<220> FEATURE:
<223> OTHER INFORMATION: P1C5 heavy chain

<400> SEQUENCE: 65

Gln Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Leu Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala His Tyr Gly Thr Ser Gln Gly Ala Met Asp Tyr Trp Gly Gln
            100                 105                 110

Gly Thr Ser Val Thr Val Ser
        115

<210> SEQ ID NO 66
<211> LENGTH: 4
<212> TYPE: PRT
<213> ORGANISM: Artificial Sequence
<220> FEATURE:
<223> OTHER INFORMATION: Synthetic epitope

<400> SEQUENCE: 66

Asn Thr Ile Ala
1

<210> SEQ ID NO 67
<211> LENGTH: 4
<212> TYPE: PRT
<213> ORGANISM: Artificial Sequence
<220> FEATURE:
<223> OTHER INFORMATION: Synthetic epitope

<400> SEQUENCE: 67

Thr Ile Ala Thr
1
```

```
<210> SEQ ID NO 68
<211> LENGTH: 4
<212> TYPE: PRT
<213> ORGANISM: Artificial Sequence
<220> FEATURE:
<223> OTHER INFORMATION: Synthetic epitope

<400> SEQUENCE: 68

Ile Ala Thr Pro
1

<210> SEQ ID NO 69
<211> LENGTH: 4
<212> TYPE: PRT
<213> ORGANISM: Artificial Sequence
<220> FEATURE:
<223> OTHER INFORMATION: Synthetic epitope

<400> SEQUENCE: 69

Ala Thr Pro Ala
1

<210> SEQ ID NO 70
<211> LENGTH: 7
<212> TYPE: PRT
<213> ORGANISM: Artificial Sequence
<220> FEATURE:
<223> OTHER INFORMATION: Synthetic epitope
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 70

Xaa Xaa Asn Thr Ile Ala Xaa
1               5

<210> SEQ ID NO 71
<211> LENGTH: 116
<212> TYPE: PRT
<213> ORGANISM: Artificial Sequence
<220> FEATURE:
<223> OTHER INFORMATION: VH with mutated cysteines

<400> SEQUENCE: 71

Glu Val Gln Leu Leu Glu Ser Gly Gly Gly Leu Val Gln Pro Gly Gly
1               5                   10                  15

Ser Leu Arg Leu Ser Ser Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Gly Thr Asp Gly Asp Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Lys Ala Glu Ala Ser Phe Asp Tyr Trp Gly Gln Gly Thr Leu Val
            100                 105                 110

Thr Val Ser Ser
            115
```

```
<210> SEQ ID NO 72
<211> LENGTH: 116
<212> TYPE: PRT
<213> ORGANISM: Artificial Sequence
<220> FEATURE:
<223> OTHER INFORMATION: VH with additional glycosylation site

<400> SEQUENCE: 72

Glu Val Gln Leu Leu Glu Ser Gly Gly Gly Leu Val Gln Pro Gly Gly
1               5                   10                  15

Ser Leu Arg Leu Ser Ser Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ile Ile Gly Thr Asp Gly Asp Asp Thr Asn Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Lys Ala Glu Ala Ser Phe Asp Tyr Trp Gly Gln Gly Thr Leu Val
            100                 105                 110

Thr Val Ser Ser
            115
```